(12) United States Patent
Slatter et al.

(10) Patent No.: US 11,685,946 B2
(45) Date of Patent: *Jun. 27, 2023

(54) COMPLEX SURFACE-BOUND TRANSPOSOME COMPLEXES

(71) Applicant: ILLUMINA CAMBRIDGE LIMITED, Cambridge (GB)

(72) Inventors: Andrew Slatter, Cambridge (GB); Esther Musgrave-Brown, Cambridge (GB); Susan C. Verity, Cambridge (GB); Niall Anthony Gormley, Cambridge (GB)

(73) Assignee: Illumina Cambridge Limited

( * ) Notice: Subject to any disclaimer, the term of this patent is extended or adjusted under 35 U.S.C. 154(b) by 205 days.

This patent is subject to a terminal disclaimer.

(21) Appl. No.: 16/739,739

(22) Filed: Jan. 10, 2020

(65) Prior Publication Data

US 2020/0224246 A1 Jul. 16, 2020

Related U.S. Application Data

(60) Provisional application No. 62/840,610, filed on Apr. 30, 2019, provisional application No. 62/791,509, filed on Jan. 11, 2019.

(51) Int. Cl.
*C12Q 1/68* (2018.01)
*C12Q 1/6806* (2018.01)
*C12Q 1/6834* (2018.01)
*C12Q 1/6869* (2018.01)

(52) U.S. Cl.
CPC ......... *C12Q 1/6806* (2013.01); *C12Q 1/6834* (2013.01); *C12Q 1/6869* (2013.01)

(58) Field of Classification Search
USPC .......................................................... 435/6
See application file for complete search history.

(56) References Cited

U.S. PATENT DOCUMENTS

| | | | |
|---|---|---|---|
| 7,057,026 B2 | 6/2006 | Barnes et al. |
| 7,211,414 B2 | 5/2007 | Hardin et al. |
| 7,315,019 B2 | 1/2008 | Turner et al. |
| 7,329,492 B2 | 2/2008 | Hardin et al. |
| 7,405,281 B2 | 7/2008 | Xu et al. |
| 9,080,211 B2 | 7/2015 | Grunenwald et al. |
| 9,085,801 B2 | 7/2015 | Grunenwald et al. |

(Continued)

FOREIGN PATENT DOCUMENTS

| | | |
|---|---|---|
| WO | 1991006678 A1 | 5/1991 |
| WO | 2004018497 A3 | 6/2004 |

(Continued)

OTHER PUBLICATIONS

Mulqueen et al, High-content single-cell combinatorial indexing, Nat Biotechnol. Jul. 5, 2021. doi: 10.1038/s41587-021-00962-z.*

(Continued)

*Primary Examiner* — Aaron A Priest
(74) *Attorney, Agent, or Firm* — McNeill Baur PLLC

(57) ABSTRACT

The present disclosure relates to methods, compositions, and kits for generating a library of tagged nucleic acid fragments without using PCR amplification, including methods and compositions for fragmenting and tagging nucleic acids (e.g., DNA) using transposome complexes immobilized on solid support.

11 Claims, 22 Drawing Sheets

Specification includes a Sequence Listing.

(56) References Cited

U.S. PATENT DOCUMENTS

| | | | |
|---|---|---|---|
| 9,115,396 B2 | 8/2015 | Grunenwald et al. | |
| 2008/0108082 A1 | 5/2008 | Rank et al. | |
| 2008/0280773 A1 | 11/2008 | Fedurco et al. | |
| 2011/0059865 A1 | 3/2011 | Smith et al. | |
| 2013/0203605 A1* | 8/2013 | Shendure | C12N 15/1093 506/2 |
| 2014/0093916 A1 | 4/2014 | Belyaev | |
| 2014/0194324 A1* | 7/2014 | Gormley | C12Q 1/6874 506/17 |
| 2015/0291942 A1* | 10/2015 | Gloeckner | C12N 9/1241 506/26 |
| 2017/0283864 A1* | 10/2017 | Ach | C12Q 1/6848 |
| 2018/0016630 A1* | 1/2018 | Godwin | C12Q 1/6853 |
| 2018/0291371 A1* | 10/2018 | Geng | C12N 15/1093 |
| 2018/0340169 A1* | 11/2018 | Belhocine | C12N 15/1068 |
| 2019/0127792 A1* | 5/2019 | Lebofsky | C12Q 1/6806 |
| 2020/0362390 A1* | 11/2020 | Salk | C12Q 1/6869 |

FOREIGN PATENT DOCUMENTS

| | | |
|---|---|---|
| WO | 2005065814 A1 | 7/2005 |
| WO | 2007123744 A3 | 11/2008 |
| WO | 2014108810 A2 | 7/2014 |
| WO | 2015026853 A2 | 2/2015 |
| WO | 2015160895 A3 | 1/2016 |
| WO | 2016061517 A2 | 4/2016 |
| WO | 2016189331 A1 | 12/2016 |
| WO | 2018156519 A1 | 8/2018 |
| WO | 2018208699 A1 | 11/2018 |

OTHER PUBLICATIONS

Bentley et al., "Accurate whole human genome sequencing using reversible terminator chemistry", vol. 456, Nov. 6, 2008, pp. 53-59.

Goryshin et al., "Tn5 in Vitro Transposition", The Journal of Biological Chemistry, vol. 273, No. 13, Mar. 27, 1998, pp. 7367-7374.

Feng et al., "Next-generation sequencing library construction on a surface", BMC Genomics, vol. 19, No. 1, May 30, 2018, pp. 1-6.

International Search Report and Written Opinion, International Application No. PCT/EP2020/050612, dated May 20, 2020, 18 pages.

Picelli, "Single-cell RNA-sequencing: The future of genome biology is now", RNA Biology, vol. 14, No. 5, Jul. 21, 2016, pp. 637-650.

Office Action received in Russian Application No. 2021108087, dated Feb. 21, 2022, 7 pages (English translation).

* cited by examiner

COMPLEX SURFACE-BOUND TRANSPOSOME COMPLEXES

INCORPORATION BY REFERENCE TO ANY PRIORITY APPLICATIONS

The present application claims the benefit of priority to U.S. Provisional Patent Application No. 62/791,509, filed Jan. 11, 2019, and U.S. Provisional Patent Application 62/840,610, filed Apr. 30, 2019, which are hereby incorporated by reference in their entireties.

FIELD

The present disclosure relates to methods, compositions, and kits for generating a library of tagged nucleic acid fragments without using PCR amplification, including methods and compositions for fragmenting and tagging nucleic acids (e.g., DNA) using transposome complexes immobilized on solid supports.

BACKGROUND

Current protocols for next-generation sequencing (NGS) of nucleic acid samples routinely employ a sample preparation process that converts DNA or RNA into a library of fragmented templates that can be sequenced. Sample preparation methods often require multiple steps and material transfers and expensive instruments to effect fragmentation, which can make these methods difficult, tedious, expensive and inefficient. Furthermore, amplification using primers introduces bias in the library content and thus into the resulting sequencing data. For example, PCR amplification steps may generate gaps, which are exacerbated in GC rich regions due to the inability of polymerases to efficiently copy GC rich regions. These gaps create bias in the resulting sequencing data from the libraries. Library preparation processes with PCR amplification steps may have significantly reduced insertion and deletion (indel) calling performance. Some regions with multiple expanded repeats may be difficult to sequence accurately and DNA having GC-rich promoters may exhibit low coverage within the genome. Furthermore, many library preparation methods are not compatible with incorporation of sample indices or require multiple additional steps to introduce such indices.

Library preparation procedures that are short, efficient, and accurate are needed. Herein are described various methods, compositions, and kits that address these problems and that accommodate single and dual indexing approaches.

SUMMARY

The present disclosure relates to methods, compositions, and kits for generating a library of tagged nucleic acid fragments without using PCR amplification to incorporate the fragment tags, such as primer sequences and/or index sequences, including methods and compositions for fragmenting and tagging nucleic acids (e.g., DNA) using transposome complexes immobilized on solid supports.

Some embodiments provided herein relate to a transposome complex that includes an attachment polynucleotide. In some aspects, the disclosure relates to a transposome complex comprising: (a) a transposase; (b) a first transposon including a 3' transposon end sequence and a 5' adaptor sequence; (c) a second transposon including a 5' transposon end sequence and a 3' adaptor sequence, wherein the 5' transposon end sequence is complementary to at least a portion of the 3' transposon end sequence; and (d) an attachment polynucleotide including: (i) an attachment adaptor sequence hybridized to one of the two adaptor sequences and (ii) a binding element. Typically, the transposon end sequences are annealed together, forming a double-stranded transposon end sequence that is recognized by a transposase. In some aspects, the binding element is immobilized to a solid support to provide an immobilized transposome complex.

In some aspects, the disclosure relates to an annealed transposon/attachment polynucleotide hybrid comprising the first transposon, the second transposon, and the attachment polynucleotide.

In some aspects, the disclosure relates to methods of making an annealed transposon/attachment polynucleotide hybrid comprising transposome complex comprising annealing the first transposon, the second transposon, and the attachment polynucleotide. In some aspects, the disclosure relates to methods of making a transposome complex comprising treating an annealed transposon/attachment polynucleotide hybrid with a transposase. In some aspects, the method provides a method of making an immobilized transposome complex by immobilizing the transposome complex to the solid support through the binding element.

In some aspects, the disclosure relates to a transposome complex comprising: (a) a transposase; (b) a first transposon comprising a 3' transposon end sequence and a 5' adaptor sequence; (c) a second transposon comprising a 5' transposon end sequence complementary to at least a portion of the 3' transposon end sequence and a 3' adaptor sequence; and (d) a binding element attached to the 5' adaptor sequence through a cleavable linker. In some aspects, the binding element is immobilized to a solid support, providing an immobilized transposome complex. In some aspects, the disclosure relates to an annealed oligonucleotide construct comprising the first transposon, the second transposon, and the binding element.

In some aspects, the disclosure relates to methods of generating a library of tagged nucleic acid fragments comprising contacting a target nucleic acid with a plurality of immobilized transposome complexes as described herein under conditions sufficient to fragment the target nucleic acid into a plurality of target fragments and to join the 3' ends of the 3' transposon end sequences to the 5' ends of the target fragments to produce a plurality of 5' tagged target fragments.

Some embodiments provided herein relate to a kit for generating a library of tagged nucleic acid fragments without using PCR amplification. In some embodiments, the kit includes an immobilized transposome complex as described herein.

In some aspects, the disclosure relates to methods of generating a library of tagged nucleic acid fragments comprising contacting an immobilized transposome complex with a target nucleic acid under conditions sufficient to fragment the target nucleic acid into a plurality of target fragments, and to join the 3' end of the first transposon to the 5' ends of the target fragments to produce a plurality of 5' tagged target fragments; treating the solid support to remove unbound nucleic acids; or treating the solid support to remove the transposase from the complex, optionally by (a) heating the solid support and/or (b) washing the solid support with an enzyme denaturing agent, wherein the enzyme denaturing agent optionally comprises sodium dodecyl sulfate (SDS), guanidine hydrochloride, urea, or proteinase; treating the plurality of 5' tagged target fragments with a polymerase and a ligase to extend and ligate the 5' tagged target fragments to produce fully double-stranded tagged fragments, optionally wherein the treating with a polymerase and a ligase is done in the presence of a DNA secondary structure disruptor, wherein the disruptor is optionally DMSO; removing the fully double-stranded tagged fragments from the solid support, optionally wherein the removing comprises applying heat and/or a denaturant sufficient to cleave the fully double-stranded tagged fragments from the solid support, optionally wherein the denaturant is NaOH; and selecting the fully double-stranded tagged fragments using capture beads, optionally wherein the capture beads are magnetic beads, further optionally wherein two separate selecting steps are performed.

In some embodiments, the immobilized transposome complex comprises a solid support; and a transposome complex immobilized to the solid support, wherein the transposome complex comprises a transposase; a first transposon comprising a 3' transposon end sequence and an anchor sequence (Anchor); a second transposon comprising a 5' transposon end sequence and a B15' sequence; and an attachment polynucleotide comprising an anchor sequence complement (Anchor'), an A14' sequence, a spacer, and a P5' sequence and a binding element comprising biotin, wherein the biotin is immobilized to the solid support. In some embodiments, a method further comprises sequencing one or more of the fully double-stranded tagged fragments.

In some embodiments, a method comprises contacting a first immobilized transposome complex and a second immobilized transposome complex with a target nucleic acid under conditions sufficient to fragment the target nucleic acid into a plurality of target fragments, and to join the 3' end of each first transposon to the 5' ends of the target fragments to produce a plurality of first 5' tagged target fragments generated from the first immobilized transposome complex and a plurality of second 5' tagged target fragments generated from the second immobilized transposome complex. In some embodiments, the first immobilized transposome complex comprises a solid support and a first transposome complex immobilized to the solid support, wherein the first transposome complex comprises a transposase; a first transposon comprising a 3' transposon end sequence and an anchor sequence; a second transposon comprising a 5' transposon end sequence; and a first attachment polynucleotide comprising (i) an anchor sequence complement, an A14' sequence, a spacer, and a P5' sequence, and (ii) a binding element comprising biotin, wherein the biotin is immobilized to the solid support. In some embodiments, the second immobilized transposome complex comprises a solid support and a second transposome complex immobilized to the solid support, wherein the second transposome complex comprises a transposase; a first transposon comprising a 3' transposon end sequence and an anchor sequence; a second transposon comprising a 5' transposon end sequence; and a second attachment polynucleotide comprising (i) an anchor sequence complement, a B15' sequence, a spacer, and a P7' sequence, and (ii) a binding element comprising biotin, wherein the biotin is immobilized to the solid support. In some embodiments, the method comprises treating the plurality of 5' tagged target fragments with a ligase to ligate each 5' tagged target fragment to either a first indexing oligonucleotide or second indexing oligonucleotide by contacting the 5' tagged target fragments with a pool of first and second indexing oligonucleotides, wherein each first indexing oligonucleotide comprises an A14 sequence, i5 sequence, and P5 sequence and can associate with a first 5' tagged target fragment; and wherein each second indexing oligonucleotide comprises a B15 sequence, i7 sequence, and P7 sequence and can associate with a second 5' tagged target fragment, to produce a plurality of 5' tagged target fragments ligated to indexing oligonucleotides; treating the solid support to remove the transposases from the complex, optionally by (a) heating the solid support and/or (b) washing the solid support with an enzyme denaturing agent, wherein the enzyme denaturing agent optionally comprises sodium dodecyl sulfate (SDS), guanidine hydrochloride, urea, or proteinase; and treating the plurality of 5' tagged target fragments ligated to indexing oligonucleotides with a polymerase to extend and produce fully double-stranded tagged fragments. In some embodiments, the contacting a first immobilized transposome complex and a second immobilized transposome complex and the treating the plurality of 5' tagged target fragments with a ligase are performed in a single reaction. In some embodiments, the double-stranded tagged fragments are produced in solution.

BRIEF DESCRIPTION OF THE DRAWINGS

FIG. 2A is an exemplary configuration of a transposome complex with a biotin (B) attached to one transposon through a cleavable linker. In this exemplary embodiment of a transposome complex comprising a transposase, a first transposon comprising a 3' transposon end sequence and a 5' adaptor sequence; a second transposon comprising a 5' transposon end sequence complementary to at least a portion of the 3' transposon end sequence and a 3' adaptor sequence; and a binding element attached to the 5' adaptor sequence through a cleavable linker (FIG. 2A). FIG. 2B schematically illustrates exemplary steps of a method of preparing a library of tagged nucleic acid fragments without using PCR amplification, using the exemplary transposome complex from FIG. 2A immobilized to a solid support (solid support is not shown), including steps of tagmenting and washing, extending and ligating, and removing beads. FIG. 2B shows the steps of tagmentation where inserts from the target nucleic acid are appended with the tags, extension and ligation, and cleavage from the solid support.

FIG. 3A depicts a transposome complex immobilized to a solid support through an attachment polynucleotide bearing a biotin (B, solid support not shown). For simplicity, the depiction of the dimer is shown in FIG. 3A, but not in FIGS. 3B-3C. FIG. 3B depicts a tagged and fragmented nucleic acid, still complexed to the transposase (top panel) and structure after removal of transposase (bottom panel). FIG. 3B depicts the transposome complex having a nucleic acid fragment (insert) bound to the first transposon, with the 5' end of the insert attached to the 3' transposon end sequence. Transposase is removed using methods described herein, for example, with the use of an agent to remove transposase, such as with sodium dodecyl sulfate (SDS). FIG. 3C depicts the structure after gap filling and extension (extension and ligation) (top panel), and after dehybridization to remove the generated fragments from the solid support (bottom panel). As shown in FIG. 3C, indices are added to the solid support, and hybridize to the attachment polynucleotide of the second transposon. Specifically, as shown in the embodiment of FIG. 3C, an i5 index having a primer sequence (P5 sequence), an index sequence (i5 sequence), and an anchor sequence hybridizes to the attachment polynucleotide at complementary sequences, such that P5 hybridizes to P5', and anchor hybridizes to anchor'. Similarly, in the embodiment of FIG. 3C, an i7 index having a primer sequence (P7), an index sequence (i7), and an adaptor sequence (B15 sequence) hybridizes to the second transposon at complementary sequences, such that the P7 hybridizes to P7', the i7 hybridizes to i7', and B15 hybridizes to B15'. After contacting the solid support with the indices, the fragments are extended and ligated using an extension and ligation mix (ELM). The solid support is then treated with an agent to denature the strand sequences, such as with NaOH, thereby generating tagged nucleic acid fragments. An embodiment of a transposome complex is shown, having a Tn5 transposase with a first and second transposon. The first transposon includes a 3' transposon end sequence (ME sequence) hybridized to a 5' transposon end sequence (ME' sequence) of the second transposon. The second transposon also includes a 3' adaptor sequence (B15' sequence). The first transposon includes a 5' adaptor sequence (A14 sequence), which is shown hybridized to an attachment adaptor sequence (A14' sequence) of an attachment polynucleotide. The attachment polynucleotide also includes an anchor sequence (anchor'), a spacer region, a primer sequence (P5' sequence), and a linker attached to a binding element (B). The transposome complex is a dimer, having two transposome monomers dimerized.

FIG. 4A depicts the various configurations of the transposome complex attached to a solid support. FIG. 4A depicts embodiments of the transposome complexes showing transposase with a first and second transposon, and attached to a solid support through the attachment polynucleotide. FIG. 4B depicts the various configurations after tagmentation. FIG. 4B depicts the tagmentation reaction for indexed or universal beads with single or dual indexing, where the solid support is contacted with nucleic acid fragments (insert), which bind to the 3' transposon end of the first transposon. FIG. 4C depicts the various configurations after extension and ligation. FIG. 4C depicts extension and ligation for indexed or universal beads with single or dual indexing, where the solid support is contacted with an index mix, which hybridize to the transposon or attachment polynucleotide, and wherein the nucleic acid fragments are extended. FIG. 4D depicts the various configuration after indexing (the indexed beads for single indexing is not shown, as indexing was completed for this configuration in FIG. 4C). FIG. 4D depicts indexing for indexed beads with dual indexing or universal beads with single or dual indexing. As shown in FIG. 4D, indexed beads with single indexing was completed in the extension-ligation step of FIG. 4C. The solid support is contacted with an indexing mix, and the nucleic acid fragments are tagged for indexing. FIG. 4E depicts exemplary results of the various configurations, showing normalized read frequencies as a function of insert size. FIG. 4E depicts normalized read frequency of tagged nucleic acid fragments from indexed or universal beads with single or dual indexing. FIGS. 4A-4E in particular depict embodiments of the transposome complexes arranged as indexed beads for single indexing (top left), universal beads for single indexing (top right), indexed beads for dual indexing (bottom left), and universal beads for dual indexing. For the embodiments of indexed beads shown in FIGS. 4A-4E, for both single and dual indexing (left), the attachment polynucleotide is hybridized to the second transposon at the 3' adaptor sequence (B15' sequence). For the embodiments of universal beads shown in FIGS. 4A-4E, for both single and dual indexing (right), the attachment polynucleotide is hybridized to the first transposon at the 5' adaptor sequence (A14 sequence). In some embodiments, normalized libraries can be prepared from raw samples, such that a nucleic acid is extracted from a raw sample and directly inputted into a system or method described herein, where a self-normalized sample provides a tight CV across a range of sample types.

FIGS. 5A and 5B depicts a primer sequence (P5 sequence) joined to a 5' adaptor sequence (A14 sequence) on the first transposon, and a primer sequence (P7' sequence) joined to a 3' adaptor sequence (B15' sequence) on the second transposon, thereby providing non-indexing transposome complexes. The attachment polynucleotide could be hybridized on either the second transposon using a 5' binding element (B) (FIG. 5A) or the first transposon using a 3' binding element (B) (FIG. 5B).

FIG. 6A depicts a complex in which an attachment polynucleotide comprising a nitro sequence and an anchor sequence can hybridize to an indexing oligonucleotide, which can then be ligated to the 5' end of the first transposon. In FIG. 6A, the transposome complex comprises a first transposon comprising a 3' transposon end sequence (ME) and a 5' adaptor sequence (A14), a second transposon comprising a 5' transposon end sequence (ME') and a 3' adaptor sequence (B15'), and an attachment polynucleotide comprising an attachment adaptor sequence (A14') hybridized to the A14 in the first transposon, and a binding element (biotin). In this case, the attachment polynucleotide further comprises a nitroindole sequence (a universal sequence that binds to any i5 index region) and a primer sequence (P5'). The B15' region of the second transposon can be hybridized to a polynucleotide comprising the complement (B15), an index region, and a P7 primer sequence, which itself is annealed to a P7'-i7' index molecule. Ligation of the 5' end of the i7' index region to the 3' end of the 3' adaptor sequence serves to generate a fully double-stranded region.

FIG. 6B depicts an attachment polynucleotide comprising an anchor sequence and a spacer region that can hybridize to an indexing oligonucleotide that can then be ligated to the 5' end of the first transposon. In FIG. 6B, the first transposon comprises a 3' transposon end sequence (ME) and a 5' adaptor sequence (A14), and the second transposon comprises a 5' transposon end sequence (ME') and a 3' adaptor sequence (B15') as in FIG. 6A. In this case, though, the attachment polynucleotide comprises an adaptor complement (A14'), an anchor' sequence, a 2×sp 18 spacer region, a primer complement (P5'), and a biotin binding element. An i5 index comprises an anchor sequence (complementary to anchor'), an i5 index region, and a primer sequence (P5). The i5 index hybridizes to the complementary anchor and primer sequences on the attachment polynucleotide across the spacer.

FIG. 6C depicts an attachment polynucleotide comprising a spacer and an A14' sequence that can hybridize to an indexing oligonucleotide, which can then be ligated to sequence X at the 5' end of the first transposon. In FIG. 6C, the first transposon comprises a 3' transposon end sequence (ME) and a 5' adaptor sequence X and the second transposon comprises a 5' transposon end sequence (ME') and a 3' adaptor sequence (B15'). The attachment polynucleotide comprises the complement to the 5' adaptor sequence (X'), a second adaptor sequence (A14'), a spacer region (2×sp18), a primer complement (P5'), and a biotin binding element. The 5' adaptor sequence (X') hybridizes to the first transposon 5' adaptor sequence (X). The i5 index comprises the complement to the second adaptor sequence (A14), a 2×sp18 spacer region, and the primer sequence (P5). The i5 index hybridizes to the second adaptor sequence and primer complement on the attachment polynucleotide, across the spacer region, and the 3' end of the complement to the second adaptor sequence is ligated to sequence X. In addition, an i7 index comprising a 5' primer sequence (P7), an i7 index region, and the complement to the 3' adaptor sequence (B15) is annealed, and the 3' end of the 3' adaptor sequence extended to produce a double-stranded region.

FIG. 6D depicts an attachment polynucleotide comprising a spacer and an A14' sequence that can hybridize to an indexing oligonucleotide, which can then be ligated to sequence X at the 5' end of the first transposon. In this case, the indexing oligonucleotide comprises a double-stranded primer region. In FIG. 6D, the first transposon, second transposon, and attachment polynucleotide are as in FIG. 6C. The i7 index comprises a double-stranded primer (P7/P7'), an i7 index region, and the complement to the 3' adaptor sequence (B15). The double stranded region in the i7 index can be created (annealed) during the extension ligation reaction, e.g., there is no need for the i7 index to be annealed prior to the reaction itself. The P7' oligo can be included in the reaction mix. The i7 index is annealed via the B15 region, and extension and ligation from the second transposon creates the double-stranded region. An example of this method is described in Example 5.

FIG. 7A shows high percentage of indel precision and recall for the PCR-free method described herein. From left to right, the samples include (in duplicate): TruSeq™ Nano (black); Nextera™ DNA Flex (white); the present PCR-free method described herein (lined); and TruSeq™ PCR-Free (checked). FIG. 7B shows an improvement in coverage in GC rich promoters for the present PCR-free method described herein as compared to other methods, including: Nextera™ DNA Flex (top left); TruSeq™ Nano (top right); the present PCR-free method described herein (bottom left); and TruSeq™ PCR-Free (bottom right).

DETAILED DESCRIPTION

Figure 1:
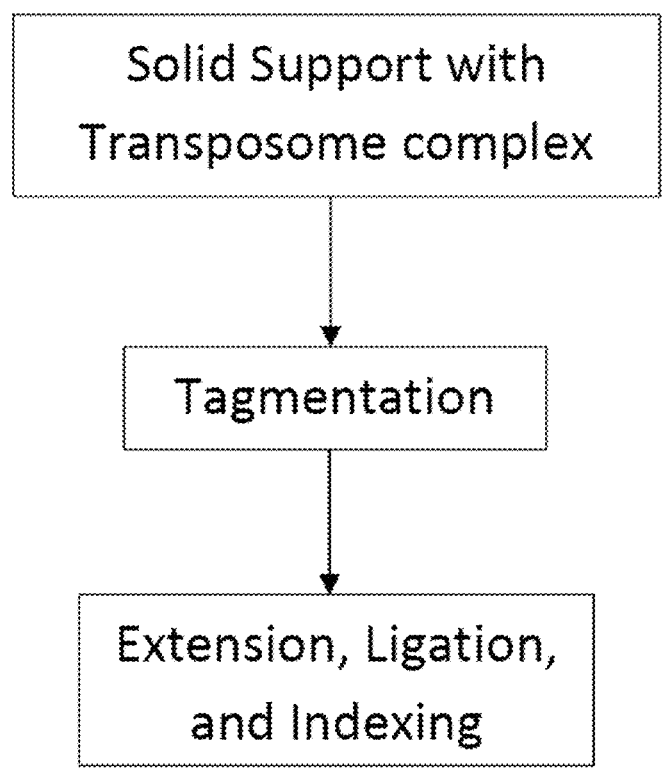
FIG. 1 is a flow diagram that depicts an embodiment of a method of generating a library of tagged nucleic acid fragments without using PCR amplification. In a first step, a transposome complex as described herein and immobilized on a solid support is provided. A target nucleic acid is applied to the solid support, and a tagmentation reaction takes place, generating tagged and fragmented nucleic acids. An index mix having index sequences is applied, and extension and ligation takes place. Finally, indexing of the tagged nucleic acid fragments takes place. In some embodiments, indexing occurs simultaneously with extension and ligation and in other embodiments, indexing occurs after extension and ligation. In other embodiments, the arrangements of steps differ, such as depicted in Example 9.

Libraries of fragmented nucleic acids are often created from genomic nucleic acids for use in next generation sequencing (NGS) applications. The present disclosure provides for methods, compositions, and kits for generating a library of fragmented nucleic acids that appends sequences needed to perform sequencing operations, including indexes, without using PCR to add the sequences by amplification (also referred to herein as PCR-free library generation or PCR-free library preparation). This PCR-free transposome library preparation method may reduce and/or eliminate bias caused by PCR in current tagmentation approaches for library preparation.

Tagmentation refers to the use of transposase to fragment and tag nucleic acids. Tagmentation includes the modification of DNA by a transposome complex comprising transposase enzyme complexed with adaptors comprising transposon end sequences (referred to herein as transposons). Tagmentation results in the simultaneous fragmentation of the DNA and ligation of the adaptors to the 5' ends of both strands of duplex fragments. Generally, following a purification step to remove the transposase enzyme, additional sequences are added to the ends of the adapted fragments by PCR.

The methods, compositions, systems, and kits described herein relate to complex hybridized oligonucleotides, and transposome complexes comprising those hybrids, including complexes that are immobilized on a surface, and the use of the transposome complexes for PCR-free library generation. As described herein, the transposome complex includes a transposase and associated transposons that fragment and tag a target DNA molecule. In some aspects, the complex hybridized oligonucleotide is cleavable and includes a binding element, and in other aspects, the complex hybridized oligonucleotide comprises an attachment polynucleotide with a binding element. In some aspects, the attachment polynucleotide is a nucleic acid sequence that hybridizes to a transposon in a transposome complex and that is immobilized on a solid support, such as a slide, flow cell, or bead. Due to the hybridization of the attachment polynucleotide to a transposon, the transposome complex may be immobilized on a solid support indirectly through the attachment polynucleotide. Binding of the attachment polynucleotide to the solid support takes place through a binding element on the attachment polynucleotide. Target nucleic acids are captured by the transposome complexes and the nucleic acids are then fragmented and tagged ("tagmentation"). The oligonucleotide system is designed to allow for incorporation of any tags needed for indexing and sequencing via tagmentation, extension, and/or ligation steps, without PCR amplification. Thus, in some aspects, tagged fragments may be extended and ligated, and indexed without amplification, to generate a library of nucleic acid fragments without using PCR amplification.

Solution-based tagmentation has drawbacks and requires several labor-intensive steps. Additionally, bias can be introduced during PCR amplification steps used to introduce tag sequences. For example, reduced indel may be a result of PCR due to polymerase slippage. Further, PCR polymerases have difficulty in some regions, such as high GC regions or AT or other sequence repeat regions, which leads to gaps or false structural variance calls in a genome, or missed repeat expansions.

The methods, compositions, systems, and kits presented herein overcome those drawbacks and allow unbiased sample preparation and sequencing to occur with minimal requirements for sample manipulation or transfer. The methods, compositions, systems, and kits described herein relate to generating libraries without the use of PCR amplification. The PCR-free approach reduces and/or eliminates biases caused by PCR, including: reducing the number and frequency of gaps, particularly in GC rich regions that are difficult to PCR; improving indel calling performance, including improving indel recall and indel precision; improving calling of repeat expansions; and improving coverage in GC rich promoters. The present application discloses various transposome complex designs for performing PCR-free tagmentation for improvement of generating nucleic acid libraries.

Furthermore, the methods, compositions, systems, and kits described herein may be performed in a period of time less than nucleic acid sample preparation and analysis using other methods, such as PCR based methods. Thus, in some embodiments, the methods of generating a library of tagged nucleic acid fragments as described herein may be performed in a period of time of less than about 5 hours, for example, less than 5, less than 4, less than 3, or less than 2 hours. In some embodiments, the methods of generating a library of tagged nucleic acid fragments as described herein may be performed in a period of time ranging from about 90 minutes to about 300 minutes, such as 90, 105, 120, 135, 150, 165, 180, 195, 210, 225, 240, 255, 270, 285, or 300 minutes, or for an amount of time within a range defined by any two of the aforementioned values.

Furthermore, in some embodiments, use of the methods, compositions, systems, and kits described herein results in fragmentation of nucleic acids that is not time dependent, immobilization of the transposome results in consistent insert size, and saturation allows for integrated extraction and a quantification-free library preparation.

Additional advantages of the methods, compositions, systems, and kits described herein relate to immobilization of the transposome complex on a solid surface, and include, for example reducing hands-on and overall library preparation time, cost, and reagent requirements, lowering sample input requirements, and enabling the use of unpurified or degraded samples as a starting point for library preparation. In addition, the transposome complexes described herein also produce libraries with more consistent insert sizes relative to solution-phase methods, even when varying sample input concentrations are used.

In some embodiments, the nucleic acid libraries obtained by the methods disclosed herein can be sequenced using any suitable nucleic acid sequencing platform to determine the nucleic acid sequence of the target sequence. In some respects, sequences of interest are correlated with or associated with one or more congenital or inherited disorders, pathogenicity, antibiotic resistance, or genetic modifications. Sequencing may be used to determine the nucleic acid sequence of a short tandem repeat, single nucleotide polymorphism, gene, exon, coding region, exome, or portion thereof. As such, the methods and compositions described herein relate to creating sequenceable libraries useful in, but not limited to, cancer and disease diagnosis, prognosis and therapeutics, DNA fingerprinting applications (e.g., DNA databanking, criminal casework), metagenomic research and discovery, agrigenomic applications, and pathogen identification and monitoring.

In some embodiments, the attachment adaptor sequence is hybridized to at least a portion of the 5' adaptor sequence, and the binding element is at the 3' end of the attachment polynucleotide. In some embodiments, the attachment adaptor sequence is hybridized to at least a portion of the 3' adaptor sequence, and the binding element is at the 5' end of the attachment oligonucleotide.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The section headings used herein are for organizational purposes only and are not to be construed as limiting the subject matter described.

Transposome Complexes

Some embodiments provided herein relate to a composition for generating a library of tagged nucleic acid fragments without PCR amplification. In some embodiments, the composition includes a solid support and a transposome complex immobilized to the solid support. In some embodiments, the transposome complex includes a transposase, a first transposon, an attachment polynucleotide, and a second transposon. In some embodiments, the first transposon includes a 3' transposon end sequence and a 5' adaptor sequence. In some embodiments, the attachment polynucleotide includes an attachment adaptor sequence hybridized to the 5' adaptor sequence and a binding element. In some embodiments, the second transposon comprises a 5' transposon end sequence and a 3' adaptor sequence. In some embodiments, the transposome complex is immobilized to the solid support through the attachment polynucleotide. In some embodiments, the attachment polynucleotide further comprises a primer sequence.

In some embodiments, the binding element comprises or is an optionally substituted biotin. In some embodiments, the binding element is connected to the attachment polynucleotide via a linker. In some embodiments, the binding element comprises or is a biotin linker. In some embodiments, the binding element comprises or is a 3', 5', or internal biotin.

In some embodiments, the 3' transposon end sequence comprises a mosaic end (ME) sequence and the 5' transposon end sequence comprises an ME' sequence. In some embodiments, the 5' adaptor sequence comprises an A14 sequence and the attachment adaptor sequence comprises an A14' sequence. In some embodiments, the 3' adaptor sequence comprises a B15' sequence. In some embodiments, the 3' adaptor sequence is complementary to at least a portion of an index adaptor sequence. In some embodiments, the index adaptor sequence comprises a B15 sequence. In some embodiments, a portion of the attachment polynucleotide comprises a primer sequence, such as a P5' primer sequence. In some embodiments, the primer sequence of the attachment polynucleotide is complementary to at least a portion of an indexing oligonucleotide sequence, such as a P5 primer sequence.

In some embodiments, the transposome complex is immobilized on the solid support via the binding element (and optional linker) as described herein. In some embodiments, the solid support is a bead, a paramagnetic bead, a flowcell, a surface of a microfluidic device, a tube, a well of a plate, a slide, a patterned surface, or a microparticle. In some embodiments, the solid support comprises or is a bead. In one embodiment, the bead is a paramagnetic bead. In some embodiments, the solid support comprises a plurality of solid supports. In some embodiments, transposome complexes are immobilized on a plurality of solid supports. In some embodiments, the plurality of solid supports comprises a plurality of beads. In some embodiments, the plurality of transposome complexes are immobilized on the solid support at a density of at least $10^3$, $10^4$, $10^5$, $10^6$ complexes per $mm^2$. In some embodiments, the solid support is a bead or a paramagnetic bead, and there are greater than 10,000, 20,000, 30,000, 40,000, 50,000, or 60,000 transposome complexes bound to each bead.

Transposon based technology can be utilized for fragmenting DNA, for example, as exemplified in the workflow for NEXTERA™ FLEX DNA sample preparation kits (Illumina, Inc.), wherein target nucleic acids, such as genomic DNA, are treated with transposome complexes that simultaneously fragment and tag ("tagmentation") the target, thereby creating a population of fragmented nucleic acid molecules tagged with unique adaptor sequences at the ends of the fragments.

A transposition reaction is a reaction wherein one or more transposons are inserted into target nucleic acids at random sites or almost random sites. Components in a transposition reaction include a transposase (or other enzyme capable of fragmenting and tagging a nucleic acid as described herein, such as an integrase) and a transposon element that includes a double-stranded transposon end sequence that binds to the transposase (or other enzyme as described herein), and an adaptor sequence attached to one of the two transposon end sequences. One strand of the double-stranded transposon end sequence is transferred to one strand of the target nucleic acid and the complementary transposon end sequence strand is not (a non-transferred transposon sequence). The adaptor sequence can include one or more functional sequences or components (e.g., primer sequences, anchor sequences, universal sequences, spacer regions, or index tag sequences) as needed or desired.

A "transposome complex" is comprised of at least one transposase (or other enzyme as described herein) and a transposon recognition sequence. In some such systems, the transposase binds to a transposon recognition sequence to form a functional complex that is capable of catalyzing a transposition reaction. In some aspects, the transposon recognition sequence is a double-stranded transposon end sequence. The transposase binds to a transposase recognition site in a target nucleic acid and inserts the transposon recognition sequence into a target nucleic acid. In some such insertion events, one strand of the transposon recognition sequence (or end sequence) is transferred into the target nucleic acid, resulting in a cleavage event. Exemplary transposition procedures and systems that can be readily adapted for use with the transposases.

Exemplary transposases that can be used with certain embodiments provided herein include (or are encoded by): Tn5 transposase, Sleeping Beauty (SB) transposase, *Vibrio harveyi*, MuA transposase and a Mu transposase recognition site comprising R1 and R2 end sequences, *Staphylococcus aureus* Tn552, Ty1, Tn7 transposase, Tn/O and IS10, Mariner transposase, Tc1, P Element, Tn3, bacterial insertion sequences, retroviruses, and retrotransposon of yeast. More examples include IS5, Tn10, Tn903, IS911, and engineered versions of transposase family enzymes. The methods described herein could also include combinations of transposases, and not just a single transposase.

In some embodiments, the transposase is a Tn5, Tn7, MuA, or *Vibrio harveyi* transposase, or an active mutant thereof. In other embodiments, the transposase is a Tn5 transposase or a mutant thereof. In other embodiments, the transposase is a Tn5 transposase or a mutant thereof. In other embodiments, the transposase is a Tn5 transposase or an active mutant thereof. In some embodiments, the Tn5 transposase is a hyperactive Tn5 transposase, or an active mutant thereof. In some aspects, the Tn5 transposase is a Tn5 transposase as described in PCT Publ. No. WO2015/160895, which is incorporated herein by reference. In some aspects, the Tn5 transposase is a hyperactive Tn5 with mutations at positions 54, 56, 372, 212, 214, 251, and 338 relative to wild-type Tn5 transposase. In some aspects, the Tn5 transposase is a hyperactive Tn5 with the following mutations relative to wild-type Tn5 transposase: E54K, M56A, L372P, K212R, P214R, G251R, and A338V. In some embodiments, the Tn5 transposase is a fusion protein. In some embodiments, the Tn5 transposase fusion protein comprises a fused elongation factor Ts (Tsf) tag. In some embodiments, the Tn5 transposase is a hyperactive Tn5 transposase comprising mutations at amino acids 54, 56, and 372 relative to the wild type sequence. In some embodiments, the hyperactive Tn5 transposase is a fusion protein, optionally wherein the fused protein is elongation factor Ts (Tsf). In some embodiments, the recognition site is a Tn5-type transposase recognition site (Goryshin and Reznikoff, J. Biol. Chem., 273: 7367, 1998). In one embodiment, a transposase recognition site that forms a complex with a hyperactive Tn5 transposase is used (e.g., EZ-Tn5™ Transposase, Epicentre Biotechnologies, Madison, Wis.). In some embodiments, the Tn5 transposase is a wild-type Tn5 transposase.

In some embodiments, the transposome complex comprises a dimer of two molecules of a transposase. In some embodiments, the transposome complex is a homodimer, wherein two molecules of a transposase are each bound to first and second transposons of the same type (e.g., the sequences of the two transposons bound to each monomer are the same, forming a "homodimer"). In some embodiments, the compositions and methods described herein employ two populations of transposome complexes. In some embodiments, the transposases in each population are the same. In some embodiments, the transposome complexes in each population are homodimers, wherein the first population has a first adaptor sequence in each monomer and the second population has a different adaptor sequence in each monomer.

In some embodiments, the transposase complex comprises a transposase (e.g., a Tn5 transposase) dimer comprising a first and a second monomer. In some aspects, each monomer comprises a first transposon, a second transposon, and an attachment polynucleotide, where the first transposon includes a transposon end sequence at its 3' end (also referred to as a 3' transposon end sequence) and an adaptor sequence at its 5' end (also referred to as a 5' adaptor sequence); the second transposon includes a transposon end sequence at its 5' end (also referred to as a 5' transposon end sequence) and an adaptor sequence at its 3' end (also referred to as a 3' adaptor sequence); and the attachment polynucleotide includes an attachment adaptor sequence hybridized to the 5' adaptor sequence of the first transposon, a primer sequence, and a linker. In some embodiments, the 5' transposon end sequence of the second transposon is at least partially complementary to the 3' transposon end sequence of the first transposon. In some embodiments, the attachment adaptor sequence of the attachment polynucleotide is at least partially complementary to the 5' adaptor sequence of the first transposon. In some embodiments, the linker of the attachment polynucleotide includes a binding element.

End Sequences

In any of the embodiments of the method described herein, the first transposon includes a 3' transposon end sequence and the second transposon includes a 5' transposon end sequence. In some embodiments, the 5' transposon end sequence is at least partially complementary to the 3' transposon end sequence. In some embodiments, the complementary transposon end sequences hybridize to form a double-stranded transposon end sequence that binds to the transposase (or other enzyme as described herein). In some embodiments, the transposon end sequence is a mosaic end (ME) sequence. Thus, in some embodiments, the 3' transposon end sequence is an ME sequence and the 5' transposon end sequence is an ME' sequence.

Adaptor Sequences

In any of the embodiments of the method described herein, the first transposon includes a 5' adaptor sequence and the second transposon includes a 3' adaptor sequence. Adaptor sequences may comprise one or more functional sequences or components selected from the group consisting of primer sequences, anchor sequences, universal sequences, spacer regions, index sequences, capture sequences, barcode sequences, cleavage sequences, sequencing-related sequences, and combinations thereof. In some embodiments, an adaptor sequence comprises a primer sequence. In other embodiments, an adaptor sequence comprises a primer sequence and an index or barcode sequence. A primer sequence may also be a universal sequence. This disclosure is not limited to the type of adaptor sequences that could be used and a skilled artisan will recognize additional sequences that may be of use for library preparation and next generation sequencing. A universal sequence is a region of nucleotide sequence that is common to two or more nucleic acid fragments. Optionally, the two or more nucleic acid fragments also have regions of sequence differences. A universal sequence that may be present in different members of a plurality of nucleic acid fragments can allow for the replication or amplification of multiple different sequences using a single universal primer that is complementary to the universal sequence.

In some embodiments, the attachment polynucleotide includes an attachment adaptor sequence hybridized to the 5' adaptor sequence. In some embodiments, the attachment adaptor sequence is at least partially complementary to the 5' adaptor sequence. In some embodiments, the adaptor sequence is an A14 sequence or a B15 sequence. Thus, in some embodiments, the 5' adaptor sequence is an A14 sequence and the attachment adaptor sequence is an A14' sequence. In some embodiments, the 3' adaptor sequence is a B15' sequence. In some embodiments, the adaptor sequence is any sequence for hybridization (referred to herein as sequence X). In some embodiments, sequence X comprises 16-20 nucleotides. In some embodiments, sequence X has a similar melting temperature (Tm) to an adapter sequence. In some embodiments, sequencing results are improved when the Tm of sequence X has a similar melting temperature to that of an adapter sequence. In some embodiments, sequence X has a similar melting temperature to an A14 sequence or B15 sequence. In some embodiments, the Tm of sequence X is 53°-56°. In some embodiments, adaptor sequences are transferred to the 5' ends of a nucleic acid fragment by a tagmentation reaction.

In any of the embodiments, the adaptor sequence or transposon end sequences, including A14-ME, ME, B15-ME, ME', A14, B15, and ME are provided below:

A14-ME: 5'-TCGTCGGCAGCGTCAGATGTGTAT AAGAGACAG-3' (SEQ ID NO: 1)

B15-ME: 5'-GTCTCGTGGGCTCGGAGATGTGTATAA GAGACAG-3' (SEQ ID NO: 2)

ME': 5'-phos-CTGTCTCTTATACACATCT-3' (SEQ ID NO: 3)

A14: 5'-TCGTCGGCAGCGTC-3' (SEQ ID NO: 4)

B15: 5'-GTCTCGTGGGCTCGG-3' (SEQ ID NO: 5)

ME: AGATGTGTATAAGAGACAG (SEQ ID NO: 6)

Attachment Polynucleotide

Embodiments of the transposome complex described herein include an attachment polynucleotide. As used herein, the attachment polynucleotide is a polynucleotide that hybridizes to a transposon on one end and binds to a surface on a second end. Thus, the transposome complex described herein is immobilized to a solid support through the attachment polynucleotide. In some embodiments, an attachment polynucleotide includes an attachment adaptor sequence hybridized to the adaptor sequence of the first transposon or the adaptor sequence of the second transposon, a primer sequence, and a linker. In some embodiments, the linker includes a binding element.

As described herein the attachment adaptor sequence may be at least partially complementary to the adaptor sequence of the first or second transposon. In some embodiments, the attachment adaptor sequence hybridizes to the 5' adaptor sequence. In embodiments when the attachment adaptor sequence hybridizes to the 5' adaptor sequence, where the 5' adaptor sequence is an A14 sequence, the attachment adaptor sequence is an A14' sequence. In some embodiments, the adaptor sequence is sequence X. In some embodiments, the attachment adaptor sequence hybridizes to the 3' adaptor sequence. In embodiments when the attachment adaptor sequence hybridizes to the 3' adaptor sequence, where the 3' adaptor sequence is a B15' sequence, the attachment adaptor sequence is a B15 sequence. In any of these embodiments, the attachment adaptor sequence may be fully complementary to the adaptor sequence of the first or second transposon or partially complementary to the adaptor sequence of the first or second transposon.

In some embodiments, the attachment polynucleotide contains a primer sequence. In some embodiments, the primer sequence is a P5 primer sequence or a P7 primer sequence or a complement thereof (e.g., P5' or P7'). The P5 and P7 primers are used on the surface of commercial flow cells sold by Illumina, Inc., for sequencing on various Illumina platforms. The primer sequences are described in U.S. Pat. Publ. No. 2011/0059865, which is incorporated herein by reference in its entirety. Examples of P5 and P7 primers, which may be alkyne terminated at the 5' end, include the following:

P5: AATGATACGGCGACCACCGAGAUCTACAC (SEQ ID NO: 7)

P7: CAAGCAGAAGACGGCATACGAG*AT (SEQ ID NO: 8)

and derivatives thereof. In some examples, the P7 sequence includes a modified guanine at the G* position, e.g., an 8-oxo-guanine. In other examples, the * indicates that the bond between the G* and the adjacent 3' A is a phosphorothioate bond. In some examples, the P5 and/or P7 primers include unnatural linkers. Optionally, one or both of the P5 and P7 primers can include a poly T tail. The poly T tail is generally located at the 5' end of the sequence shown above, e.g., between the 5' base and a terminal alkyne unit, but in some cases can be located at the 3' end. The poly T sequence can include any number of T nucleotides, for example, from 2 to 20. While the P5 and P7 primers are given as examples, it is to be understood that any suitable primers can be used in the examples presented herein. The index sequences having the primer sequences, including the P5 and P7 primer sequences serve to add P5 and P7 for activating the library for sequencing. While the P5 and P7 primers are given as examples, it is to be understood that any suitable amplification primers can be used in the examples presented herein.

As used herein, one example of a linker is a moiety that covalently connects a binding element to the end of the nucleotide portion of the attachment polynucleotide and may be used to immobilize the attachment polynucleotide to a solid support. The linker may be a cleavable linker, for example, a linker capable of being cleaved to remove the attachment polynucleotide, and thus the transposome complex or tagmentation product from the solid support. A cleavable linker as used herein is a linker that may be cleaved through chemical or physical means, such as, for example, photolysis, chemical cleavage, thermal cleavage, or enzymatic cleavage. In some embodiments the cleavage may be by biochemical, chemical, enzymatic, nucleophilic, reduction sensitive agent or other means. Cleavable linkers may comprise a moiety selected from the group consisting of: a restriction endonuclease site; at least one ribonucleotide cleavable with an RNAse; nucleotide analogues cleavable in the presence of certain chemical agent(s); photocleavable linker unit; a diol linkage cleavable by treatment with periodate (for example); a disulfide group cleavable with a chemical reducing agent; a cleavable moiety that may be subject to photochemical cleavage; and a peptide cleavable by a peptidase enzyme or other suitable means. Cleavage may be mediated enzymatically by incorporation of a cleavable nucleotide or nucleobase into the cleavable linker, such as uracil or 8-oxo-guanine.

In some embodiments, the linker described herein may be covalently and directly attached the attachment polynucleotide, for example, forming a —O— linkage, or may be covalently attached through another group, such as a phosphate or an ester. Alternatively, the linker described herein may be covalently attached to a phosphate group of the attachment polynucleotide, for example, covalently attached to the 3' hydroxyl via a phosphate group, thus forming a —O—P(O)$_3$— linkage.

A binding element, as used herein, is a moiety that can be used to bind, covalently or non-covalently, to a binding partner. In some aspects, the binding element is on the transposome complex and the binding partner is on the solid support. In some embodiments, the binding element can bind or is bound non-covalently to the binding partner on the solid support, thereby non-covalently attaching the transposome complex to the solid support. In some embodiments, the binding element is capable of binding (covalently or non-covalently) to a binding partner on a solid support. In some aspects, the binding element is bound (covalently or non-covalently) to a binding partner on the solid support, resulting in an immobilized transposome complex.

In such embodiments, the binding element comprises or is, for example, biotin, and the binding partner comprises or is avidin or streptavidin. In other embodiments, the binding element/binding partner combination comprises or is FITC/anti-FITC, digoxigenin/digoxigenin antibody, or hapten/antibody. Further suitable binding pairs include, but not limited to, dithiobiotin-avidin, iminobiotin-avidin, biotin-avidin, dithiobiotin-succinilated avidin, iminobiotin-succinilated avidin, biotin-streptavidin, and biotin-succinilated avidin. In some embodiments, the binding element is a biotin and the binding partner is streptavidin.

In some embodiments, the binding element can bind to the binding partner via a chemical reaction or is bound covalently by reaction with the binding partner on the solid support, thereby covalently attaching the transposome complex to the solid support. In some aspects, the binding element/binding partner combination comprises or is amine/carboxylic acid (e.g., binding via standard peptide coupling reaction under conditions known to one of ordinary skill in the art, such as EDC or NETS-mediated coupling). The reaction of the two components joins the binding element and binding partner through an amide bond. Alternatively, the binding element and binding partner can be two click chemistry partners (e.g., azide/alkyne, which react to form a triazole linkage).

In some embodiments, the attachment polynucleotide further includes additional sequences or components, such as a universal sequence, a spacer region, an anchor sequence, or an index tag sequence, or a combination thereof. A universal sequence is a region of nucleotide sequence that is common to two or more nucleic acid fragments. Optionally, the two or more nucleic acid fragments also have regions of sequence differences. A universal sequence that may be present in different members of a plurality of nucleic acid fragments can allow for the replication or amplification of multiple different sequences using a single universal primer that is complementary to the universal sequence.

Figure 4A:
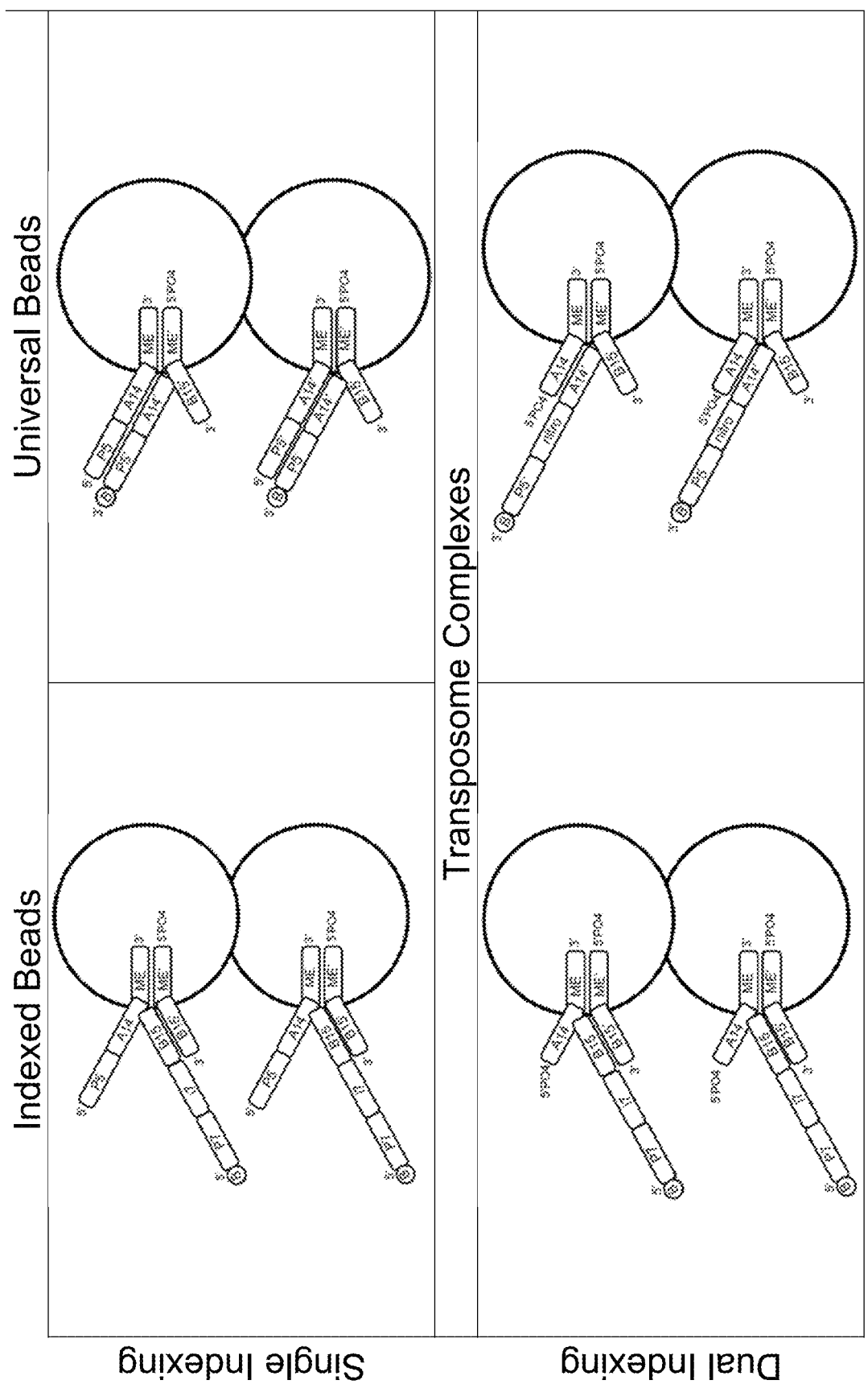
FIGS. 4A-4E illustrate a schematic diagram comparing various configurations of the transposome complex immobilized to a solid support via an exemplary biotin (B, solid support not shown), including indexed beads and universal beads, each shown in both single indexing and dual indexing modes, for embodiments of methods of generating a library of tagged nucleic acid fragments without using PCR amplification, using variations of transposome complexes, wherein components of the transposons and/or attachment polynucleotides are altered, arranged, or varied in comparison to one another.

In some embodiments, the first transposon further comprises a primer sequence 5' of the 5' adaptor sequence, and the attachment polynucleotide comprises (i) a portion complementary with and hybridized to the 5' adaptor sequence and (ii) a complementary primer sequence (see, e.g., FIG. 4A, single index, universal beads). Such constructs are useful as universal beads for single indexing applications as there is no index tag sequence employed.

In some embodiments, the first transposon further comprises a primer sequence 5' of the 5' adaptor sequence, and the attachment polynucleotide comprises an index tag sequence and a primer sequence (see, e.g., FIG. 4A, single indexing, indexed beads).

In some embodiments, the first transposon comprises the 5' adaptor sequence, and the attachment polynucleotide comprises (i) a portion complementary with and hybridized to the 5' adaptor sequence, (ii) a spacer region, and (iii) a primer sequence (see, e.g., FIG. 4A, universal beads, dual indexing).

In some embodiments, the second transposon comprises the 3' adaptor sequence and the attachment polynucleotide comprises (i) a portion complementary to and hybridized with the 3' adaptor sequence, (ii) an index tag sequence, and (iii) a primer sequence (see, e.g., FIG. 4A, dual indexing, indexed beads).

Figure 3A:
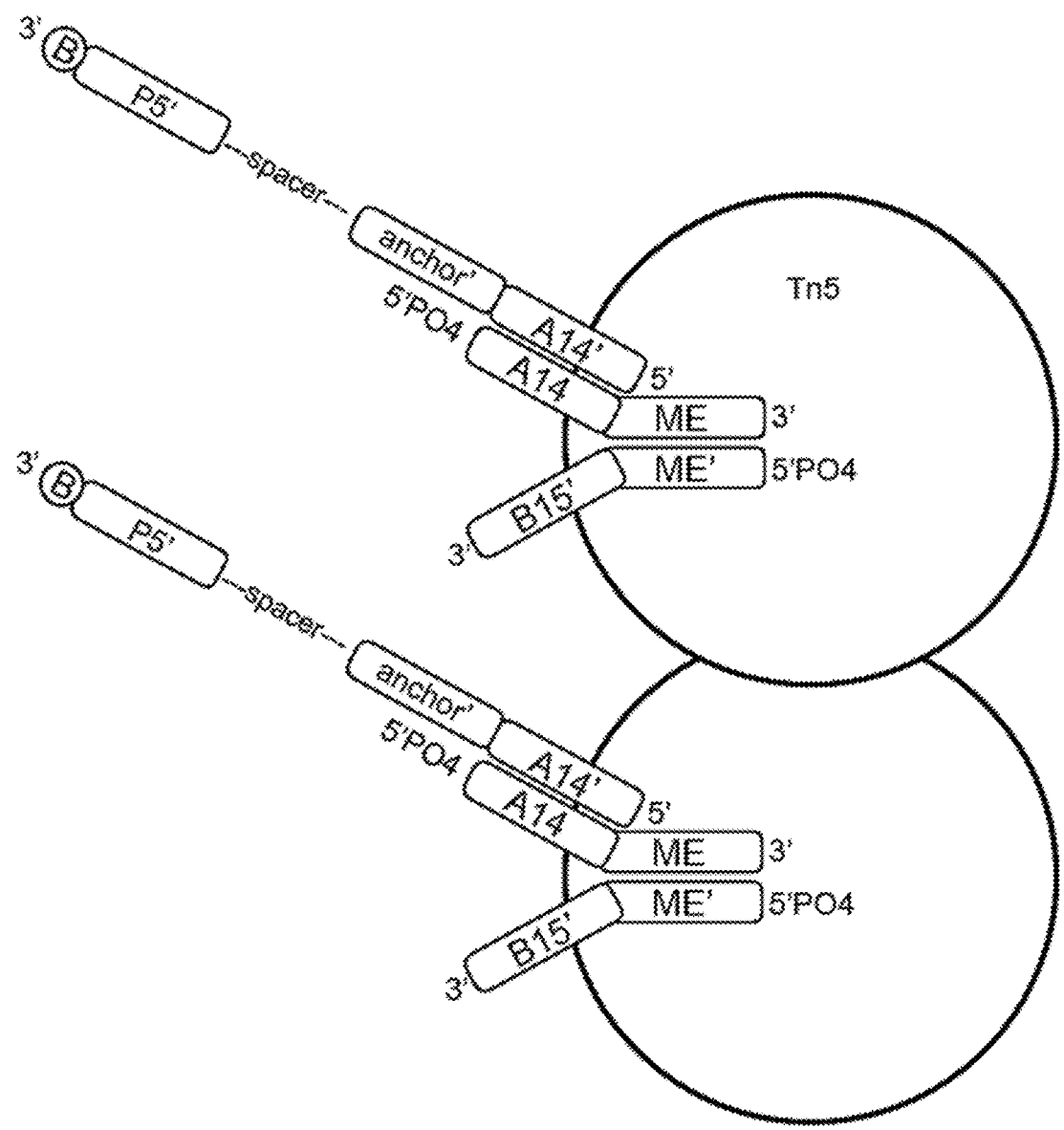
FIGS. 3A-3C illustrate exemplary steps of a method of generating a library of tagged nucleic acid fragments without using PCR amplification.
Figure 3B:
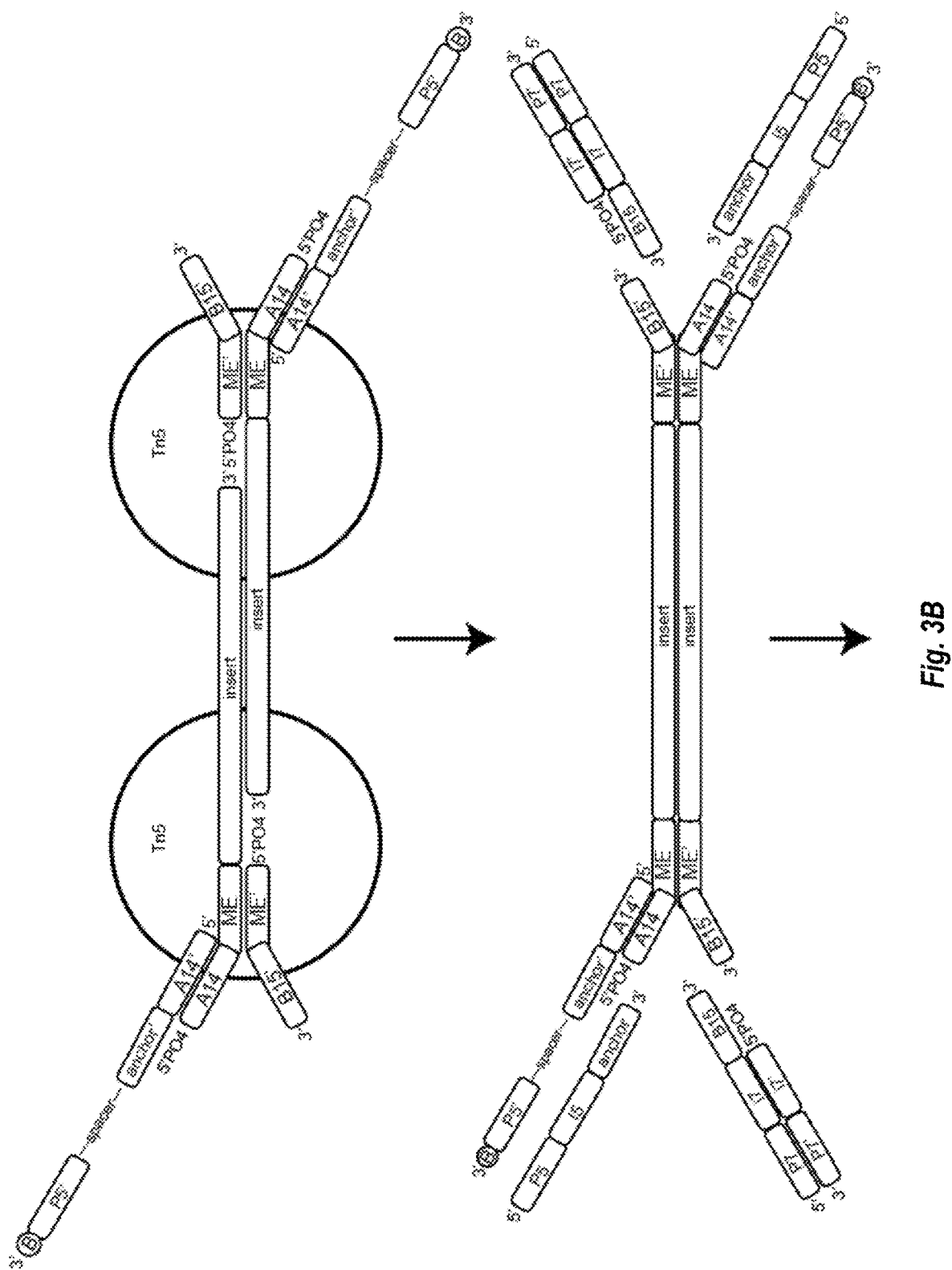
Figure 3C:
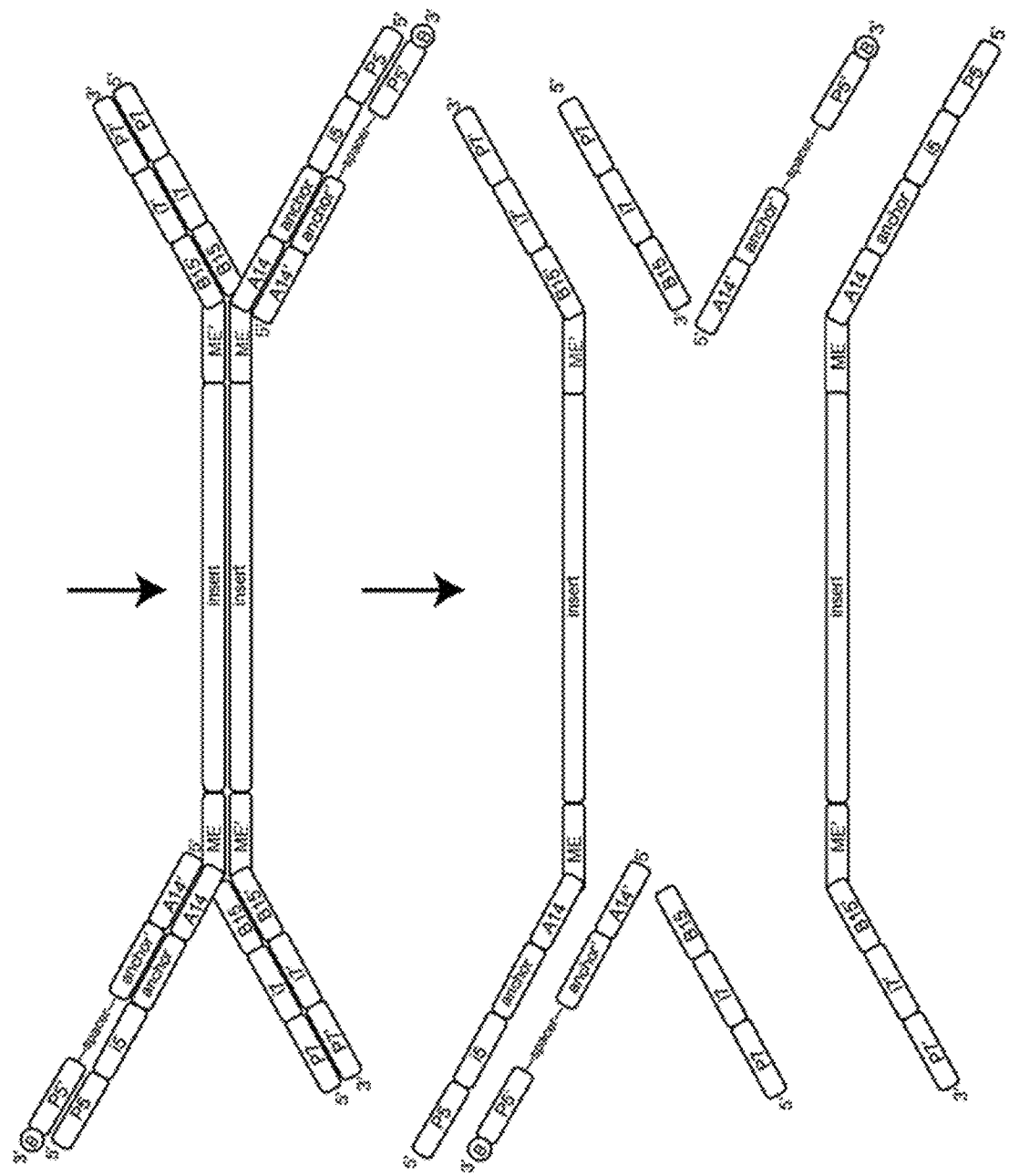

In some embodiments, the attachment polynucleotide comprises a spacer region (see, e.g., FIG. 4A) or a spacer region and an anchor region (see, e.g., FIG. 3). As used herein, a spacer region is a sequence refers a nucleic acid sequence not carrying any structural or codifying information for known gene functions. The spacer region on the attachment polynucleotide is capable of aligning with indexing oligonucleotides with varied sequences (e.g., with a range of i5 sequences). In some embodiments, the spacer region is a universal sequence. In some embodiments, the spacer region is a non-DNA spacer. In some embodiments, the spacer region includes universal bases, such as inosines or nitroindoles. In some embodiments, the spacer includes a sp18 linker. A sp18 linker, as used herein, is a standard modification linker having C18 spacers (an 18-atom hexaethylene glycol spacer), and is equivalent to 4 base pairs in length. Thus, a 2×sp18 linker is equivalent to 8 base pairs in length. In some embodiments, the spacer region comprises a 2×sp18 synthetic linker. In some embodiments, the spacer region comprises one or more C18 spacers, such as 1, 2, 3, 4, 5, 6, or more C18 spacers. In some embodiments, the spacer region comprises two C18 spacers (which are equivalent in length to 8 nucleotides). In some embodiments, the spacer is a C9 spacer equivalent in length to 2 base pairs. In some embodiments, the spacer region comprises one or more C9 spacers (triethyleneglycol spacer), such as 1, 2, 3, 4, 5, 6, or more C9 spacers. In some embodiments, the spacer is a conventional spacer used with existing indices, such as a 10 base pair spacer. In some embodiments, the spacer region is a combination of spacers, for example, a combination of one or more C18 spacers and one or more C9 spacers, or any combination of any spacer described herein. In some embodiments, the spacer region is a length equivalent to 2, 3, 4, 5, 6, 7, 8, 9, 10, 12, 15, 20, or 30 base pairs. In some embodiments, the spacer region is a length approximately equivalent to 8 or 10 base pairs or nucleotides. In some embodiments, the spacer region is specifically chosen to be the same length as the index region. In some embodiments, the index regions are 8 nucleotides long, and the spacer region comprises two C18 spacers. In some embodiments, the index regions are 10 nucleotides long and the spacer region comprises two C18 spacers and one C9 spacer.

In some aspects, the attachment polynucleotide comprises an anchor sequence. In some embodiments, the anchor sequence is GGATATGCTCGG (SEQ ID NO: 22). In some embodiments, the anchor sequence is an A14 sequence (SEQ ID NO: 4). As used herein, an anchor region means a DNA sequence that is complementary to an anchor complement region in an indexing oligonucleotide and enables hybridization of the two components (see, e.g., FIG. 3B). In some aspects, the anchor region is complementary to a portion of an anchor complement region of an indexing oligonucleotide, where the indexing oligonucleotide comprises the anchor region complement and an index tag sequence (-Anchor'-Index Tag Sequence-). In some embodiments, the anchor sequence is complementary to an anchor complement region common to a plurality of indexing oligonucleotides. In some embodiments, each index tag sequence in a plurality of indexing oligonucleotides is the same (no indexing) or different (indexing). In some embodiments, the index tag sequence is an i5 sequence. The attachment polynucleotide may further include additional sequence elements or components for improving efficiency and functionality of the attachment polynucleotide for binding to indices, including, for example, primer sequences, anchor sequences, universal sequences, spacer regions, index sequences, capture sequences, barcode sequences, cleavage sequences, sequencing-related sequences, and combinations thereof. In some embodiments, the attachment polynucleotide comprises an A14' sequence.

Variations of the transposome complex, including the transposase, the transposons, and the attachment polynucleotide may be realized. For example, variations in configuration, design, hybridization, structural elements, and overall arrangement of the transposome complex may be realized. The disclosure and drawings provided herein provide several variations, but it is understood that additional variations within the scope of the disclosure may be readily realized.

Solid Support

The terms "solid surface," "solid support," and other grammatical equivalents refer to any material that is appropriate for or can be modified to be appropriate for the attachment of the transposome complexes. As will be appreciated by those in the art, the number of possible substrates is multitude. Possible substrates include, but are not limited to, glass and modified or functionalized glass, plastics (including acrylics, polystyrene and copolymers of styrene and other materials, polypropylene, polyethylene, polybutylene, polyurethanes, TEFLON, etc.), polysaccharides, polyhedral organic silsesquioxane (POSS) materials, nylon or nitrocellulose, ceramics, resins, silica, or silica-based materials including silicon and modified silicon, carbon, metals, inorganic glasses, plastics, optical fiber bundles, beads, paramagnetic beads, and a variety of other polymers.

Suitable bead compositions include, but are not limited to, plastics, ceramics, glass, polystyrene, methylstyrene, acrylic polymers, paramagnetic materials, thoria sol, carbon graphite, titanium dioxide, latex or cross-linked dextran such as Sepharose, cellulose, nylon, cross-linked micelles and TEFLON, as well as any other materials outlined herein for solid supports. In certain embodiments, the microspheres are magnetic microspheres or beads, for example paramagnetic particles, spheres or beads. The beads need not be spherical; irregular particles may be used. Alternatively or additionally, the beads may be porous. The bead sizes range from nanometers, e.g., 100 nm, to millimeters, e.g., 1 mm, with beads from about 0.2 micron to about 200 microns being preferred, and from about 0.5 to about 5 micron being particularly preferred, although in some embodiments smaller or larger beads may be used. The bead may be coated with a binding partner, for example the bead may be streptavidin coated. In some embodiments, the beads are streptavidin coated paramagnetic beads, for example, Dynabeads MyOne streptavidin C1 beads (Thermo Scientific catalog #65601), Streptavidin MagneSphere Paramagnetic particles (Promega catalog #Z5481), Streptavidin Magnetic beads (NEB catalog #S1420S) and MaxBead Streptavidin (Abnova catalog #U0087). The solid support could also be a slide, for example a flowcell or other slide that has been modified such that the transposome complex can be immobilized thereon.

In some embodiments, the binding partner is present on the solid support or bead at a density of from 1000 to about 6000 pmol/mg, or about 2000 to about 5000 pmol/mg, or about 3000 to about 5000 pmol/mg, or about 3500 to about 4500 pmol/mg.

In one embodiment, the solid surface is the inner surface of a sample tube. In another embodiment, the solid surface is a capture membrane. In one example, the capture membrane is a biotin-capture membrane (for example, available from Promega Corporation). In another example, the capture membrane is filter paper. In some embodiments of the present disclosure, solid supports comprised of an inert substrate or matrix (e.g. glass slides, polymer beads etc.) which has been functionalized, for example by application of a layer or coating of an intermediate material comprising reactive groups which permit covalent attachment to molecules, such as polynucleotides. Examples of such supports include, but are not limited to, polyacrylamide hydrogels supported on an inert substrate such as glass, particularly polyacrylamide hydrogels as described in WO2005/065814 and US2008/0280773, the contents of which are incorporated herein in their entirety by reference. The methods of tagmenting (fragmenting and tagging) DNA on a solid surface for the construction of a tagmented DNA library are described in WO2016/189331 and US2014/0093916A1, which are incorporated herein by reference in their entireties. In some embodiments, the transposome complex described herein is immobilized to a solid support via the binding element. In some such embodiments, the solid support comprises streptavidin as the binding partner and the binding element is biotin.

In some embodiments, transposome complexes are immobilized on a solid support, such as a bead, at a particular density or density range. In some embodiments, the density of complexes on a solid support refers to the concentration of transposome complexes in solution during the immobilization reaction. The complex density assumes that the immobilization reaction is quantitative. Once the complexes are formed at a particular density, that density remains constant for the batch of surface-bound transposome complexes. The resulting beads can be diluted, and the resulting concentration of complexes in the diluted solution is the prepared density for the beads divided by the dilution factor. Diluted bead stocks retain the complex density from their preparation, but the complexes are present at a lower concentration in the diluted solution. The dilution step does not change the density of complexes on the beads, and therefore affects library yield but not insert (fragment) size. In some embodiments, the density is between about 5 nM and about 1000 nM, or between about 5 and 150 nM, or between about 10 nM and 800 nM. In other embodiments, the density is about 10 nM, or about 25 nM, or about 50 nM, or about 100 nM, or about 200 nM, or about 300 nM, or about 400 nM, or about 500 nM, or about 600 nM, or about 700 nM, or about 800 nM, or about 900 nM, or about 1000 nM. In some embodiments, the density is about 100 nM. In some embodiments, the density is about 300 nM. In some embodiments, the density is about 600 nM. In some embodiments, the density is about 800 nM. In some embodiments, the density is about 100 nM. In some embodiments, the density is about 1000 nM.

Some embodiments provided herein relate to a kit including a transposome complex, as described herein, and an index mix comprising index sequences. Some embodiments provided herein relate to a kit including a composition having a solid support with a transposome complex immobilized thereon, as described herein, and an index mix comprising index sequences. In some embodiments, the index mix comprises i5 index sequences and i7 index sequences, wherein the i5 index sequences are complementary to and hybridize to the attachment polynucleotide, and wherein the i7 index sequences are complementary to and hybridize to the 3' adaptor sequence.

Immobilized Transposome Complexes/Methods of Generating Tagged Nucleic Acid Fragments The disclosure further provides methods of preparing immobilized transposome complexes as described herein. Some embodiments provided herein relate to a method of generating a library of tagged nucleic acid fragments. In some embodiments, the method includes providing a solid support having a transposome complex immobilized thereon, applying a target nucleic acid to the solid support under conditions sufficient to fragment the target nucleic acid into a plurality of target fragments, and to join the 3' end of the first transposon to the 5' ends of the target fragments to produce a plurality of 5' tagged target fragments, and applying an index mix comprising index sequences to activate the library for sequencing. In some embodiments, the transposome complex includes a transposase bound to a first and a second transposon, a first transposon comprising a 3' transposon end sequence and a 5' adaptor sequence, an attachment polynucleotide comprising an attachment adaptor sequence and a binding element, and a second transposon comprising a 5' transposon end sequence and a 3' adaptor sequence.

In some embodiments, a method comprises generating a library of tagged nucleic acid fragments comprising contacting an immobilized transposome complex with a target nucleic acid under conditions sufficient to fragment the target nucleic acid into a plurality of target fragments, and to join the 3' end of the first transposon to the 5' ends of the target fragments to produce a plurality of 5' tagged target fragments.

In some aspects, the method further comprises: treating the solid support to remove unbound nucleic acids; or treating the solid support to remove the transposase from the complex, optionally by (a) heating the solid support and/or (b) washing the solid support with an enzyme denaturing agent, wherein the enzyme denaturing agent optionally comprises sodium dodecyl sulfate (SDS), guanidine hydrochloride, urea, or proteinase.

In some embodiments, the contacting comprises adding a biological sample to the transposome complex. In some embodiments, the biological sample comprises a cell lysate or whole cells, or is selected from blood, plasma, serum, lymph, mucus, sputum, urine, semen, cerebrospinal fluid, bronchial aspirate, feces, macerated tissue, and fixed tissue FFPE.

In some aspects, the contacting further comprises hybridizing a plurality of indexing oligonucleotides to the attachment polynucleotides, wherein the plurality of indexing oligonucleotides comprise the same or different index sequences.

In some aspects the method further comprises treating the plurality of 5' tagged target fragments with a polymerase and a ligase to extend and ligate the strands to produce fully double-stranded tagged fragments. In some aspects, the treating with a polymerase and a ligase is done in the presence of a DNA secondary structure disruptor, wherein the disruptor is optionally DMSO. In some aspects, the treating with a polymerase and a ligase is done in the presence of an oligonucleotide that is a complement of the primer sequence, wherein the oligonucleotide is a P7' oligonucleotide, and wherein the primer sequence is a P7 sequence. In some embodiments, the polymerase comprises a T4 DNA polymerase mutant lacking exonuclease activity.

In some aspects, the method further comprises removing the fully double-stranded tagged fragments from the solid support. In some aspects, the removing comprises applying heat and/or a denaturant sufficient to cleave the fully double-stranded tagged fragments from the solid support.

In some aspects, the method further comprising sequencing one or more of the 5' tagged target fragments or fully double-stranded tagged fragments. In some aspects, the fragments are not quantified by PCR after the contacting and before the sequencing. In some aspects, the nucleic acid is DNA or RNA. In some aspects, the 3' adaptor sequence is complementary to at least a portion of an index adaptor sequence. In some aspects, the primer sequence of the attachment polynucleotide is complementary to at least a portion of an index primer sequence. In some aspects, the primer sequence of the attachment polynucleotide is complementary to an index primer sequence of the indexing polynucleotide.

In some embodiments, the method further includes washing the solid support to remove unbound nucleic acids. In some embodiments, the method further includes treating the solid support to remove transposase. In some embodiments, treating the solid support includes washing the solid support with an enzyme denaturing agent. In some embodiments, the enzyme denaturing agent includes acetic acid, dimethyl sulfoxide (DMSO), dithiothreitol, ethanol, formaldehyde, formamide, glutaraldehyde, guanidine hydrochloride, lithium perchlorate, mercaptoethanol, propylene glycol, proteinase, sodium bicarbonate, sodium dodecyl sulfate (SDS), sodium salicylate, sulfosalicylic acid, trichloroacetic acid, tris(2-carboxyethyl)phosphine) (TCEP), or urea. In some embodiments, treating the solid support includes heating the solid support to remove transposase. In some embodiments, applying a target nucleic acid includes mixing a biological sample with the transposome complex. The nucleic acid need not be completely purified or purified at all, and can be part of a biological sample or a mixture with protein, other nucleic acid species, other cellular components, and/or any other contaminants. In some embodiments, the biological sample includes a cell lysate. In some embodiments, the biological sample includes whole cells. In some embodiments, the biological sample is selected from a bodily fluid, blood, plasma, serum, lymph, mucus, sputum, urine, semen, cerebrospinal fluid, bronchial aspirate, feces, macerated tissue, and fixed tissue formalin-fixed paraffin-embedded tissue (FFPE).

In some embodiments, applying the index mix includes hybridizing an index sequence to the attachment polynucleotide and to the second transposon. In some embodiments, the index mix comprises an extension-ligation mix (ELM). In some embodiments, the ELM comprises a polymerase and a ligase. In some embodiments, the ELM is a split ELM for separation ligation of indices. In some embodiments, the polymerase comprises T4 DNA polymerase or a mutant thereof (such as a T4 DNA polymerase lacking exonuclease activity, or a mutant T4 DNA polymerase, or a mutant T4 DNA polymerase lacking exonuclease activity). In some embodiments, the ligase comprises E. coli DNA ligase. In some embodiments, the extension-ligation reaction is done in the presence of a DNA secondary structure disruptor, such as DMSO. In some embodiments, the method further includes denaturing the plurality of 5' tagged target fragments from the solid support. In some embodiments, denaturing may be achieved by applying heat and/or a denaturant sufficient to cleave the 5' tagged target fragments from the solid support. In some embodiments, the method further includes sequencing one or more of the 5' tagged target fragments or ligation products thereof. In some embodiments, the nucleic acid is DNA or RNA.

In some aspects, such methods include contacting the first and second transposons as described herein with an attachment polynucleotide bound to a surface under conditions suitable for hybridizing the attachment polynucleotide to the first or second transposon. In some aspects, methods for preparing a solid support-bound transposome complex comprise incubating a transposome complex as described herein with a solid support comprising a binding partner under conditions sufficient for the binding element to bind (covalently or non-covalently) with the binding partner. The immobilized hybridized polynucleotide that includes the attachment polynucleotide and the first and second transposons is then contacted with transposase under conditions suitable for forming a transposome complex.

In some embodiments, the first and second transposons as described herein are annealed to each other, and the first transposon is annealed to the attachment polynucleotide. The annealed polynucleotides are then loaded onto a transposase, such as a Tn5 transposase, thereby forming a transposome complex, which is then contacted with and bound to a solid support, such as a bead. In some embodiments, the annealed transposons are bound to a solid support such as a bead and a transposase is then complexed with the transposons, thereby creating a transposome that is bound to a solid support.

In some aspects, methods are provided for preparing fragments from a target nucleic acid, the method comprising providing a solid support comprising a transposome complex immobilized thereon as described herein; applying a target nucleic acid to the solid support under conditions sufficient to fragment the target nucleic acid into a plurality of target fragments, and to join the 3' end of the first transposon to the 5' ends of the target fragments to produce a plurality of 5' tagged target fragments. In some aspects, the method further includes applying an index mix including index sequences. In some embodiments, the fragment condition is a condition suitable for tagmentation by using the transposome complex to fragment and tag the target nucleic acid.

In some embodiments of the methods described herein, following the fragmenting and tagging, the methods further include washing the solid support to remove unbound nucleic acids. In some embodiments of the methods described herein, following the fragmenting and tagging, the methods further include removing the transposase. Removal of the transposase may be accomplished under chemical conditions, such as, washing the solid support with an agent to remove the transposase. In some embodiments, the agent is sodium dodecyl sulfate (SDS).

In some embodiments, the method further includes contacting the solid support with an index mix. Contacting with an index mix serves to tag the fragments with a particular index and to activate the library for sequencing. In some embodiments, the index mix includes oligonucleotides that hybridize to the transposon or the attachment polynucleotide to tag or index the nucleic acid fragments. Thus, for example, the oligonucleotide includes an index and other regions of the oligonucleotide are complementary to the transposon or attachment polynucleotide and hybridizes thereto. By way of example, in one embodiment, an i5 index having a primer sequence (P5 sequence), an index sequence (i5 sequence), and an anchor sequence hybridizes to the attachment polynucleotide at complementary sequences, such that P5 hybridizes to P5', and anchor hybridizes to anchor'. In some embodiments, the i5 sequence binds to a nitroindol (nitro) sequence of the attachment polynucleotide. In some embodiments, a nitroindol sequence is complementary to and hybridizes to any i5 index sequence. In one embodiment, an i7 index having a primer sequence (P7), an index sequence (i7), and an adaptor sequence (B15 sequence) hybridizes to the second transposon at complementary sequences, such that the P7 hybridizes to P7', the i7 hybridizes to i7', and B15 hybridizes to B15'. In some embodiments, the index mix includes a double stranded index. After contacting the solid support with the index mix, the fragments are ligated and extended using an extension and ligation mix (ELM). An ELM may include, for example a T4 DNA polymerase and an *E. coli* DNA ligase. Exemplary polymerases include, but are not limited to, the Bst large fragments of Bst DNA polymerase I, *E. coli* DNA polymerase I (Klenow fragment), Klenow fragment (3'-5' exo-), T4 DNA polymerase, T7 DNA polymerase, Deep VentR. (exo-) DNA Polymerase, Deep VentR DNA Polymerase, Terminator II DNA Polymerase, AmpliTherm DNA Polymerase, SP6 DNA polymerase, or Taq polymerase, or mutants, analogues, or derivatives of any of the aforementioned polymerases. Exemplary ligases include, but are not limited to T4 DNA ligase, T4 RNA ligase, Taq DNA ligase, *E. Coli* DNA ligase, Pfu DNA ligase and Tth DNA ligase. In some embodiments, the ELM is a split ELM reaction to allow for index ligation and index extension of difference indices, for example, to allow for separate i5 ligation and i7 extension. The solid support is then treated with an agent to denature the strand sequences, such as with NaOH, thereby generating tagged nucleic acid fragments.

In some embodiments, the fragments are deposited on a flow cell. In some embodiments, the fragments are hybridized to complementary primers grafted to the flow cell or surface. In some embodiments, the sequences of the sequencing fragments are detected by array sequencing or next-generation sequencing methods, such as sequencing-by-synthesis.

Table 1 depicts exemplary sequences used in the transposome complexes for generating the library of tagged nucleic acid fragments.

TABLE 1

Exemplary Sequences

| Oligo-nucleotide name | Design | Function | Sequence (SEQ ID NO) |
|---|---|---|---|
| P5_A14_ME | Single indexing, indexed and universal beads | 5' transposon arm | AATGATACGGCGACCA CCGAGATCTACACTCG TCGGCAGCGTCAGATG TGTATAAGAGACAG (SEQ ID NO: 9) |
| P_ME'_B15' | All designs involving i7 indexing | 3' transposon arm | /5Phos/CTGTCTCTTATA CACATCTCCGAGCCCA CGAGAC (SEQ ID NO: 10) |
| Bio_P7_i701_B15_ddC | i701 indexed beads, single or dual indexing | Attachment oligo | /5Biosg/CAAGCAGAAGA CGGCATACGAGATTCG CCTTAGTCTCGTGGGCT CGG/3ddC/ (SEQ ID NO: 11) |
| A14'_P5'_bio | Universal beads, single indexing | Attachment oligo | GACGCTGCCGACGAGT GTAGATCTCGGTGGTC GCCGTATCATT/3Bio/ (SEQ ID NO: 12) |
| P_A14_ME | Suitable for dual indexing | 5' transposon arm | /5Phos/TCGTCGGCAGCG TCAGATGTGTATAAGA GACAG (SEQ ID NO: 13) |
| A14'_nitro_P5'_bio | Nitroindole universal design | Attachment oligo | GACGCTGCCGACGACC C/i5NitInd//i5NitInd// i5NitInd//i5NitInd// i5NitInd//i5NitInd// i5NitInd//i5NitInd/ GTGTAGATCTCGGTGGTC GCCGTATCATT/3Bio/ (SEQ ID NO: 14) |
| A14'12anc'_2sp_p5'_bio | Anchor and spacer universal design | Attachment oligo | GACGCTGCCGACGACC GAGCATATCC/iSp18// iSp18/GTGTAGATCTCGGTG GTCGCCGTATCATT/ 3BioTEG/(SEQ ID NO: 15) |

TABLE 1-continued

Exemplary Sequences

| Oligo-nucleotide name | Design | Function | Sequence (SEQ ID NO) |
|---|---|---|---|
| P5_i501 | For use with nitroindole design | i501 indexing oligo | AATGATACGGCGACCACCGAGATCTACACTAGATCGC (SEQ ID NO: 16) |
| P_i701'_P7'_ddC | Part of double-stranded i7 adaptor, can be used with several bead designs | i701 indexing oligo | /5Phos/TAAGGCGAATCTCGTATGCCGTCTTCTGCTTG/3ddC/ (SEQ ID NO: 17) |
| P7_i701_B15_ddC | Part of double-stranded i7 adaptor, can be used with several bead designs | i701 indexing oligo | CAAGCAGAAGACGGCATACGAGATTCGCCTTAGTCTCGTGGGCTCGG/3ddC/ (SEQ ID NO: 18) |
| P5_i501_12anc | For use with anchor and spacer attachment oligo | i501 indexing oligo | AATGATACGGCGACCACCGAGATCTACACTAGATCGCGGATATGCTCGG (SEQ ID NO: 19) |

In some aspects, methods of generating a library of tagged nucleic acid fragments comprise contacting an immobilized transposome complex with a target nucleic acid under conditions sufficient to fragment the target nucleic acid into a plurality of target fragments, and to join the 3' end of the first transposon to the 5' ends of the target fragments to produce a plurality of 5' tagged target fragments; treating the solid support to remove unbound nucleic acids; or treating the solid support to remove the transposase from the complex, optionally by (a) heating the solid support and/or (b) washing the solid support with an enzyme denaturing agent, wherein the enzyme denaturing agent optionally comprises sodium dodecyl sulfate (SDS), guanidine hydrochloride, urea, or proteinase; treating the plurality of 5' tagged target fragments with a polymerase and a ligase to extend and ligate the 5' tagged target fragments to produce fully double-stranded tagged fragments, optionally wherein the treating with a polymerase and a ligase is done in the presence of a DNA secondary structure disruptor, wherein the disruptor is optionally DMSO; removing the fully double-stranded tagged fragments from the solid support, optionally wherein the removing comprises applying heat and/or a denaturant sufficient to cleave the fully double-stranded tagged fragments from the solid support, optionally wherein the denaturant is NaOH; and selecting the fully double-stranded tagged fragments using capture beads, optionally wherein the capture beads are magnetic beads, further optionally wherein two separate selecting steps are performed.

In some embodiments, the immobilized transposome complex comprises a solid support; and a transposome complex immobilized to the solid support, wherein the transposome complex comprises a transposase; a first transposon comprising a 3' transposon end sequence and an anchor sequence (Anchor); a second transposon comprising a 5' transposon end sequence and a B15' sequence; and an attachment polynucleotide comprising an anchor sequence complement (Anchor'), an A14' sequence, a spacer, and a P5' sequence and a binding element comprising biotin, wherein the biotin is immobilized to the solid support. In some embodiments, a method further comprises sequencing one or more of the fully double-stranded tagged fragments.

Methods of Generating Tagged Nucleic Acid Fragments Through Combined Tagmentation and Indexing In some embodiments, dual-indexed paired-end libraries may be prepared from a DNA sample using a combined tagmentation and indexing step. By avoiding separate tagmentation and indexing steps, this protocol has the advantage of ease-of-use and shorter duration. Further, this protocol can avoid a denaturation step and produce double-stranded libraries without the need for a separate step to produce double-stranded samples from denatured single-stranded samples. This protocol can also avoid certain washing steps, further reducing the time required for the workflow.

This method uses a first immobilized transposon complex and a second immobilized transposon complex. In the first immobilized transposon complex, sequence X in the first transposon is an anchor sequence, and sequence X' in the attachment polynucleotide is an anchor sequence complement. In the second immobilized transposon complex, sequence X in the first transposon is an anchor sequence, and sequence X' in the attachment polynucleotide is an anchor sequence complement. The anchor sequences of the first and second immobilized transposon complexes may be non-complementary to avoid cross-hybridization. The first transposon complex may comprise an exemplary first attachment polynucleotide comprising (i) an anchor sequence complement, an A14' sequence, a spacer, and a P5' sequence, and (ii) a binding element comprising biotin, and the second transposon complex may comprise an exemplary second attachment polynucleotide comprising (i) an anchor sequence complement, a B15' sequence, a spacer, and a P7' sequence, and (ii) a binding element comprising biotin.

In combined tagmentation and indexing a suspension of solid support-linked transposomes (BLTs, i.e., the immobilized transposon complexes) comprising the first and second transposome complexes may be added to each well. An indexing step may then be performed in a single reaction solution with Index 1 (i7) adapters, Index 2 (i5) adapters, and sequences required for sequencing cluster generation ligated in the same reaction solution as the tagmentation. The first indexing oligonucleotides may comprise a A14 sequence, i5 sequence, and P5 sequence, and second indexing oligonucleotides may comprise a B15 sequence, i7 sequence, and P7 sequence. Conditions for the tagmentation/ligation step include tagmentation buffer and *E. Coli* DNA ligase added to the mixture of target DNA, first and second transposome complexes, and the first and second indexing oligonucleotides. This combined tagmentation and indexing step may proceed for various times, such as from at least 1 minute to at least 15 minutes, or from at least 5 minutes to at least 15 minutes.

The tagmentation and indexing reactions may then be stopped using a variety of methods, including heating the solid support and/or washing the solid support with an enzyme denaturing agent, such as optionally using sodium dodecyl sulfate (SDS), guanidine hydrochloride, urea, or proteinase. The time for stopping the reaction, whether by heating and/or through a washing step, may vary from at least 1 minute to at least 5 minutes.

The 5' tagged target fragments ligated to indexing oligonucleotides may be treated with a polymerase to extend and produce fully double-stranded tagged fragments. The extension reaction may proceed for various times, such as from at least 1 minute to at least 10 minutes, or from at least 2 minutes to at least 10 minutes.

Further, library preparation comprising combined tagmentation and indexing may also avoid a qPCR step, as the final product is a double-stranded DNA library in solution.

In some embodiments, the contacting a first immobilized transposome complex and a second immobilized transposome complex and the treating the plurality of 5' tagged target fragments with a ligase are performed in a single reaction.

In some embodiments, the double-stranded tagged fragments are produced in solution.

Some embodiments further comprise selecting the fully double-stranded tagged fragments using capture beads, optionally wherein the capture beads are magnetic beads, further optionally wherein two separate selecting steps are performed.

In some embodiments, the method further comprises sequencing one or more of the fully double-stranded tagged fragments.

Target Nucleic Acid

The target nucleic acid can be any type that comprises DNA, RNA, cDNA, or the like. For example, the target nucleic acid may be in a variety of states of purification, including purified nucleic acid. In some embodiments, the biological sample comprises a mixture of nucleic acids (such as DNA), protein, other nucleic acid species, other cellular components, and/or any other contaminant, present in approximately the same proportion as found in vivo. For example, in some embodiments, the components are found in the same proportion as found in an intact cell. Because the methods provided herein allow nucleic acid or DNA to be bound to a solid support through the tagmentation process, other contaminants can be removed by washing the solid support after tagmentation occurs. The biological sample can comprise, for example, a crude cell lysate or whole cells. For example, a crude cell lysate that is applied to a solid support in a method set forth herein, need not have been subjected to one or more of the separation steps that are traditionally used to isolate nucleic acids from other cellular components.

Thus, in some embodiments, the biological sample can comprise not only purified nucleic acids from any source but also, for example, unpurified nucleic acids as found in blood, plasma, serum, lymph, mucus, sputum, urine, semen, cerebrospinal fluid, bronchial aspirate, feces, and macerated tissue, or a lysate thereof, or any other biological specimen comprising nucleic acid or DNA material. Target nucleic acid may be from a tissue sample, tumor sample, cancer cells, or a biopsy sample. The target nucleic acid may be cell-free DNA (cfDNA).

Target nucleic acid may come from any species, of from a mixture of species. For example, target nucleic acid may be from a mammal (such as a human, dog, cat, cow, pig, sheep, or other domesticated animal), or other species such as fish, bacteria, virus, fungus, or archaea. Nucleic acid may come from environmental samples, such as soil or water.

In some embodiments, the target nucleic acid is DNA. In one such embodiment, the DNA is double-stranded. In some further embodiments, the double-stranded DNA comprises genomic DNA. In some other embodiments, the target nucleic acid is RNA or a derivative thereof, or cDNA. In some embodiments, the target nucleic acid is a product of an upstream reaction, such as an amplification or replication event, for example, an amplicon. In some embodiments, the target nucleic acid is bisulfite treated DNA.

In some embodiments, a biological sample (raw sample or extract) is processed to purify target nucleic acids prior to the tagmentation methods described herein. In some embodiments, the biological sample is a raw sample or a raw sample lysate (e.g., blood, saliva, cell or cells). In some embodiments, the treatment method comprises providing a raw sample, raw sample lysate, or pre-processed sample (e.g., a blood or saliva sample), mixing the sample with a lysis buffer and proteinase K, incubating the mixture to lyse cells in the sample and release DNA from the cells, thereby provided target nucleic acid(s) for the tagmentation methods described herein. An amount of biological sample is not specifically required, so long as the biological sample contains sufficient nucleic acids for analysis. Thus, an amount of biological sample may include from about 1 µL to about 500 µL, such as 1, 2, 3, 4, 5, 6, 7, 8, 9, 10, 15, 20, 25, 30, 35, 40, 45, 50, 60, 70, 80, 90, 100, 150, 200, 250, 300, 350, 400, 450, or 500 µL, or an amount within a range defined by any two of the aforementioned values.

Components in raw samples or raw sample lysates such as blood, or additives in pre-processed samples such as saliva that has been collected in an Oragene collection tube (stabilization agents in collection tubes), may inhibit tagmentation reactions. Thus, provided herein is a method for treating a raw sample, raw sample lysate, or pre-processed sample to overcome this problem. In some embodiments, the method comprises providing a raw sample, raw sample lysate, or pre-processed sample (e.g., a blood or saliva sample), mixing the sample with a lysis buffer, proteinase K, and DNA capture or purification beads (e.g., SPRI beads, beads comprising carboxyl groups, where the beads are optionally magnetic beads), incubating the mixture to lyse cells in the sample and release DNA from the cells, thereby capturing the DNA on the DNA purification or SPRI beads, and separating the beads comprising the captured DNA from the mixture. The separating serves to remove potential tagmentation inhibitors present in the supernatant. The method further comprises optionally washing the beads comprising the captured DNA, and eluting the DNA from the beads to provide target nucleic acid(s).

In some embodiments, the target nucleic acid is present in an amount sufficient for generating a library for sequencing. In some embodiments, a quantity of target nucleic acid is an amount of gDNA of 10-500 ng, such as 10, 20, 30, 40, 50, 60, 70, 80, 90, 100, 200, 300, 400, or 500 ng, or an amount within a range defined by any two of the aforementioned values. In some embodiments, a target nucleic acid is a gDNA present in an amount of 50 ng.

Methods of Sequencing

Some of the methods provided herein include methods of analyzing nucleic acids. Such methods include preparing a library of template nucleic acids of a target nucleic acid, obtaining sequence data from the library of template nucleic acids, and optionally assembling a sequence representation of the target nucleic acid. The DNA fragments produced by transposome mediated tagmentation can be sequenced according to any suitable sequencing methodology, such as direct sequencing or next generation sequencing, including sequencing by synthesis, sequencing by ligation, sequencing by hybridization, sequencing based on detection of released protons can use an electrical detector and associated techniques that are commercially available from Ion Torrent (Guilford, Conn., a Life Technologies subsidiary), nanopore sequencing and the like. In some embodiments, the DNA fragments are sequenced on a solid support, such as a flow cell. Exemplary SBS procedures, fluidic systems, and detection platforms that can be readily adapted for use with nucleic acid libraries produced by the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

The methods described herein are not limited to any particular type of sequencing instrumentation used.

EXAMPLES

The following examples serve to describe but not limit the disclosure provided herein.

Example 1: No Attachment Oligonucleotide with User Cleavable Linker

Figure 7A:
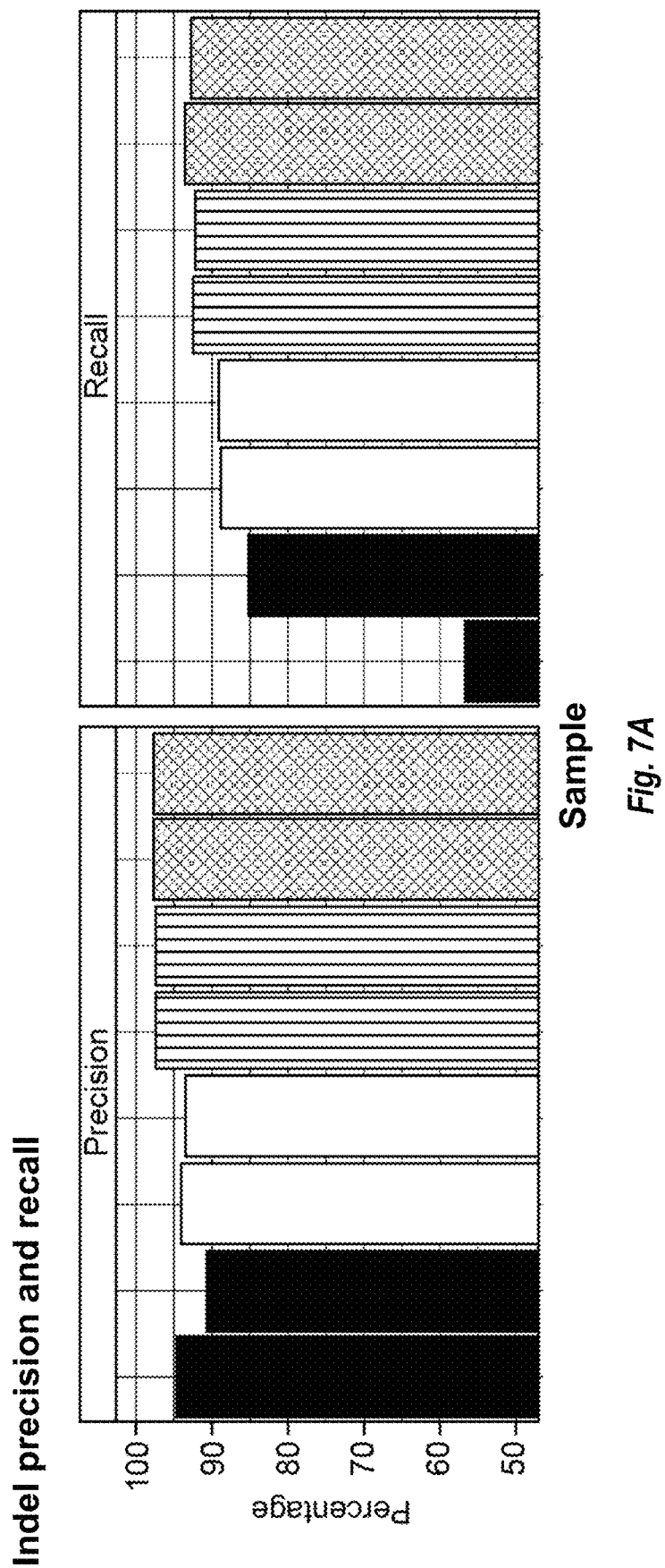
FIGS. 7A-7B depict exemplary results for performing a method of generating a library of tagged nucleic acid fragments with and without using PCR amplification, including results for improved indel precision and recall (FIG. 7A) and improvement in coverage in GC rich promoters (FIG. 7B). Four methods were used to generate these data, two with PCR (TruSeq™ Nano and Nextera™ DNA Flex) and two PCR-free (the present method and TruSeq™ PCR-Free). There were two replicates per method, with eight libraries generated in total. Data were down-sampled to 25× after sequencing.
Figure 7B:
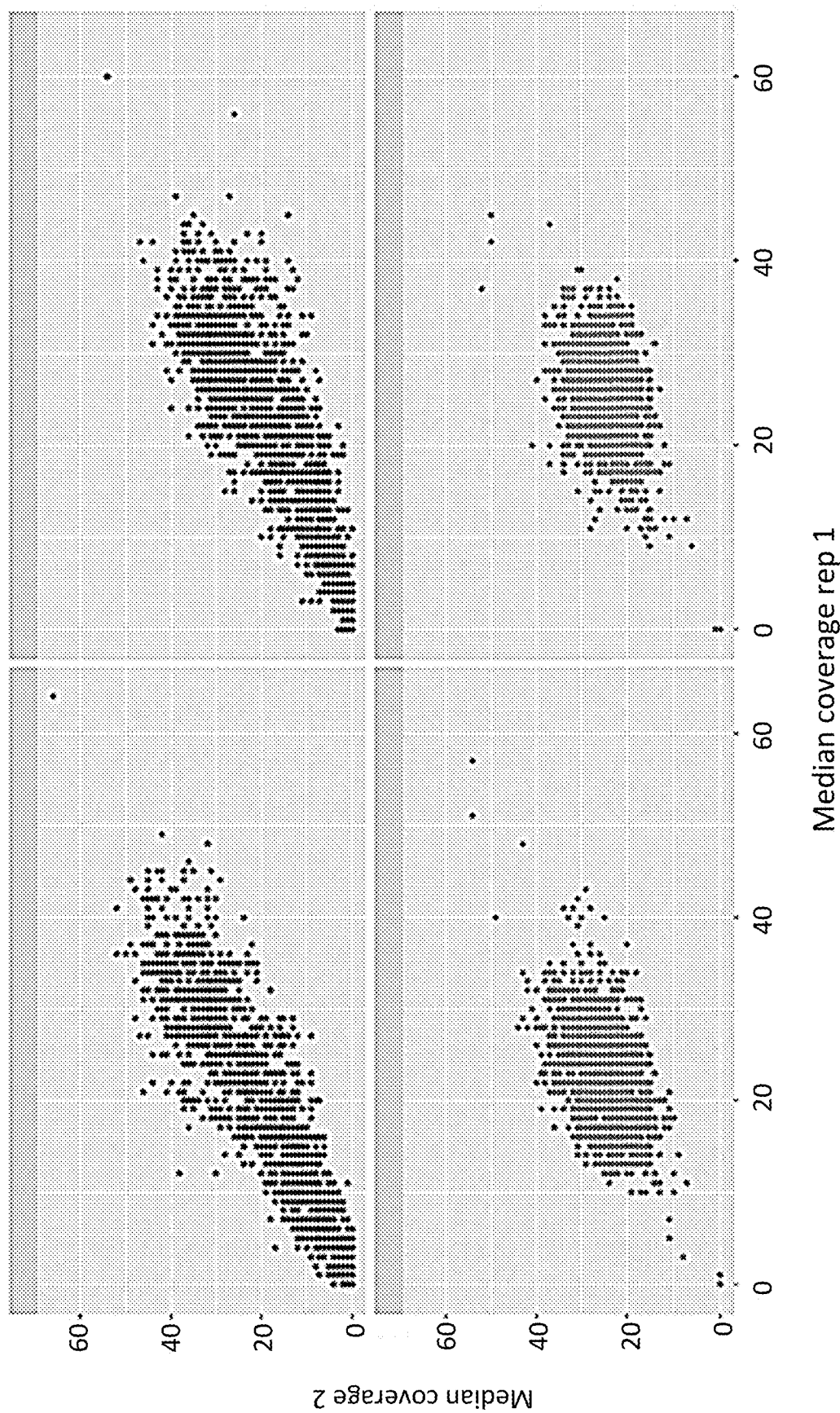

An experiment was done to compare PCR-free sequencing data to PCR sequencing data. Libraries were prepared using TruSeq PCR-free, TruSeq Nano (+PCR), Nextera Flex (+PCR), and the present method and then sequenced to 25× coverage. There were two replicates with each method, with eight libraries in total. FIG. 7A shows that PCR-free methods (striped bars and checked bars, which represent the present method and TruSeq PCR-free, respectively) have improved indel precision and recall compared to the methods with PCR (black bars and white bars, which represent TruSeq Nano and Nextera Flex, respectively). FIG. 7B shows that coverage of GC-rich promoter regions is also improved in the PCR-free methods (bottom two panels, with the present method in the bottom left panel and TruSeq PCR-free in the bottom right panel).

Example 2: Generating a Library of Tagged Nucleic Acid Fragments without Using PCR Amplification Step A1. Formation of Immobilized Transposome Complexes—Indexed Beads.

A mixture of: (1) first transposon having a 3' mosaic end (ME) sequence (SEQ ID NO: 6), a first tag sequence (A14), and a 5' primer sequence (P5') (25 µM final concentration); (2) a second transposon with a 5' complementary mosaic end sequence (ME'; SEQ ID NO: 3) and a second tag sequence (B15') (37.5 µM final concentration); and (3) an attachment polynucleotide that included a 3' sequence complementary to the second tag sequence (B15), an index sequence (in this case, i701 in Table 1), and a 5' primer sequence (P7) with a biotin at the 5' terminus (25 µM final concentration) were annealed by treating with 10 mM Tris-HCl (pH 8.0), 1 mM EDTA, and 25 mM NaCl, heating at 95° C. for 10 min, and then cooling to 10° C. over approximately 15 min. The annealed transposons/attachment polynucleotide (2 µM final concentration based on attachment polynucleotide) were then mixed with a transposase enzyme (6.1 µM final concentration) and incubated at 37° C. overnight to form solution-phase transposome complexes (FIG. 4A, indexed bead figures). The solution-phase transposome complexes were then immobilized on solid support by mixing with streptavidin-coated beads. In some examples, the immobilization may be carried out in the presence of HT1 buffer (Illumina), which is a high salt buffer that aids formation of biotin-streptavidin bonds. After rotating in HT1 for 1 h, the beads were pelleted and washed once in a mixture of HT1 buffer and 50% glycerol standard storage buffer (Illumina) (9:1). The beads were then resuspended in 360 µL of buffer containing 50 mM Tris pH 7.5, 30 mM NaCl, and 0.1% Tween 20. 40 µL of EPX2 (Illumina) was added and the beads were rotated for a further 10 min at room temperature. The beads were pelleted again and then resuspended in 396 µL of the same buffer, treated with 4 µL of single-stranded binding protein (5 mg/mL), and rotated again for 10 min. The beads were pelleted again, washed once in the 9:1 HT1:standard storage buffer mixture, and resuspended in 15% glycerol standard storage buffer (Illumina). The resulting indexed beads were used in single indexing and dual indexing tagmentation protocols.

Step A2. Formation of Immobilized Transposome Complexes—Universal Beads.

Annealed transposons were prepared as described in Step A1, with the exception that the attachment polynucleotide included a 5' sequence complementary to the first tag sequence (A14') and a 3' primer sequence (P5') with a biotin at the 3' terminus (for single indexing), and optionally an intervening universal nitroindole sequence (for dual indexing). The transposome complexes were prepared from the annealed transposons and immobilized on solid support as described for Step A1. The resulting universal beads were used in single indexing and dual indexing tagmentation protocols as indicated.

Step B. Tagmentation.

Figure 4B:
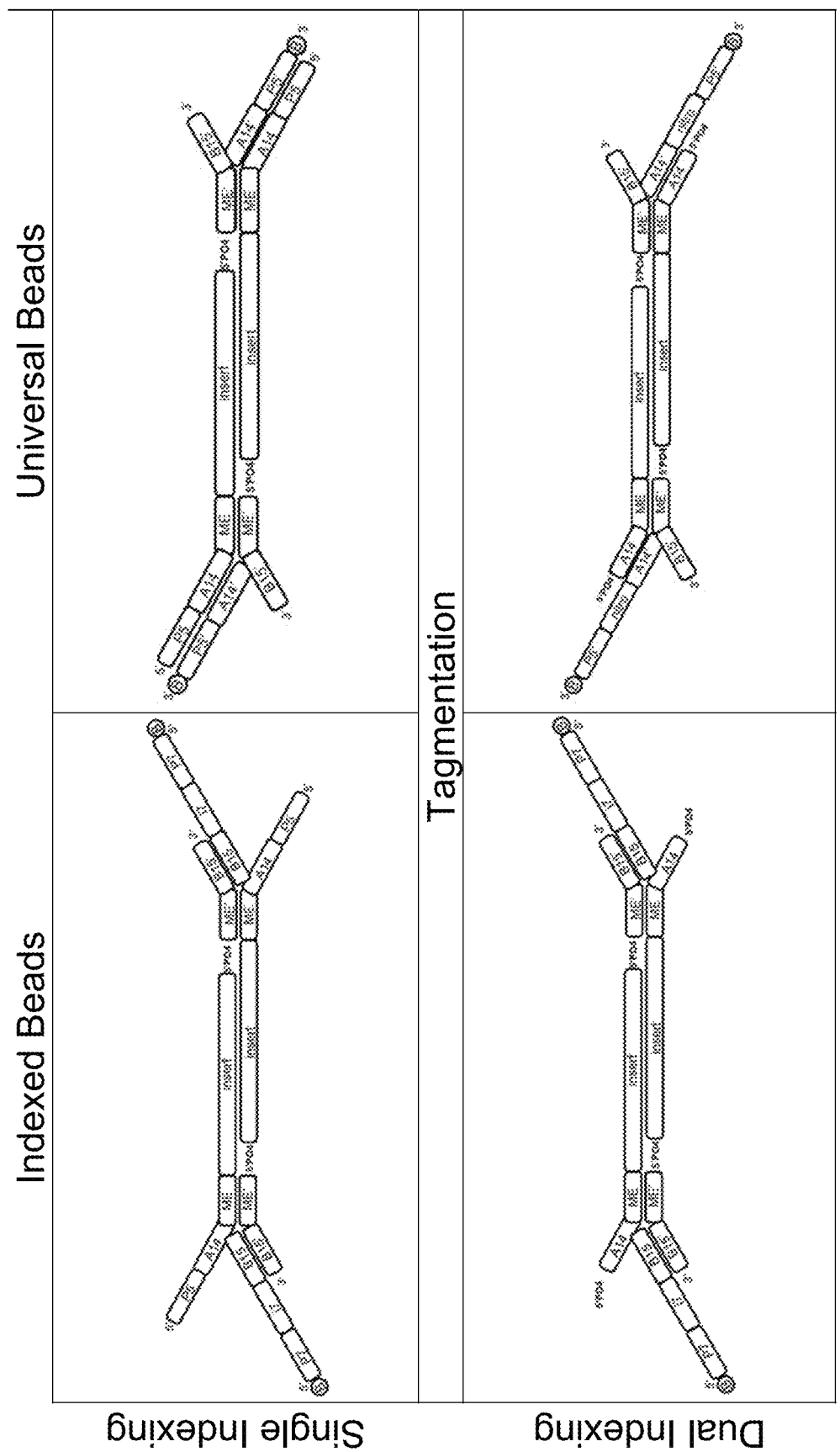

DNA (e.g., about 50 pg to 5 µg) was mixed with immobilized transposome complexes and 50 µL of tagmentation buffer (10 mM Tris acetate (pH 7.6), 5 mM magnesium acetate, and 10% dimethylformamide, as described in U.S. Pat. Nos. 9,080,211, 9,085,801, and 9,115,396, each of which is incorporated by reference, and the resulting mixture was incubated at 55° C. for 5 min. A library of tagged DNA fragments immobilized on the beads was generated. The tagmentation reaction mixture was treated with 10 of a stop buffer comprising 5% SDS, 100 mM Tris-HCl (pH7.5), 100 mM NaCl, and 0.1% Tween 20, and the resulting mixture was incubated at 37° C. for 5 min to denature the transposase enzyme from the transposome complexes. The beads with the immobilized DNA fragments were then pelleted on a magnet and washed three times in wash buffer (100 mM Tris-HCl (pH 7.5), 100 mM NaCl, and 0.1% Tween) to remove any residual SDS. The beads were separated from the supernatant by magnetic capture and were washed further using 100 mM Tris-HCl (pH 7.5), 100 mM NaCl, and 0.1% Tween 20. The resulting tagmented fragments for all four approaches are depicted in FIG. 4B.

Step C. Extension, Ligation, and Indexing.

Figure 4C:
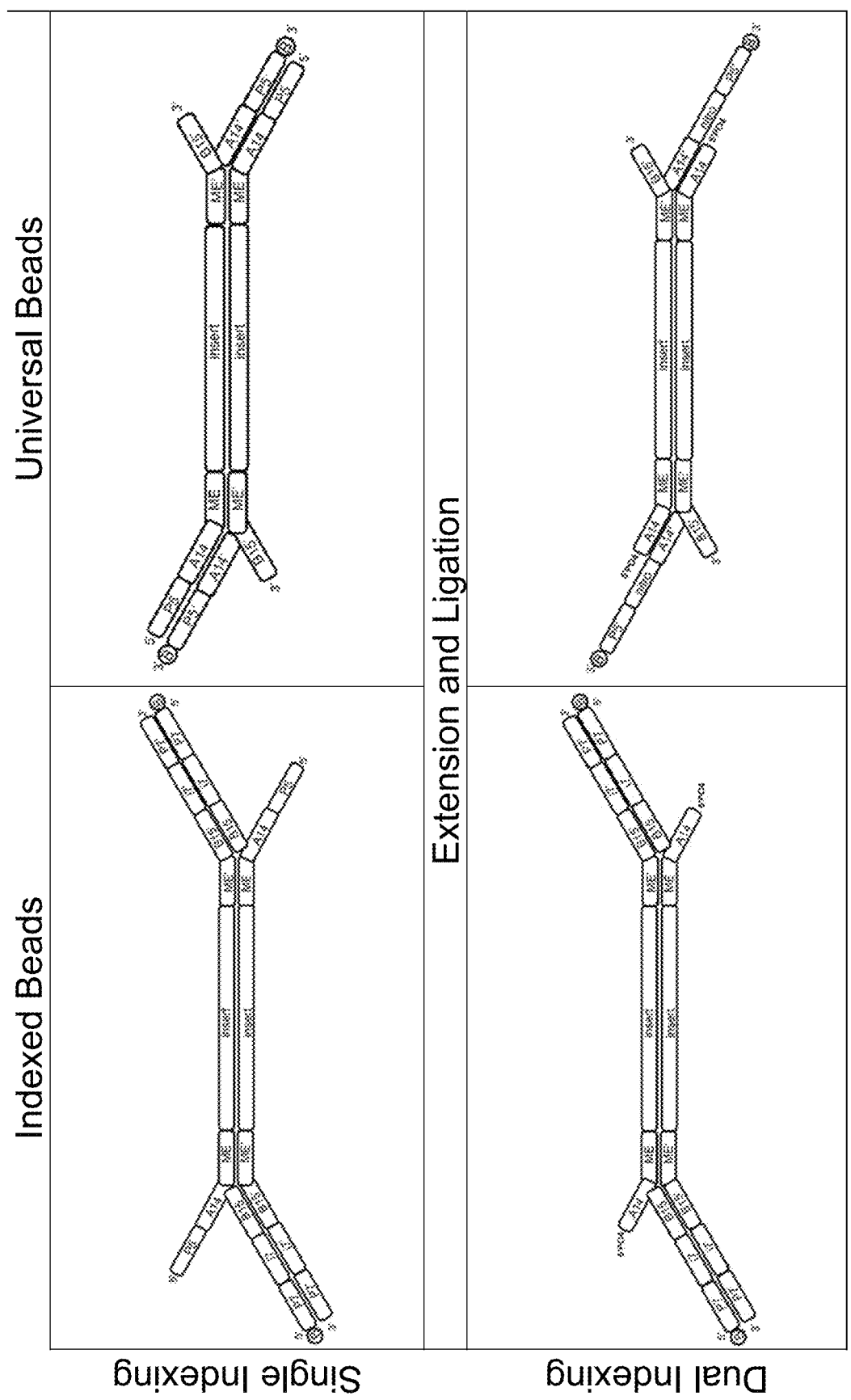
Figure 4D:
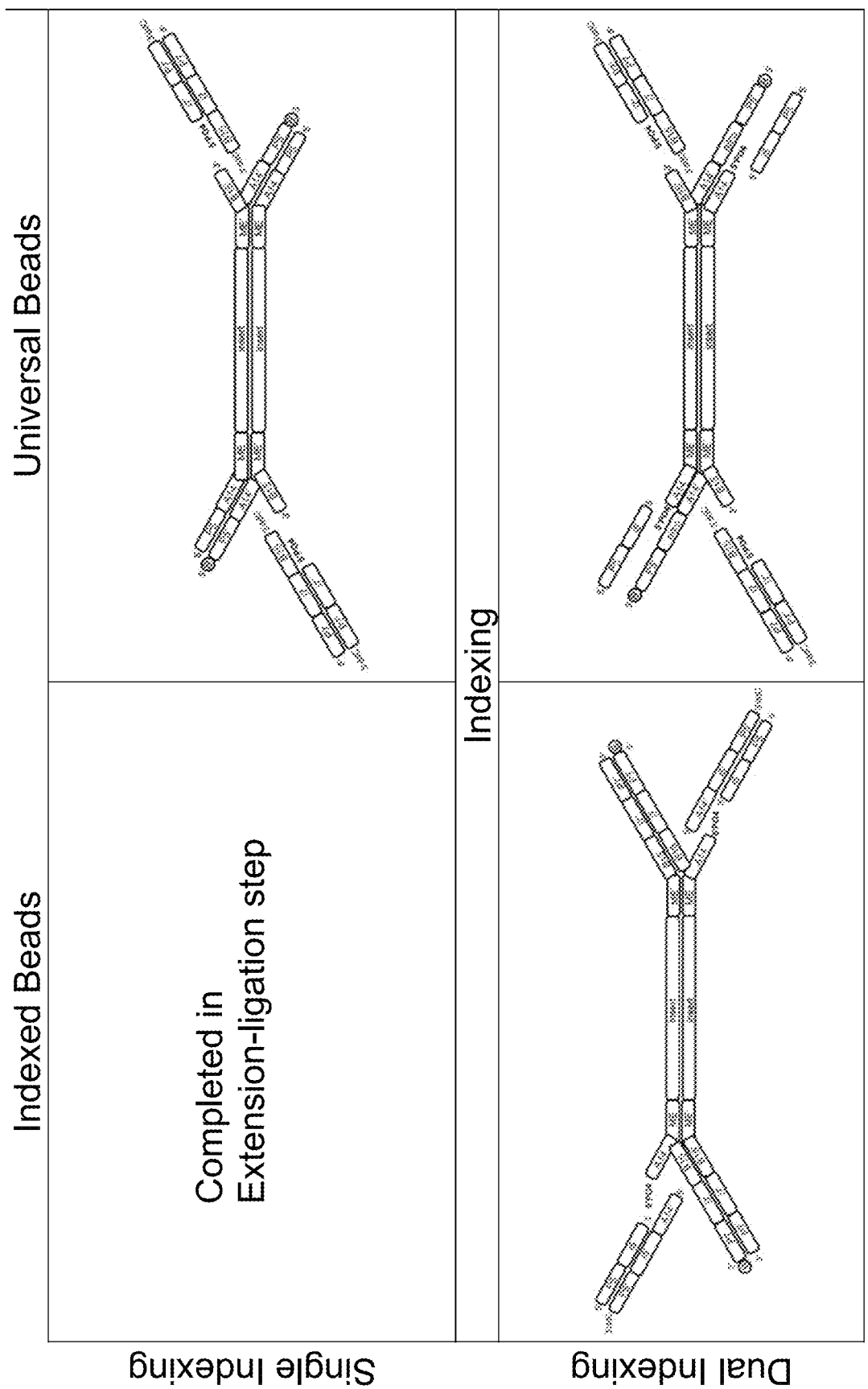

Extension and ligation was performed by contacting the beads with an extension and ligation mix (ELM) that included T4 DNA polymerase (exonuclease minus) and *E. coli* DNA ligase and incubating at 30° C. for 15 min followed by 16° C. for 15 min, thereby gap filling DNA fragments between the 3' ends of the fragments and the 5' ends of the ME' sequences and extending single-stranded regions to generate fully double-stranded products by incorporating the remaining sequences from the attachment polynucleotide (FIG. 4C). In certain cases, indices were also added during this step. As shown in FIG. 4D, top right figure, an index was added to the universal bead/single index construct by adding an oligonucleotide with a double-stranded primer sequence (P7/P7'), a double-stranded index sequence (in this case, i701/i701'), and a single-stranded overhang region with a 3' sequence complementary to the second tag sequence (B15). For the indexed beads/dual indexing approach (FIG. 4D, bottom left figure), the index reagent included a double-stranded primer sequence (P5/P5'), a double-stranded index sequence (in this case, i501/i501'), and a single stranded overhang region with a 5' sequence complementary to the first sequence tag (A14'). For the universal beads/dual indexing approach (FIG. 4D, bottom right figure), the index reagent was the same as for the universal bead/single index case, but an additional second index reagent including a complementary primer sequence (P5) and an index sequence (i5) was hybridized and ligated to the 5' end of the A14 sequences.

The reaction mixture was treated with 10 μL of a stop buffer comprising 5% SDS, 100 mM Tris-HCl (pH 7.5), 100 mM NaCl, and 0.1% Tween 20, and the resulting mixture was incubated at 37° C. for 5 min to denature the transposase enzyme from the transposome complexes. The beads with the immobilized DNA fragments were then pelleted on a magnet and washed three times in wash buffer (100 mM Tris-HCl (pH 7.5), 100 mM NaCl, and 0.1% Tween) to remove any residual SDS. The beads were separated from the supernatant by magnetic capture and were washed further using 100 mM Tris-HCl (pH 7.5), 100 mM NaCl, and 0.1% Tween 20.

Step D. Release of Tagged Fragments.

After the third wash, the beads were resuspended in 100 μL of 0.2 N NaOH to denature the library fragments and release them from the beads. The library was purified by adding 100 μL of supernatant directly to 180 μL of SPRI beads, following the standard SPRI purification protocol, and eluting in 15 μL of Illumina resuspension buffer. The libraries were quantified by qPCR, and then prepared for sequencing on a MiSeq® by diluting to 5 μL of about 3200 pM and denaturing with 5 μL of 0.2 N NaOH at room temperature for 5 minutes. Chilled Illumina HT1 buffer (990 μL) was added and the full 1 mL mixture was loaded into the MiSeq® cartridge.

Figure 4E:
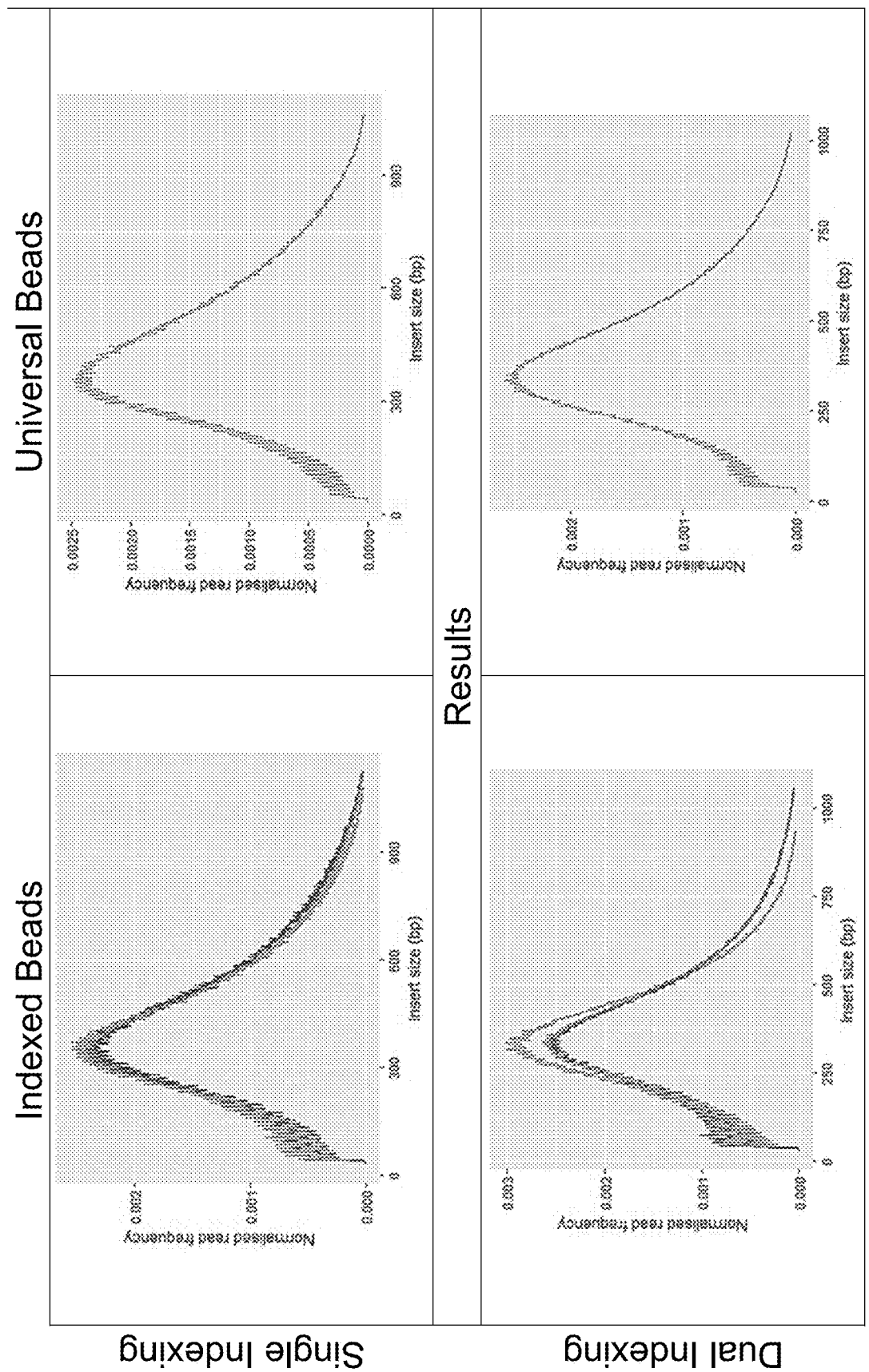
Figure 5A:
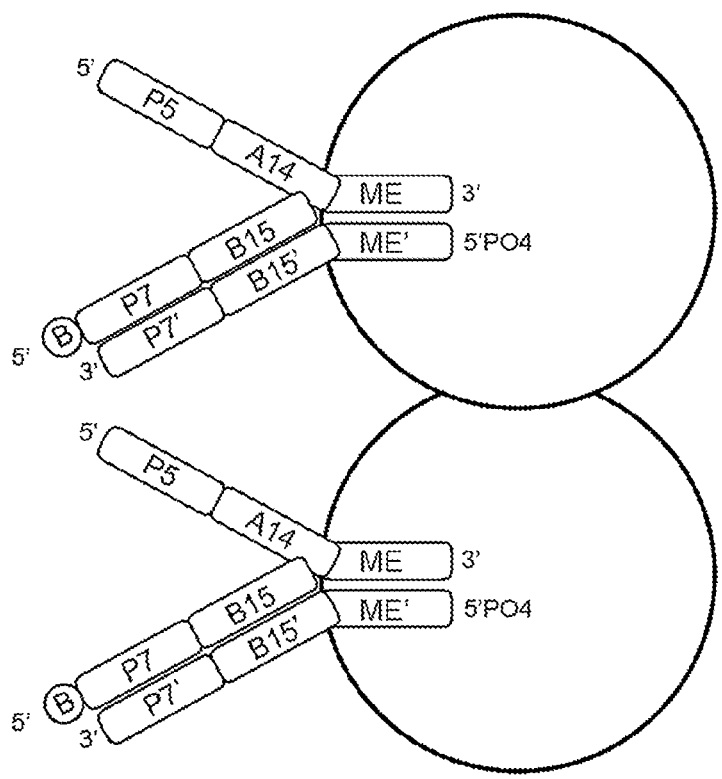
FIGS. 5A and 5B depict a schematic diagram of exemplary transposome complexes for non-indexing, showing the attachment polynucleotide hybridized to either the P7 sequence-containing transposon (FIG. 5A) or the P5 sequence-containing transposon (FIG. 5B). Specifically.
Figure 5B:
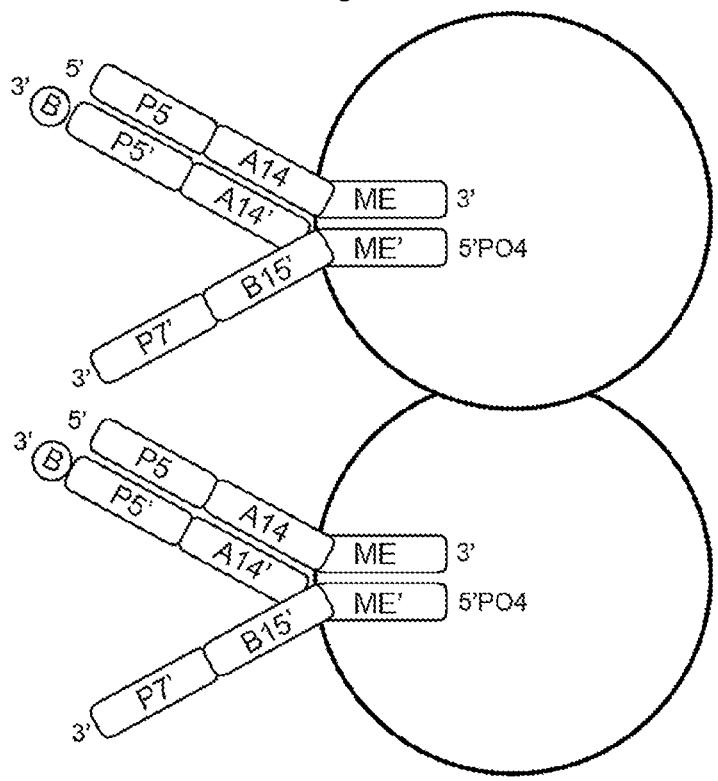

Results are shown in FIG. 4E, and summarized in Table 2 below, for indexed beads or universal beads with single or dual indexing.

TABLE 2

Results of Library Preparation for Various Transposome Complex Configurations

| Sample | Median Insert | Clusters | Reads Aligned | Bases Aligned |
|---|---|---|---|---|
| Indexed Beads, Single Indexing (3 samples) | 390, 404, 393 | 93% | 87%, 87%, 90% | 85%, 85%, 88% |
| Universal Beads, Single Indexing (1 sample) | 417 | 84% | 53% | 83% |
| Indexed Beads, Dual Indexing (3 samples) | 353, 364, 366 | 90% | 91%, 90%, 88% | 90%, 90%, 90% |

TABLE 2-continued

Results of Library Preparation for Various Transposome Complex Configurations

| Sample | Median Insert | Clusters | Reads Aligned | Bases Aligned |
|---|---|---|---|---|
| Universal Beads, Dual Indexing (1 sample) | 385 | 91% | 68% | 86% |

Using the methods described herein, the biases in sequencing data that are typically introduced with PCR were overcome. For example, using the PCR-free methods described herein, the resulting libraries of nucleic acid fragments were sequenced, and the sequences did not have significant gaps in the GC rich regions, as is typically observed when PCR is used.

Example 3: Sequencing Comparison of Test Libraries

Figure 8:
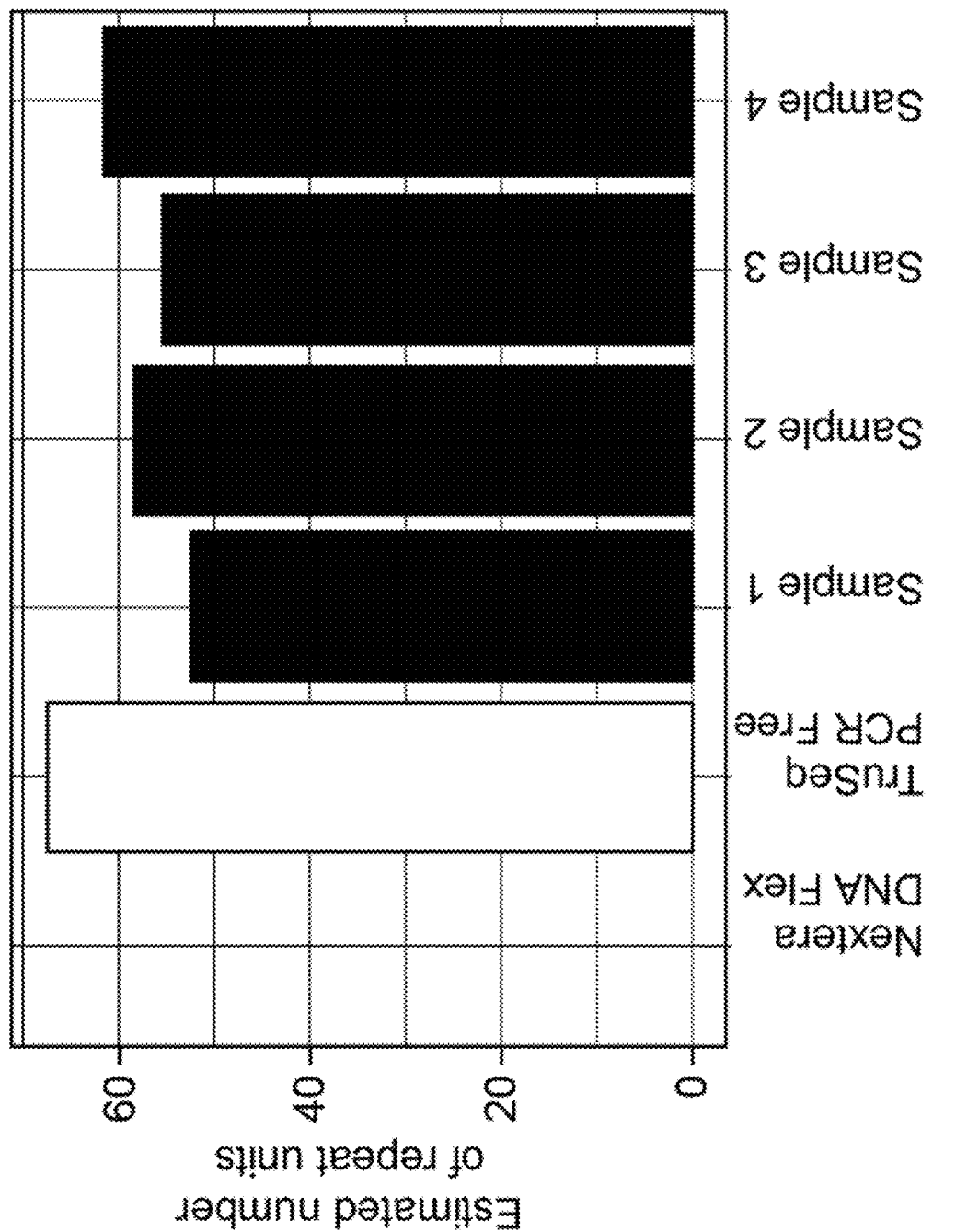
FIG. 8 depicts results of sequencing libraries from a sample containing a known 100% GC repeat expansion (FMR1) prepared using Nextera™ DNA Flex or TruSeq™ DNA PCR-Free Library Prep Kits for comparison to the methods described herein (in quadruplicate Samples 1-4) as described in Example 3.

In this example, two comparison libraries from a sample containing a known 100% GC repeat expansion (FMR1) were prepared using Nextera™ DNA Flex (which includes PCR) and TruSeq™ PCR-Free Library Prep Kits) and four test libraries were prepared as described herein using the universal beads/dual indexing method, as shown in FIG. 4D. As shown in FIG. 8, no repeats were called in the sequencing data from the library prepared using Nextera™ DNA Flex (first column, no bar shown as result was 0). Repeats were called using TruSeq™ PCR-Free (column 2) and the four test libraries using the methods described herein (Samples 1-4, columns 3-6). Thus, the present methods demonstrate improved calling of repeat expansion samples with 100% GC regions.

Example 4: Forked Oligonucleotide with Cleavable Linker

Step 1. Formation of Transposome Complexes.

A biotinylated oligonucleotide (50 μM) comprising a 5' biotin, three T residues, then three U residues, P5, A14, and ME, with the sequence:

(SEQ ID NO: 20)
/5Biosg/TTUUUAATGATACGGCGACCACCGAGATCTACACTCGTCGG

CAGCGTCAGATGTGTATAAGAGACA and an oligonucleotide comprising ME' B15' P7' (75 μM) with the sequence:

(SEQ ID NO: 21)
CTGTCTCTTATACACATCTCCGAGCCCACGAGACATCTCGTATGCCGTC

Figure 2A:
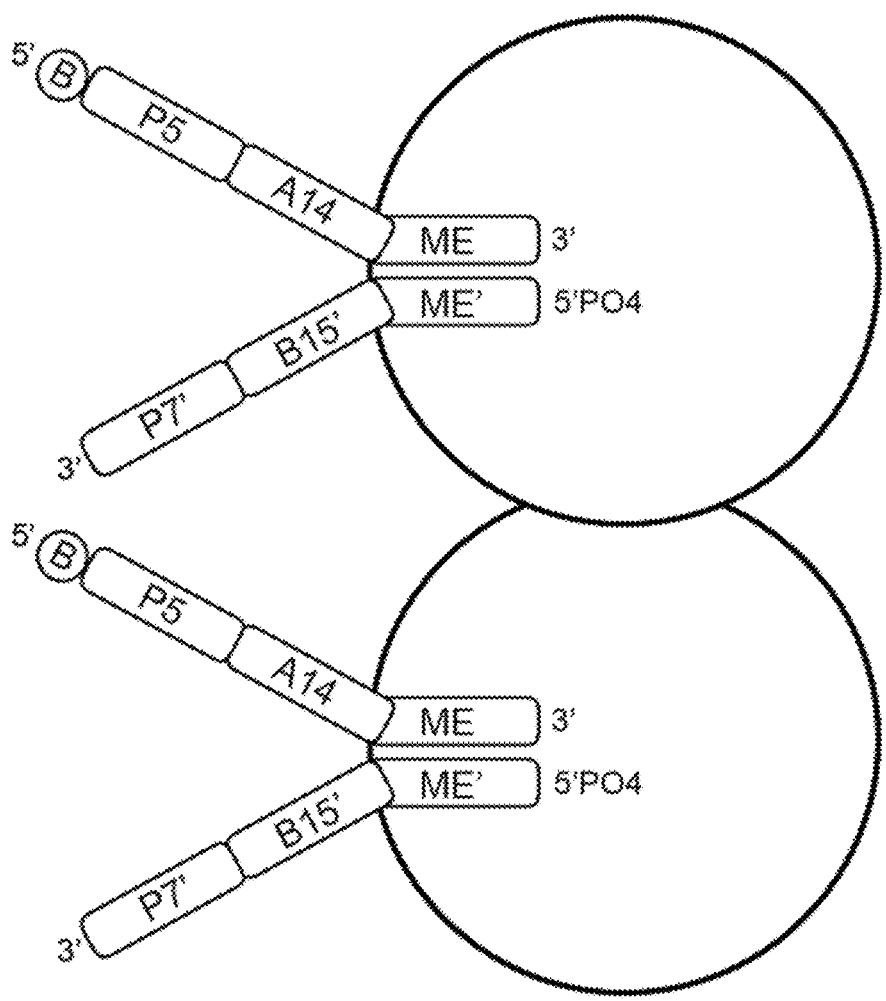
FIGS. 2A-2B illustrate a schematic diagram and method of preparing a library of tagged nucleic acid fragments without using PCR amplification.

TTCTGCTTG was treated with 10 mM Tris-HCl (pH 8.0), 1 mM EDTA, and 25 mM NaCl, heated to 95° C. for 10 min, and then cooled to 10° C. at −0.1° C. per second. The annealed transposons were then mixed with a transposase enzyme so that the final concentration of biotinylated oligo was 2 μM the transposase concentration was 4 μM. The mixture was incubated at 37° C. overnight to form solution-phase transposome complexes. The solution-phase transposome complexes were then immobilized on solid support by mixing with streptavidin-coated beads and HT1 buffer (Illumina) and rotating at room temperature for 1 h. The beads were then washed three times in HT1 buffer before being resuspended in 15% glycerol standard storage buffer (Illumina) (FIG. 2A).

Step 2. Tagmentation.

DNA (e.g., about 50 pg to 5 µg) was mixed with immobilized transposome complexes and 50 µL of tagmentation buffer (10 mM Tris acetate (pH 7.6), 5 mM magnesium acetate, and 10% dimethylformamide, as described in U.S. Pat. Nos. 9,080,211, 9,085,801, and 9,115,396, each of which is incorporated by reference, and the resulting mixture was incubated at 55° C. for 5 min. A library of tagged DNA fragments immobilized on the beads was generated. The tagmentation reaction mixture was treated with 10 µL of a stop buffer comprising 5% SDS, 100 mM Tris-HCl (pH7.5), 100 mM NaCl, and 0.1% Tween 20, and the resulting mixture was incubated at 37° C. for 5 min to denature the transposase enzyme from the transposome complexes. The beads with the immobilized DNA fragments were then pelleted on a magnet and washed three times in wash buffer (100 mM Tris-HCl (pH 7.5), 100 mM NaCl, and 0.1% Tween) to remove any residual SDS. The beads were separated from the supernatant by magnetic capture and were washed further using 100 mM Tris-HCl (pH 7.5), 100 mM NaCl, and 0.1% Tween 20.

Step 3. Extension and Ligation.

Extension and ligation were performed by contacting the beads with an extension and ligation mix (ELM) that included T4 DNA polymerase (exonuclease minus) and *E. coli* DNA ligase and incubating at 30° C. for 15 min followed by 16° C. for 15 min, thereby gap filling DNA fragments between the 3' ends of the fragments and the 5' ends of the ME' sequences. The reaction mixture was treated with 10 µL of a wash buffer comprising 5% SDS, 100 mM Tris-HCl (pH7.5), 100 mM NaCl, and 0.1% Tween 20, and the resulting mixture was incubated at 37° C. for 5 min to denature the transposase enzyme from the transposome complexes. The beads with the immobilized DNA fragments were then pelleted on a magnet and washed three times in wash buffer (100 mM Tris-HCl (pH 7.5), 100 mM NaCl, and 0.1% Tween) to remove any residual SDS. The beads were separated from the supernatant by magnetic capture and were washed further using 100 mM Tris-HCl (pH 7.5), 100 mM NaCl, and 0.1% Tween 20.

Step 4. Release of Tagged Fragments.

Figure 2B:
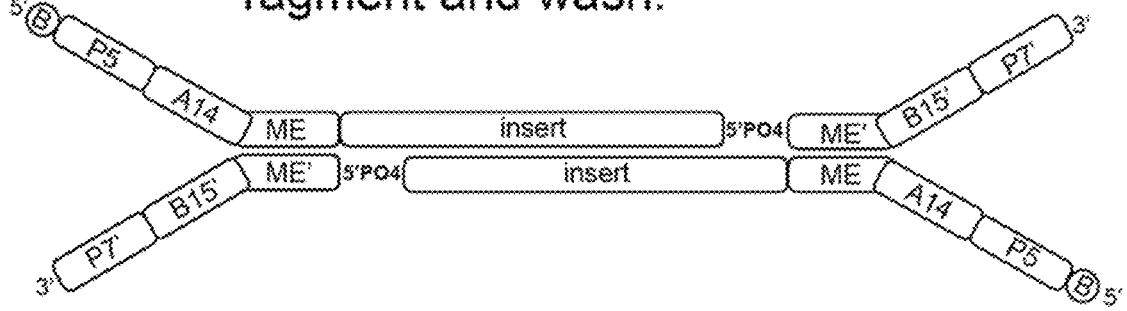
Figure 2B:
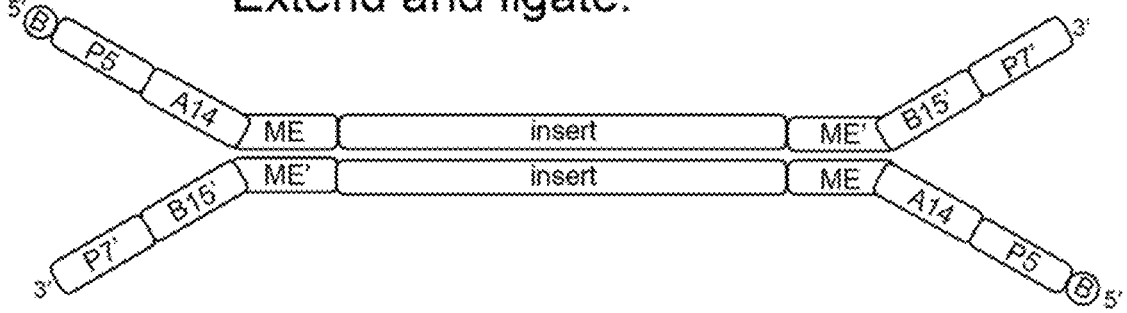
Figure 2B:
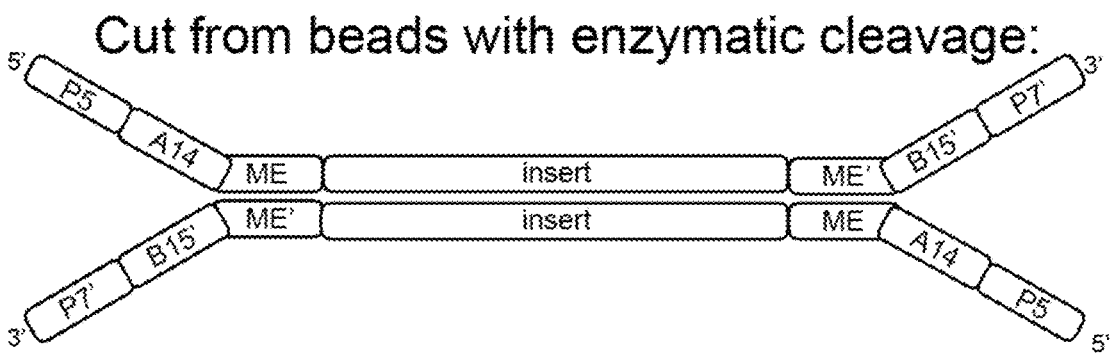

After the third wash, the beads were resuspended in a buffer containing 50 mM potassium acetate, 20 mM tris-acetate, 10 mM magnesium acetate, and 100 µg/mL BSA. 5 µL of an enzyme mixture containing uracil DNA glycosylase and endonuclease VIII were added and the libraries were incubated at 37° C. for 30 min. The enzymes act together to cleave the U's in the attachment oligonucleotides and release the library fragments into solution. The library was purified by adding 100 µL of supernatant directly to SPRI beads, following the standard size selection SPRI purification protocol (0.5× right and 0.7-0.8× left), and eluting in 15 µL of Illumina resuspension buffer. The resulting libraries were quantified by qPCR (FIG. 2B).

Example 5: Modified Extension-Ligation Protocol

Figure 6A:
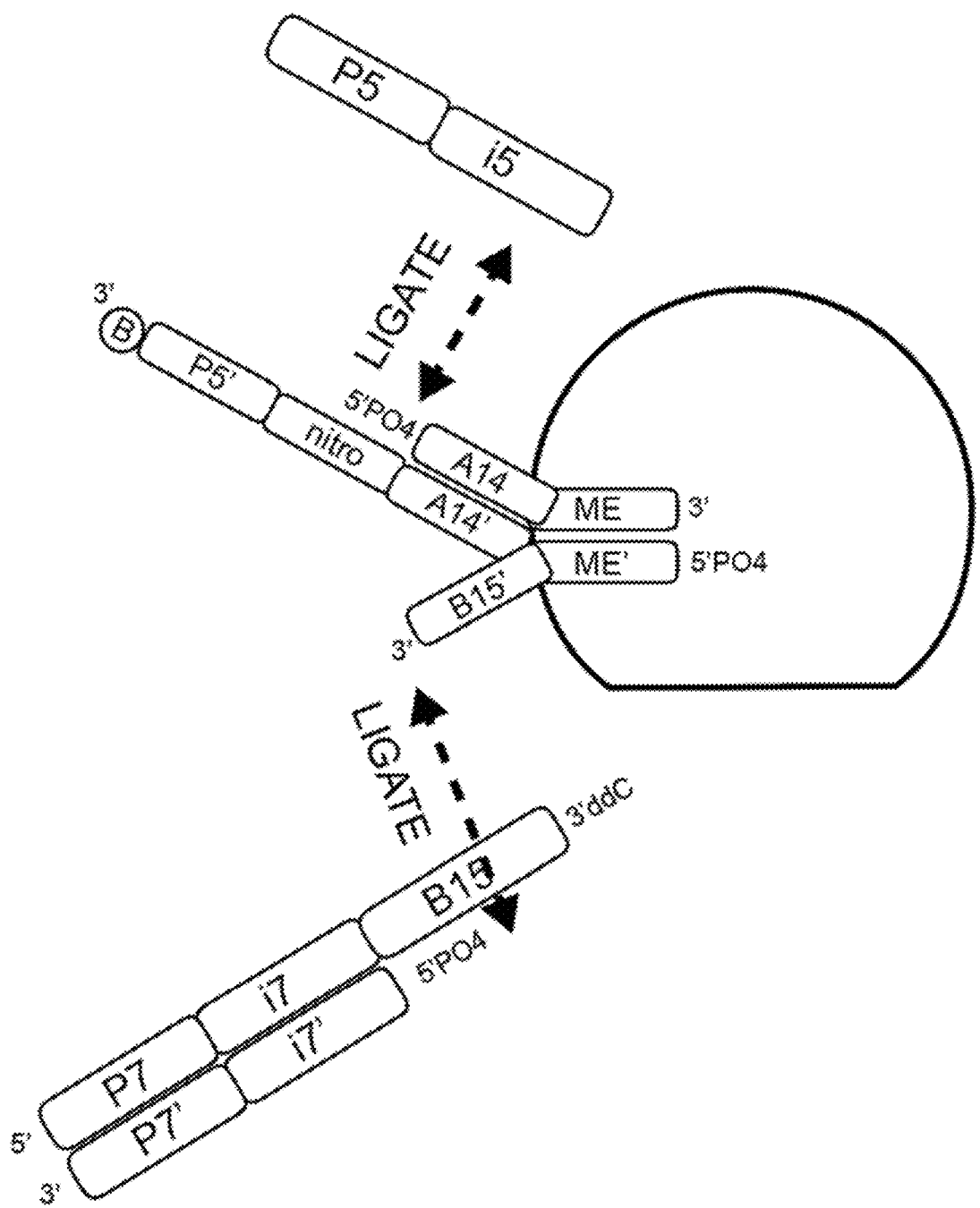
FIGS. 6A-6D depict schematic diagrams of exemplary transposome complexes including an i5 indexing sequence.
Figure 6B:
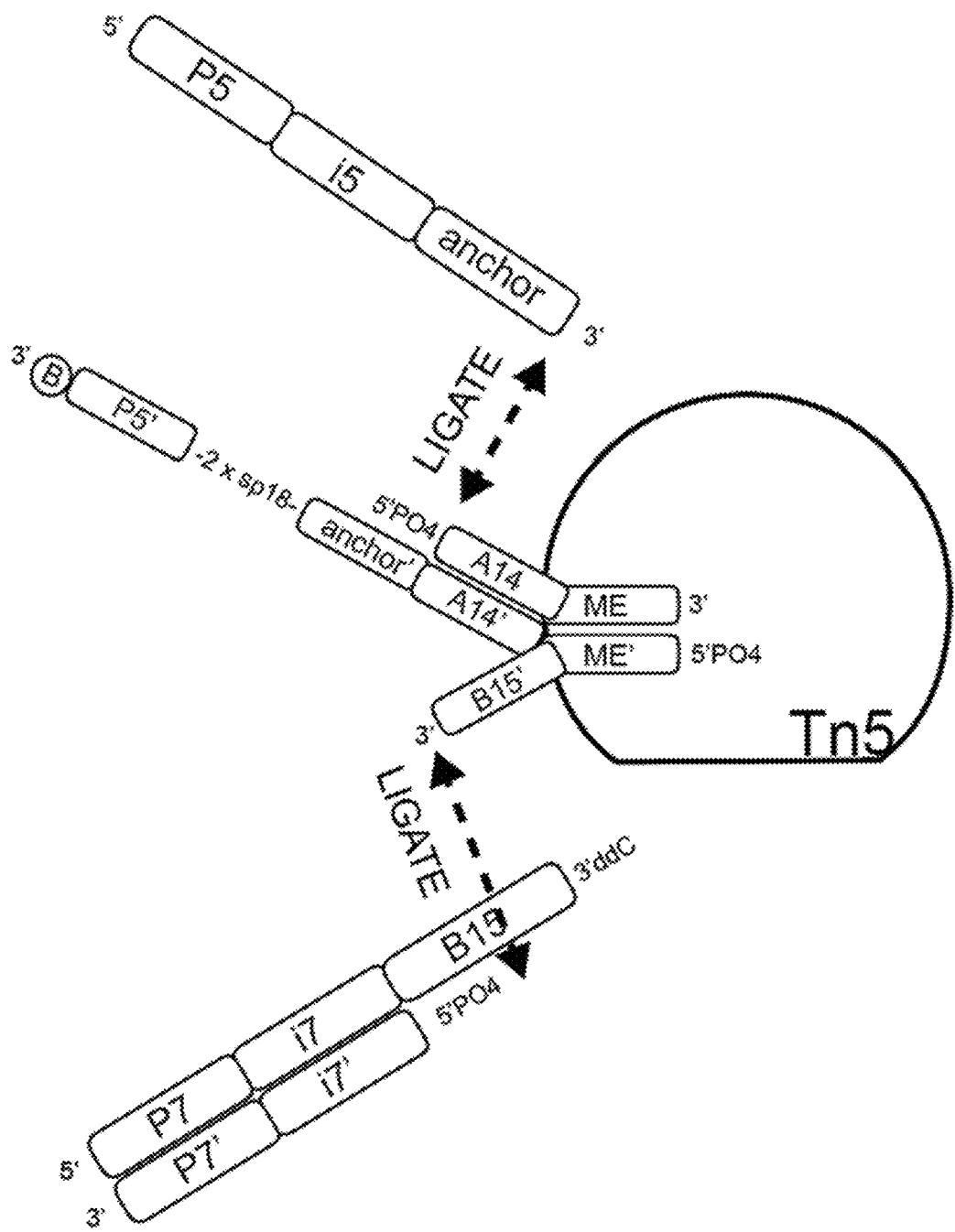
Figure 6C:
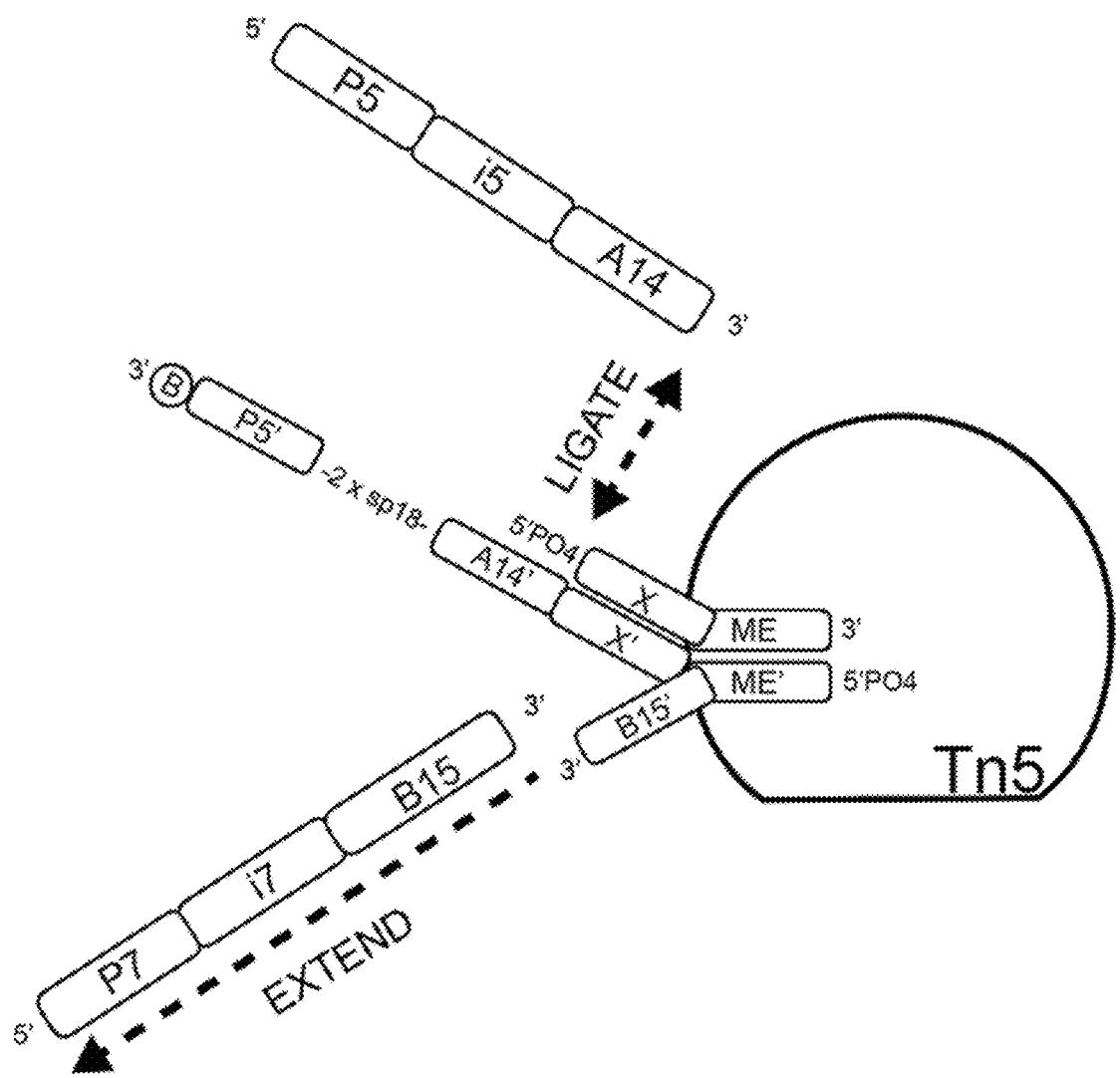
Figure 6D:
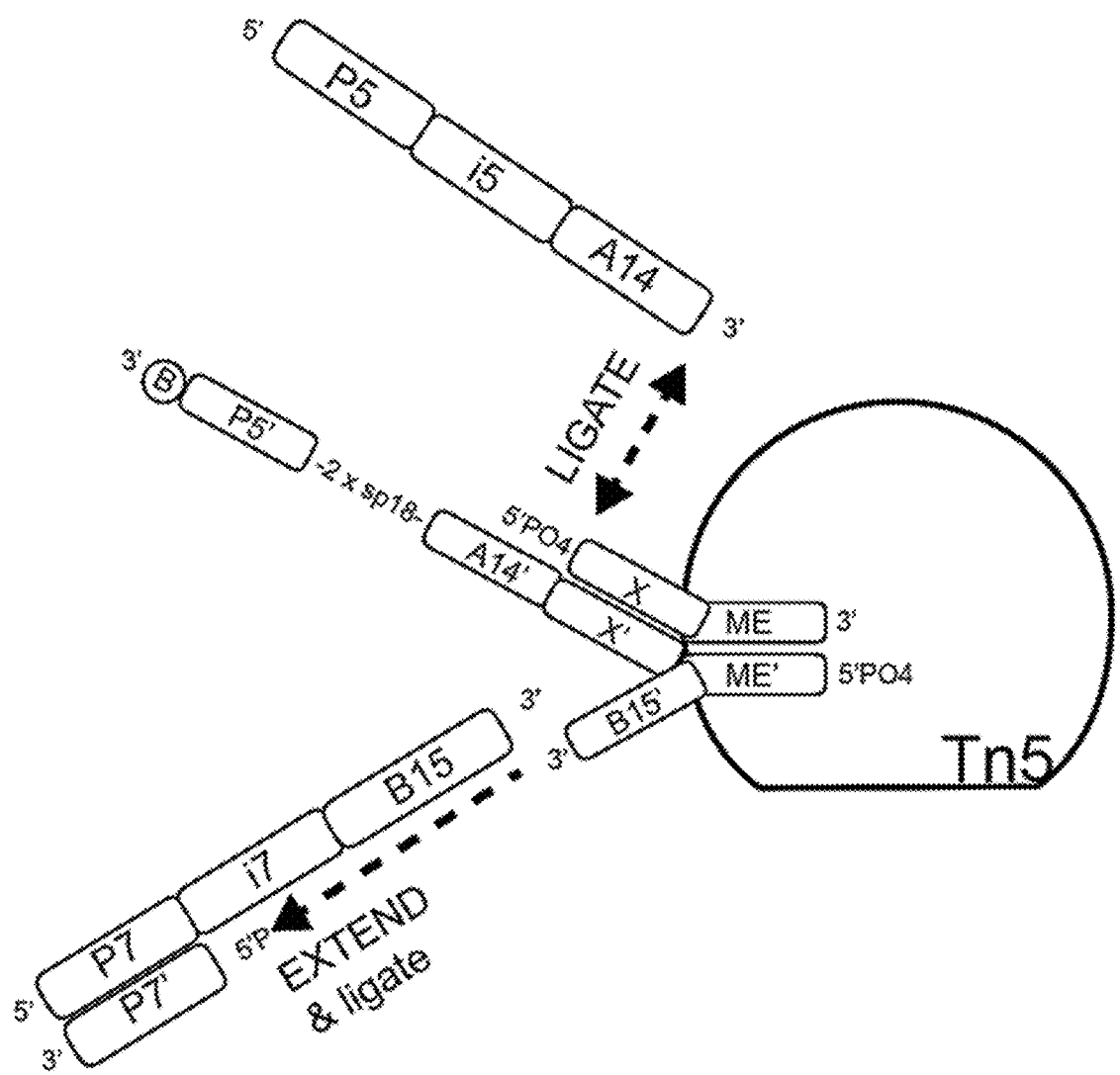
Figure 9A:
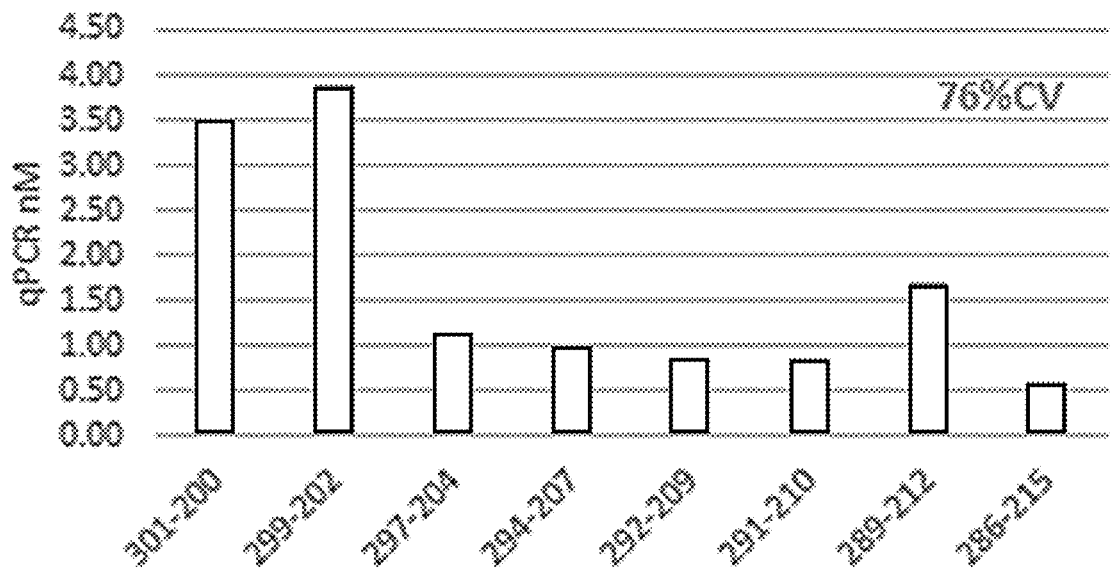
FIGS. 9A-9C depict the % CV results for libraries prepared using eight index pairs along with the systems of FIGS. 6C (data in FIG. 9A) and 6D (data for two reaction conditions in FIGS. 9B and 9C) as described in Example 5.
Figure 9B:
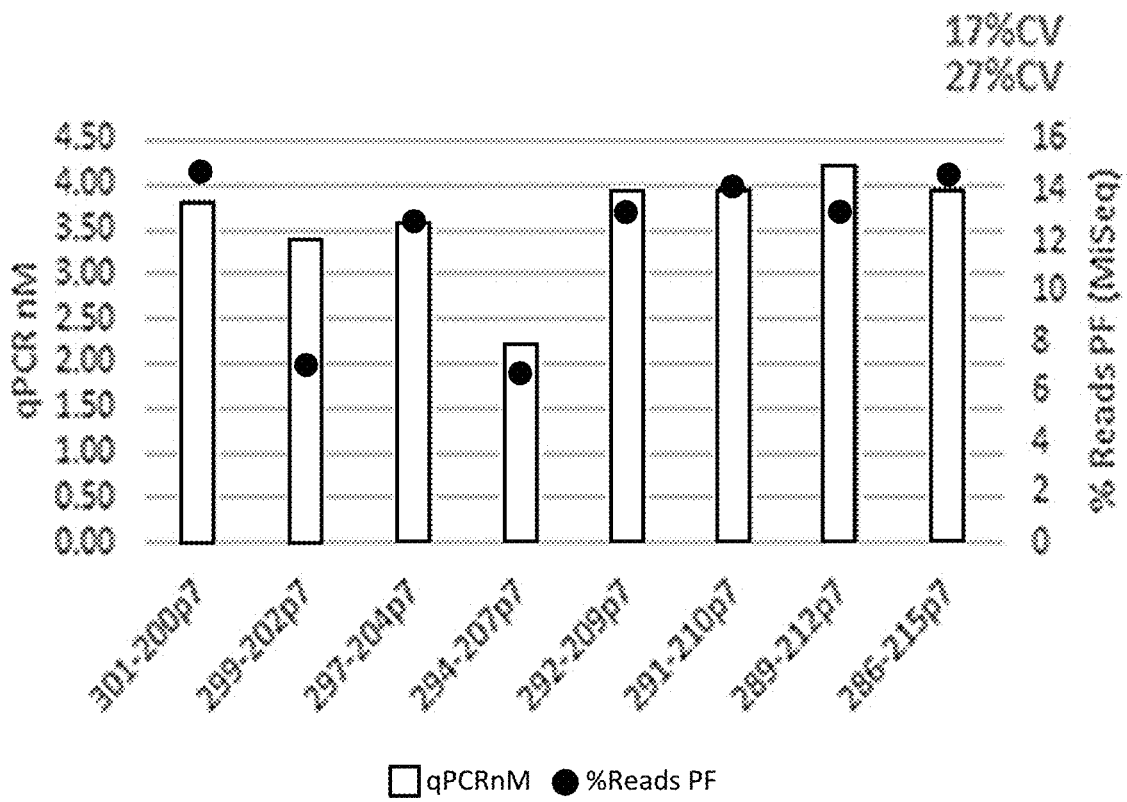

An alternative protocol for the indexed variation extension-ligation reaction (Example 2C) may be used. In some instances, extension of the i7 index is inefficient due to secondary structure in certain index sequences. Thus, for the construct from FIG. 6C, eight different index pairs were investigated. As shown in FIG. 9A, the % CV of the index pool was 76%. It was discovered that adding a P7' oligonucleotide during the extension-indexing reaction boosts the performance of certain index pairs, perhaps due to hybridization to the P7 sequence that may disrupt or prevent secondary structure formation. In this instance, the extension-indexing reaction also includes ligation. P7' (with 5' phosphate for ligation) is added during the extension-ligation-indexing reaction at 2.5 µM. For the construct shown in FIG. 6D, FIG. 9B shows the % CV for eight index pairs at less than 30%.

Figure 9C:
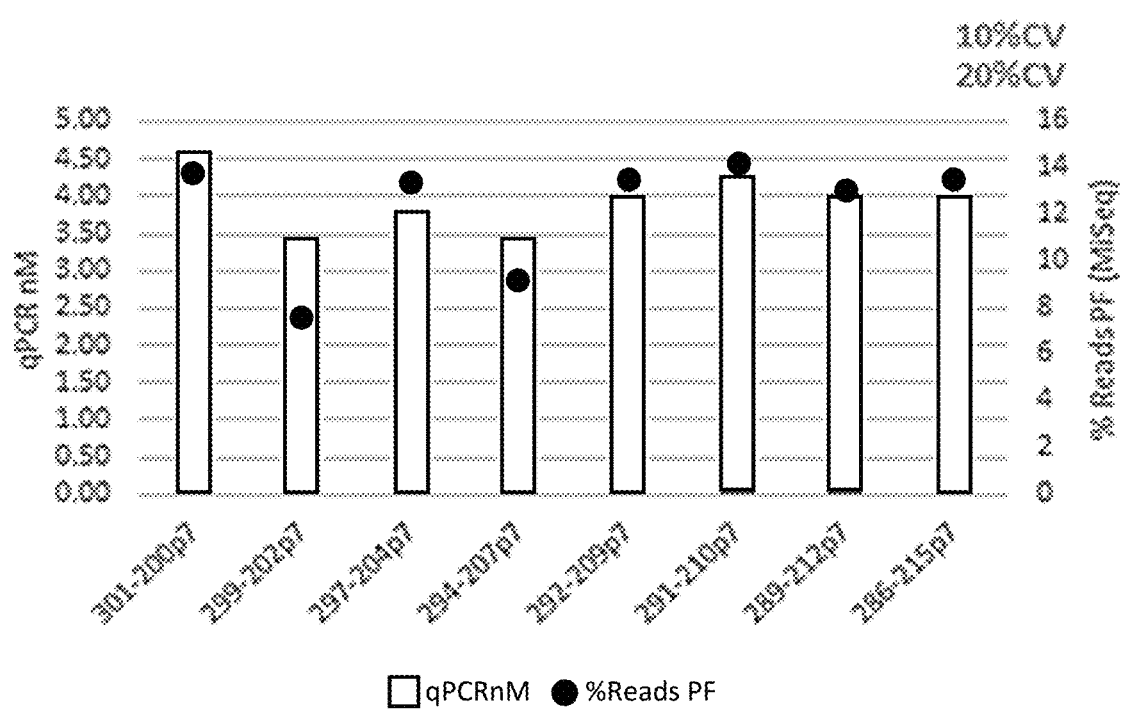

The addition of DMSO to the P7' oligo extension-ligation-indexing reaction improves % CV further. In this example, for the construct of FIG. 6D, DMSO is added to the extension-ligation-indexing reaction at 5%. The extension-ligation reaction contains all of the necessary enzymes and components for extension and ligation. The reaction is incubated at 37° C. for 30 min before proceeding with the workflow as normal. As shown in FIG. 9C, % CV for eight different index pairs was less than 20%. This result allows the system to be used without quantifying DNA output from the library for each sample to adjust for variations in indexing performance.

Example 6: PCR Free Immobilized Transposome in Tube

This example demonstrates a method and system for immobilizing transposome complexes in a tube, such as in a PCR tube, for PCR free whole genome sequencing. The methods are performed similarly to the method as described in Example 2, and the entire preparation may be performed in the same tube.

Formation of Immobilized Transposome Complexes in a Tube.

A mixture of: (1) first transposon having a 3' mosaic end (ME) sequence (SEQ ID NO: 6), a first tag sequence (A14), and a 5' primer sequence (P5) (25 µM final concentration); (2) a second transposon with a 5' complementary mosaic end sequence (ME'; SEQ ID NO: 3) and a second tag sequence (B15') (37.5 µM final concentration); and (3) an attachment polynucleotide that included a 3' sequence complementary to the second tag sequence (B15), an index sequence, and a 5' primer sequence (P7) with a biotin at the 5' terminus (25 µM final concentration) were annealed by treating with 10 mM Tris-HCl (pH 8.0), 1 mM EDTA, and 25 mM NaCl, heating at 95° C. for 10 min, and then cooling to 10° C. over approximately 15 min. The attachment polynucleotide included a 5' sequence complementary to the first tag sequence (A14') and a 3' primer sequence (P5') with a biotin at the 3' terminus (for single indexing). In some embodiments, the attachment polynucleotide included an intervening universal nitroindole sequence (for dual indexing). The annealed transposons/attachment polynucleotides (2 µM final concentration based on attachment polynucleotide) were then mixed with a transposase enzyme (6.1 µM final concentration) and incubated at 37° C. overnight to form solution-phase transposome complexes. The solution-phase transposome complexes were then immobilized on a surface of a PCR tube by mixing the complexes (having biotin) in a PCR tube with a streptavidin-coated surface. In some examples, the immobilization may be carried out in the presence of HT1 buffer (Illumina, San Diego, Calif.), which is a high salt buffer that aids formation of biotin-streptavidin bonds. After incubation for 1 h, the PCR tube was washed in a mixture of TWB buffer (Illumina, San Diego, Calif.). The resulting tubes having transposome immobilized thereon were used in single indexing and dual indexing tagmentation protocols.

The library preparation workflow, including the steps of tagmentation, extension, ligation, and indexing, were performed as outlined in Example 2. After completion of the steps as outlined in Example 2, library fragments immobilized to the surface of the tube were generated. The tubes were rinsed with 50 µL of 0.2 N NaOH to denature the library fragments and to release them from the surface of the tubes. The libraries were quantified by qPCR, and then prepared for sequencing on a MiSeq® by diluting to 5 µL of about 3200 pM and denaturing with 5 µL of 0.2 N NaOH at room temperature for 5 minutes. Chilled Illumina HT1 buffer (990 µL) was added and the full 1 mL mixture was loaded into the MiSeq® cartridge.

Figure 10:
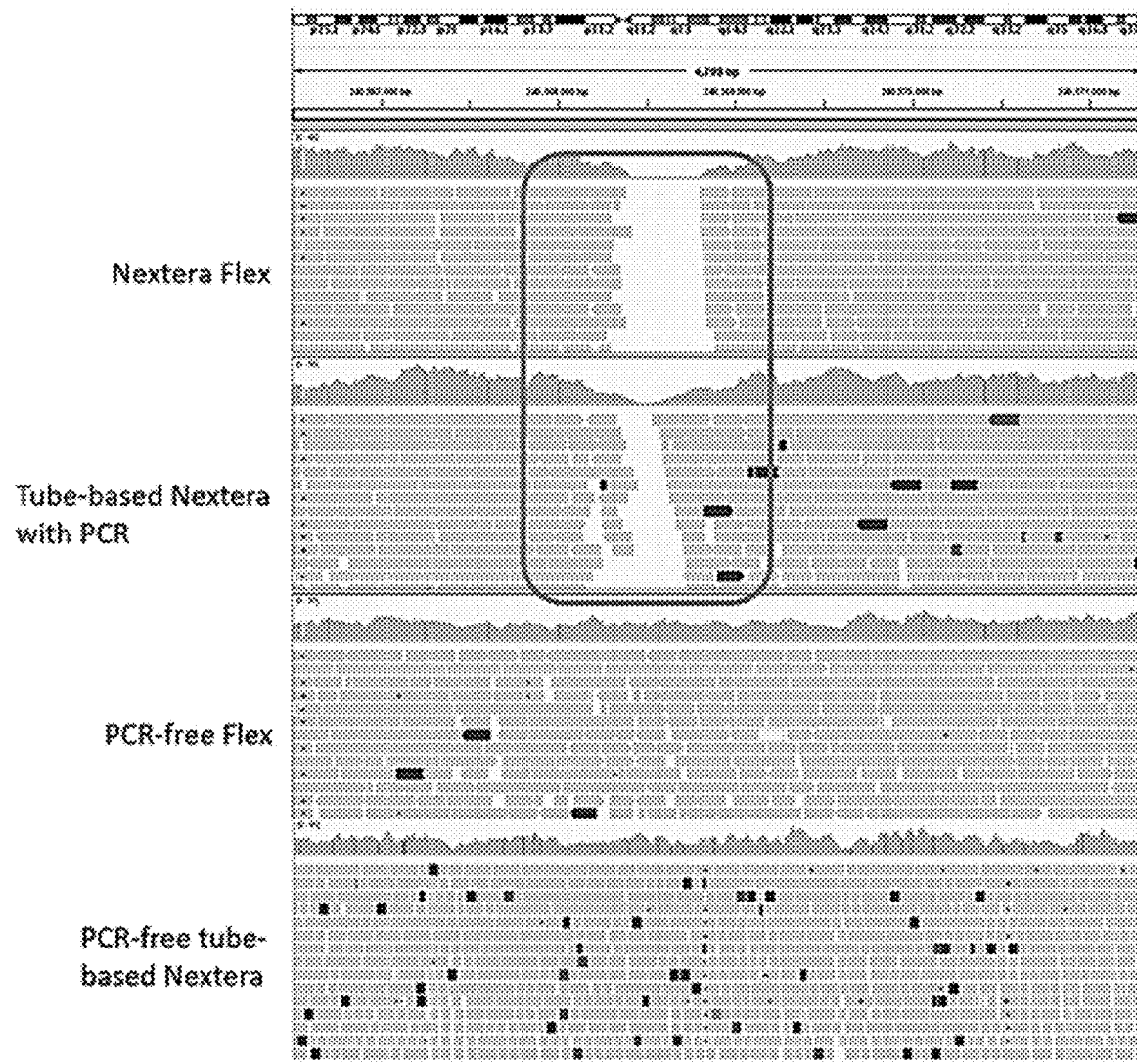
FIG. 10 depicts a graphical representation of sequencing coverage with a gap in a region of gene RNPEPL1 for PCR library preparation methods (Nextera Flex or tube-based Nextera), but with fewer gaps using PCR free methods described herein (two bottom panels).

Results of sequencing is shown in FIG. 10, which shows the coverage in a region of the genome known to be difficult to sequence (gene RNPEPL1). The two library prep methods with PCR (Nextera Flex and tube-based Nextera) show a gap where no sequences covered a region of the gene, indicated with rectangular bounding box. The two PCR-free methods were found to have good coverage in this region as shown by the sections indicated in FIG. 10 as "PCR-free Flex" and PCR-free tube-based Nextera."

Example 7: PCR-Free Preparation without Cleavable Linker

The following example demonstrates a method and system for immobilizing transposome complexes in a tube, such as in a PCR tube, for PCR-free whole genome sequencing. The methods are performed similarly to the method described in Example 2, but without an attachment nucleotide comprising a cleavable linker or a step of cleaving the linker. This method employs three separate oligonucleotides. Additional components of the method include the Tn5 transposon, SDS, an extension-ligation mix (ELM), and a streptavidin-coated surface (such as beads or a plate).

A mixture of (1) a first transposon having a ME sequence, a first tag sequence (A14), an i5 sequence, and a 5' primer sequence (P5); (2) a second transposon with a 5' complementary mosaic end sequence (ME'), a second tag (B15'), an i7' sequence, and a 3' primer sequence (P7'); and (3) an attachment polynucleotide comprising a P7 sequence and a binding element (such as biotin) can be prepared and attached to a surface (such as a streptavidin-coated plate or bead). The transposome can be built and attached to the surface in a single step in the presence of template nucleic acid in tagmentation buffer.

Tagmentation is performed for 5 min at 55° C. PEG may be included in the tagmentation reaction. The mixture is treated with SDS to remove the Tn5 transposase. ELM is performed and the supernatant is removed. No SPRI capture beads are needed with this method, and thus no need to tune insert size via bead-loading density. Fragments can be eluted in NaOH for sequencing preparation.

Example 8: PCR-Free Preparation of 96-Well Libraries

The following example demonstrates a method and system for preparing up to 96 dual-indexed paired-end libraries from a DNA sample. The methods are performed similarly to the method as described in Example 2, but use two steps of incubation with capture beads to allow preparation without a final qPCR step. As qPCR can be time-consuming (up to two hours), this protocol has the advantage of ease-of-use and shorter duration. This method was compatible with DNA inputs of 25-1000 ng. For human DNA samples and other large complex genomes, DNA input can be greater than 200 ng. For DNA input of 200 to 1000 ng, quantification and normalization of the initial DNA sample is not required. For 25 to 200 ng DNA input, libraries are quantified and normalized before sequencing.

This method uses a first transposon as described in FIG. 6D, wherein sequence X in the first transposon is ATCTGACTATCCCCTGCG (SEQ ID NO: 23), and sequence X' in the attachment polynucleotide is CGCAGGGGATAGTCAGAT (SEQ ID NO: 24). The anchor sequence is A14, and the spacer region is made up of 2 C18 and 1 C9 carbon spacers (non-DNA sequences).

Tagmentation.

DNA in 10 mM Tris-HCl (about 2-30 µL) is added to each well of a 96-well PCR plate so that the total input amount (ng) is within the desired range. If the DNA volume is <30 µL, nuclease-free water is added to the DNA samples to bring the total volume to 30 µL. A suspension of bead-linked transposomes (BLTs) (10 µL) is added to each well followed by 10 µL of tagmentation buffer. The BLTs are loaded on the beads at a concentration of from about 50 to 1000 nM. They are resuspended in 15% glycerol standard storage buffer, which consists of 15% glycerol, 100 mM NaCl, 50 mM Tris HCl pH 7.5, 0.1 mM EDTA, 1 mM DTT, 0.1% triton X-100. Samples are pipetted to mix until beads are fully resuspended, and the plate is sealed and placed on a thermal cycler at 41° C. for 5 min followed by a hold at 10° C. Tagmentation times of 15, 30, 45, 60, 75, 90, 105, 120, and 300 sec provide similar yields, with a shift to longer insert lengths for the shorter incubation times (e.g., 15 sec produced longer insert sizes than 60, 120, or 300 sec). In some examples, tagmentation time is reduced to 1 min.

To each well is added 10 µL of stop tagmentation buffer comprising SDS and the resulting mixture is pipetted until the beads are fully resuspended, and the mixture is incubated for 1-5 min. The plate is placed on a magnetic stand for 2-5 min, and the supernatant is removed and discarded. The plate is removed from the magnet, and 150 µL of tagmentation wash buffer is added directly onto the beads in each well. Samples are mixed by pipette and the plate is placed on a magnetic stand until the solution is clear (approx. 2-5 min). This step removed SDS from the samples.

Extension/Ligation.

Index 1 (i7) adapters, Index 2 (i5) adapters, and sequences required for sequencing cluster generation are added by extension/ligation. While the plate is still on the magnetic stand, the supernatant is removed and discarded. The plate is removed from the magnetic stand and 45 µL of extension ligation mix is added to each well followed by pipetting to resuspend the beads. Next, the appropriate index adapters (5 µL) are added to each sample, and the plate is sealed and placed on a thermal cycler at 37° C. for 5 min, 50° C. for 5 min, and then at hold at 10° C. The 37° C. and 50° C. incubation periods can each be performed at 1, 3, or 5 min, and all variations produce similar library yields. Shorter incubation periods produce libraries with increased fragment size, while longer incubations lead to higher concentrations of ligation products. The plate is then placed on the magnetic stand for 2-5 min and the supernatant is then removed.

To the wells is added 75 µL of tagmentation wash buffer and the mixture is pipetted to resuspend the tagmentation beads. The supernatant is discarded, and the plate is spun down and placed on the magnet for 2-5 min. To each well is added 45 µL of 0.2N NaOH to denature the fragments. The mixture in each well is pipetted to resuspend the tagmentation beads and the plate is incubated for 1-5 min at room temperature.

Library Clean-Up.

To each well is added 36 µL of capture beads (such as Ampure XP beads) and the well contents were mixed to resuspend the beads and then incubated for 1, 3, or 5 min. The plate is placed on a magnetic stand for approximately 1-5 min until the supernatant is clear.

To each well of a second 96-well plate is added 42 µL of capture beads. Then, 76 µL of the supernatant from each well of the first 96-well plate is added to the second 96-well plate with capture beads. Samples are mixed by pipette and incubated for 1, 3, or 5 min and then placed on a magnetic stand until supernatant is clear (approximately 1-5 min). In some examples, the second capture bead step is omitted.

Single or double capture bead clean-up protocols, and 1, 3, or 5 min incubations for each bead clean-up step, are suitable.

Following capture bead purification, the supernatant is discarded and the capture beads are washed twice with 180 µL of fresh 80% ethanol without mixing and incubated at room temperature, after which the supernatant is discarded. Residual ethanol is removed by pipette, and the plate is air-dried and removed from the magnetic stand.

To each well is added 15 µL-22 µL of resuspension buffer and well contents are mixed by pipetted to resuspend the beads. The plate is incubated at room temperature for 2 min and then placed on a magnetic stand until the supernatant is clear (approximately 2 min). A total of 14 µL-20 µL of supernatant from each well is transferred to a third 96-well PCR plate. This plate is the final DNA library and is prepared for sequencing as described above.

This protocol employs two purification steps with capture beads, and eliminates a qPCR step, allowing for completion of the library preparation in a shorter time. For example, samples are prepared using these methods in under 30 min when using short magnet incubation steps totaling 20 min.

The protocol can be performed in other vessels, such as microcentrifuge tubes.

In some embodiments, to achieve optimal cluster density, equal library volumes are pooled and the pool quantified before sequencing. When using 200-1000 ng DNA inputs, in some instances, libraries are combined by pooling equivolumes from each library in a 1.7 mL microcentrifuge tube, vortexing to mix, and then centrifuging. The library pool is quantified using an ssDNA Qubit kit to determine the concentration of the pool. When using 25-200 ng DNA inputs, in some examples, each library is quantified individually using an ssDNA Quibit kit.

In some examples, sequencing is done on a NovaSeq6000 cartridge.

Example 9: Preparation of Libraries Via Combined Tagmentation and Indexing

The following example demonstrates a method and system for preparing dual-indexed paired-end libraries from a DNA sample using a combined tagmentation and indexing step. The methods were performed similarly to the method as described in Example 2, but combined tagmentation and indexing in one step. By avoiding separate tagmentation and indexing steps, this protocol has the advantage of ease-of-use and shorter duration. Further, this protocol can avoid a denaturation step and produce double-stranded libraries without the need for a separate step to produce double-stranded samples from denatured single-stranded samples. This protocol can also avoid certain washing steps, further reducing the time required for the workflow.

To show that these libraries can be prepared using reactions that are given either a long, medium, or short period of time to proceed, three sets of samples can be processed at a normal workflow rate, a fast workflow rate, and a superfast workflow rate, respectively.

This method uses a first immobilized transposon complex and a second immobilized transposon complex. In the first immobilized transposon complex, sequence X in the first transposon is an anchor sequence, and sequence X' in the attachment polynucleotide is an anchor sequence complement. In the second immobilized transposon complex, sequence X in the first transposon is an anchor sequence, and sequence X' in the attachment polynucleotide is an anchor sequence complement. The anchor sequence comprised in the first and second immobilized transposon complexes may be non-complementary to avoid cross-hybridization. The first transposon complex may comprise an exemplary first attachment polynucleotide comprising (i) an anchor sequence complement, an A14' sequence, a spacer, and a P5' sequence, and (ii) a binding element comprising biotin, and the second transposon complex may comprise an exemplary second attachment polynucleotide comprising (i) an anchor sequence complement, a B15' sequence, a spacer, and a P7' sequence, and (ii) a binding element comprising biotin.

Tagmentation and Indexing. DNA in 10 mM Tris-HCl (about 2-30 µL) is added to each well of a 96-well PCR plate so that the total input amount (ng) is within the desired range. A suspension of bead-linked transposomes (BLTs, i.e., the immobilized transposon complexes) comprising the first and second transposome complexes is added to each well. An indexing step is performed in a single reaction solution with Index 1 (i7) adapters, Index 2 (i5) adapters, and sequences required for sequencing cluster generation ligated in the same reaction solution as the tagmentation. In this example, first indexing oligonucleotides comprises a A14 sequence, i5 sequence, and P5 sequence, and second indexing oligonucleotides comprises a B15 sequence, i7 sequence, and P7 sequence. Conditions for the tagmentation/ligation step include tagmentation buffer and *E. Coli* DNA ligase added to the mixture of target DNA, first and second transposome complexes, and the first and second indexing oligonucleotides for a total volume of 20 µL. The tagmentation and indexing reaction is conducted at a temperature of 41° C. for three different time intervals (for three different samples): 15 minutes (normal workflow), 5 minutes (fast workflow), and 1 minute (superfast workflow).

Following the combined tagmentation and indexing reaction, to each well is added 5 µL of 0.6% SDS with an incubation at 37° C. to stop the tagmentation reaction by washing with SDS to denature the transposase. The stopping step was conducted for three different time intervals (for three different samples): 5 minutes (normal workflow), 5 minutes (fast workflow), and 1 minute (superfast workflow). While the stopping step is conducted for the same period of time for the normal and fast workflow, the overall time for the fast workflow is still shorter due to time differences in the other steps.

Extension. To each well is added 75 µL of extension mix (DNA polymerase, dNTPs, and buffer), and the extension reaction proceeds at <68° C. in a 100 µL reaction volume. The extension step is conducted for three different time intervals (for three different samples): 10 minutes (normal workflow), 2 minutes (fast workflow), and 1 minute (superfast workflow). This extension step can generate a double-stranded DNA library in solution. Library clean-up may be performed with capture beads.

Overall, library yields of the normal and fast workflow are comparable to methods that had separate tagmentation and indexing steps, while the library yields of the superfast workflow are likely sufficient for many uses, especially considering the added convenience of the even faster workflow. Methods with combined tagmentation and indexing may allow indexing oligonucleotides to associate with transposases that did not successfully fragment the DNA sample (i.e., side tagmentation products). Further, combined tagmentation and indexing may generate library products having P5/P5 sequences or P7/P7 sequences at both ends, and these library products with homozygous ends may not sequence properly. However, for many applications, the amount of starting DNA sample is sufficient to enable sequencing results even if some side products are generated.

A number of embodiments have been described. Nevertheless, it will be understood that various modifications may be made. Accordingly, other embodiments are within the scope of the following claims.

SEQUENCE LISTING

SEQ ID NO: 1 - A14-ME
TCGTCGGCAGCGTCAGATGTGTATAAGAGACAG

SEQ ID NO: 2 - B15-ME
GTCTCGTGGGCTCGGAGATGTGTATAAGAGACAG

SEQ ID NO: 3 - ME'
phos-CTGTCTCTTATACACATCT

SEQ ID NO: 4 - A14
TCGTCGGCAGCGTC

SEQ ID NO: 5 - B15
GTCTCGTGGGCTCGG

SEQ ID NO: 6 - ME
AGATGTGTATAAGAGACAG

SEQ ID NO: 7 - P5
AATGATACGGCGACCACCGAGAUCTACAC

SEQ ID NO: 8 - P7
CAAGCAGAAGACGGCATACGAG*A

SEQ ID NO: 9 - P5_A14_ME
AATGATACGGCGACCACCGAGATCTACACTCGTCGGCAGCGTCAGATGT
GTATAAGAGACAG

SEQ ID NO: 10 - P_ME'_B15'
5Phos/CTGTCTCTTATACACATCTCCGAGCCCACGAGAC

SEQ ID NO: 11 - Bio_P7_i701_B1_5_ddC
5Biosg/CAAGCAGAAGACGGCATACGAGATTCGCCTTAGTCTCGTGGG
CTCGG/3ddC/

SEQ ID NO: 12 - A14'_P5'_bio
GACGCTGCCGACGAGTGTAGATCTCGGTGGTCGCCGTATCATT/3Bio/

SEQ ID NO: 13 - P_A14_ME
5Phos/TCGTCGGCAGCGTCAGATGTGTATAAGAGACAG

SEQ ID NO: 14 - A14'_nitro_P5'_bio
GACGCTGCCGACGACCC/i5NitInd//i5NitInd//i5NitInd//
i5NitInd//i5NitInd//i5NitInd//i5NitInd//i5NitInd/
GTGTAGATCTCGGTGGTCGCCGTATCATT/3Bio/

SEQ ID NO: 15 - A14'_12anc'_2sp_P5'_bio
GACGCTGCCGACGACCGAGCATATCC/iSp18//iSp18/GTGTAGAT
CTCGGTGGTCGCCGTATCATT/3BioTEG/

SEQ ID NO: 16 - P5_i501
AATGATACGGCGACCACCGAGATCTACACTAGATCGC

SEQ ID NO: 17 - P_i701'_P7_ddC
5Phos/TAAGGCGAATCTCGTATGCCGTCTTCTGCTTG/3ddC/

SEQ ID NO: 18 - P7_i701_B15_ddC
CAAGCAGAAGACGGCATACGAGATTCGCCTTAGTCTCGTGGGCTCGG/
3ddC/

SEQ ID NO: 19 - P5_i501_12anc
AATGATACGGCGACCACCGAGATCTACACTAGATCGCGGATATGCTCGG

SEQ ID NO: 20 - biotinylated oligonucleotide
/5Biosg/TTUUUAATGATACGGCGACCACCGAGATCTACACTCGTCGG
CAGCGTCAGATGTGTATAAGAGACA SEQ ID NO: 21 - ME'_B15'_P7'
CTGTCTCTTATACACATCTCCGAGCCCACGAGACATCTCGTATGCCGTC
TTCTGCTTG SEQ ID NO: 22 - Exemplary anchor sequence
GGATATGCTCGG SEQ ID NO: 23: Exemplary sequence X
ATCTGACTATCCCCTGCG SEQ ID NO: 24: Exemplary sequence X'
CGCAGGGGATAGTCAGAT

---

What is claimed is:

1. An annealed transposon/attachment polynucleotide hybrid comprising:
   (a) a first transposon comprising a 3' transposon end sequence and a 5' adaptor sequence;
   (b) a second transposon comprising a 5' transposon end sequence and a 3' adaptor sequence, wherein
      i. the second transposon 5' transposon end sequence is complementary to the first transposon 3' transposon end sequence, forming a double-stranded transposon end sequence to which the transposase is bound,
      ii. the 5' adaptor sequence of the first transposon and the 3' adaptor sequence of the second transposon are non-complementary, and
      iii. the first transposon and the second transposon form a Y-shape; and
   (c) an attachment polynucleotide comprising:
      i. an attachment adaptor sequence hybridized to either the first transposon 5' adaptor sequence or the second transposon 3' adaptor sequence; and
      ii. a biotin linker.

2. A transposome complex comprising:
   (a) a transposase;
   (b) a first transposon comprising a 3' transposon end sequence and a 5' adaptor sequence;
   (c) a second transposon comprising a 5' transposon end sequence and a 3' adaptor sequence, wherein
      i. the second transposon 5' transposon end sequence is complementary to the first transposon 3' transposon end sequence, forming a double-stranded transposon end sequence to which the transposase is bound,
      ii. the 5' adaptor sequence of the first transposon and the 3' adaptor sequence of the second transposon are non-complementary, and
      iii. the first transposon and the second transposon form a Y-shape; and
   (d) an attachment polynucleotide comprising:
      i. an attachment adaptor sequence hybridized to either the first transposon 5' adaptor sequence or the second transposon 3' adaptor sequence and
      ii. a biotin linker.

3. An immobilized transposome complex comprising:
a solid support; and
a transposome complex immobilized to the solid support, wherein the transposome complex comprises:
   (a) a transposase;
   (b) a first transposon comprising a 3' transposon end sequence and a 5' adaptor sequence;
   (c) a second transposon comprising a 5' transposon end sequence and a 3' adaptor sequence, wherein
      i. the second transposon 5' transposon end sequence is complementary to at least a portion of the first transposon 3' transposon end sequence, forming a double-stranded transposon end sequence to which the transposase is bound,
      ii. the 5' adaptor sequence of the first transposon and the 3' adaptor sequence of the second transposon are non-complementary, and
      iii. the first transposon and the second transposon form a Y-shape; and
   (d) an attachment polynucleotide comprising:
      i. an attachment adaptor sequence hybridized to either the first transposon 5' adaptor sequence or the second transposon 3' adaptor sequence and
      ii. a biotin linker,
   wherein the biotin linker is immobilized to the solid support.

4. The immobilized transposome complex of claim 3, wherein the biotin linker comprises a cleavable linker.

5. The transposome complex of claim 2, wherein the attachment polynucleotide further comprises a spacer region, an anchor region, a primer sequence, or an index tag sequence, or a combination thereof, and optionally further comprises a capture sequence, a barcode sequence, a cleavage sequence, or a sequencing-related sequence, or a combination thereof, optionally wherein:
  (a) the first transposon further comprises a primer sequence 5' of the 5' adaptor sequence, and the attachment polynucleotide comprises (i) a portion complementary and hybridized to the 5' adaptor sequence and (ii) a sequence that is complementary to the primer sequence;
  (b) the first transposon further comprises a primer sequence 5' of the 5' adaptor sequence, and the attachment polynucleotide comprises a sequence that is complementary to the primer sequence;
  (c) the second transposon comprises the 3' adaptor sequence and the attachment polynucleotide comprises (i) a portion complementary and hybridized to the 3' adaptor sequence, (ii) an index tag sequence, and (iii) a primer sequence; and/or
  (d) the attachment polynucleotide comprises a spacer region or a spacer region and an anchor region, optionally wherein the first transposon comprises the 5' adaptor sequence, and the attachment polynucleotide comprises (i) a portion complementary and hybridized to the 5' adaptor sequence, (ii) a spacer region, and (iii) a primer sequence.

6. The transposome complex of claim 2, wherein the attachment polynucleotide comprises an A14' sequence.

7. The transposome complex of claim 5, wherein the spacer region
  a) is a non-DNA spacer;
  b) is a length of approximately 2, 3, 4, 5, 6, 7, 8, 9, 10, 12, 15, 20, or 30 base pairs, optionally wherein the spacer region is a length of approximately 8 or 10 base pairs or nucleotides;
  c) comprises universal bases, optionally wherein the universal bases comprise an inosine or a nitroindole sequence; and/or
  d) comprises one or more C18 spacers, one or more C9 spacers, or a combination thereof, optionally wherein the spacer region comprises a 2×sp18 synthetic linker, two C18 spacers, a C9 spacer, or two C18 spacers and one C9 spacer.

8. The transposome complex of claim 5, wherein the anchor region is complementary to an anchor region complement of an indexing oligonucleotide, where the indexing oligonucleotide comprises the anchor region complement and an index tag sequence (-Anchor'-Index Tag Sequence-), optionally wherein the anchor region complement is common to a plurality of indexing oligonucleotides and/or each index tag sequence of a plurality of indexing oligonucleotides is the same or different.

9. The transposome complex of claim 2, wherein the transposase is a Tn5 transposase, a wild-type Tn5 transposase, or a hyperactive Tn5 transposase, or a mutant thereof; and/or the primer sequence of the attachment polynucleotide is complementary to an index primer sequence of the indexing polynucleotide.

10. The immobilized transposome complex of claim 3, wherein the solid support is a bead, a paramagnetic bead, a flow cell, a surface of a microfluidic device, a tube, a well of a plate, a slide, a patterned surface, or a microparticle, optionally wherein the solid support comprises a plurality of solid supports, optionally wherein the plurality of solid supports comprises a plurality of beads.

11. A kit comprising:
  a transposome complex of claim 2; and
  an index mix comprising index sequences, optionally wherein the index mix comprises i5 index sequences and i7 index sequences, wherein the i5 index sequences hybridize to the attachment polynucleotide, and wherein the i7 index sequences hybridize to the 3' adaptor sequence.

* * * * *

SEQUENCE LISTING

<160> NUMBER OF SEQ ID NOS: 24

<210> SEQ ID NO 1
<211> LENGTH: 33
<212> TYPE: DNA
<213> ORGANISM: Artificial sequence
<220> FEATURE:
<223> OTHER INFORMATION: Exemplary sequence used in a transposome
      complex

<400> SEQUENCE: 1
tcgtcggcag cgtcagatgt gtataagaga cag                                    33

```
<210> SEQ ID NO 2
<211> LENGTH: 34
<212> TYPE: DNA
<213> ORGANISM: Artificial sequence
<220> FEATURE:
<223> OTHER INFORMATION: Exemplary sequence used in a transposome
      complex

<400> SEQUENCE: 2
gtctcgtggg ctcggagatg tgtataagag acag                              34

<210> SEQ ID NO 3
<211> LENGTH: 19
<212> TYPE: DNA
<213> ORGANISM: Artificial sequence
<220> FEATURE:
<223> OTHER INFORMATION: Exemplary sequence used in a transposome
      complex
<220> FEATURE:
<221> NAME/KEY: misc_feature
<222> LOCATION: (1)..(1)
<223> OTHER INFORMATION: 5' phosphate group

<400> SEQUENCE: 3
ctgtctctta tacacatct                                               19

<210> SEQ ID NO 4
<211> LENGTH: 14
<212> TYPE: DNA
<213> ORGANISM: Artificial sequence
<220> FEATURE:
<223> OTHER INFORMATION: Exemplary attachment adaptor sequence

<400> SEQUENCE: 4
tcgtcggcag cgtc                                                    14

<210> SEQ ID NO 5
<211> LENGTH: 15
<212> TYPE: DNA
<213> ORGANISM: Artificial sequence
<220> FEATURE:
<223> OTHER INFORMATION: Exemplary attachment adaptor sequence

<400> SEQUENCE: 5
gtctcgtggg ctcgg                                                   15

<210> SEQ ID NO 6
<211> LENGTH: 19
<212> TYPE: DNA
<213> ORGANISM: Artificial sequence
<220> FEATURE:
<223> OTHER INFORMATION: Exemplary sequence used in a transposome
      complex

<400> SEQUENCE: 6
agatgtgtat aagagacag                                               19

<210> SEQ ID NO 7
<211> LENGTH: 29
<212> TYPE: DNA
<213> ORGANISM: Artificial sequence
<220> FEATURE:
<223> OTHER INFORMATION: Exemplary primer

<400> SEQUENCE: 7
aatgatacgg cgaccaccga gauctacac                                    29
```

```
<210> SEQ ID NO 8
<211> LENGTH: 24
<212> TYPE: DNA
<213> ORGANISM: Artificial sequence
<220> FEATURE:
<223> OTHER INFORMATION: Exemplary primer
<220> FEATURE:
<221> NAME/KEY: misc_feature
<222> LOCATION: (22)..(22)
<223> OTHER INFORMATION: Optionally modified guanine, e.g., 8-oxo-
      guanine
<220> FEATURE:
<221> NAME/KEY: misc_feature
<222> LOCATION: (22)..(23)
<223> OTHER INFORMATION: Optional phosphorothioate bond

<400> SEQUENCE: 8
caagcagaag acggcatacg agat                                          24

<210> SEQ ID NO 9
<211> LENGTH: 62
<212> TYPE: DNA
<213> ORGANISM: Artificial sequence
<220> FEATURE:
<223> OTHER INFORMATION: Exemplary 5' transposon arm

<400> SEQUENCE: 9
aatgatacgg cgaccaccga gatctacact cgtcggcagc gtcagatgtg tataagagac   60
ag                                                                  62

<210> SEQ ID NO 10
<211> LENGTH: 34
<212> TYPE: DNA
<213> ORGANISM: Artificial sequence
<220> FEATURE:
<223> OTHER INFORMATION: Exemplary 3' transposon arm
<220> FEATURE:
<221> NAME/KEY: misc_feature
<222> LOCATION: (1)..(1)
<223> OTHER INFORMATION: 5' phosphate group

<400> SEQUENCE: 10
ctgtctctta tacacatctc cgagcccacg agac                               34

<210> SEQ ID NO 11
<211> LENGTH: 48
<212> TYPE: DNA
<213> ORGANISM: Artificial sequence
<220> FEATURE:
<223> OTHER INFORMATION: Exemplary attachment oligonucleotide
<220> FEATURE:
<221> NAME/KEY: misc_feature
<222> LOCATION: (1)..(1)
<223> OTHER INFORMATION: 5' Biotin
<220> FEATURE:
<221> NAME/KEY: misc_feature
<222> LOCATION: (48)..(48)
<223> OTHER INFORMATION: 3' Dideoxy-C

<400> SEQUENCE: 11
caagcagaag acggcatacg agattcgcct tagtctcgtg ggctcggn                48

<210> SEQ ID NO 12
<211> LENGTH: 43
<212> TYPE: DNA
<213> ORGANISM: Artificial sequence
<220> FEATURE:
<223> OTHER INFORMATION: Exemplary attachment oligonucleotide
<220> FEATURE:
<221> NAME/KEY: misc_feature
```

<222> LOCATION: (43)..(43)
<223> OTHER INFORMATION: 3' Biotin

<400> SEQUENCE: 12
gacgctgccg acgagtgtag atctcggtgg tcgccgtatc att        43

<210> SEQ ID NO 13
<211> LENGTH: 33
<212> TYPE: DNA
<213> ORGANISM: Artificial sequence
<220> FEATURE:
<223> OTHER INFORMATION: Exemplary 5' transposon arm
<220> FEATURE:
<221> NAME/KEY: misc_feature
<222> LOCATION: (1)..(1)
<223> OTHER INFORMATION: 5' phosphate group

<400> SEQUENCE: 13
tcgtcggcag cgtcagatgt gtataagaga cag        33

<210> SEQ ID NO 14
<211> LENGTH: 54
<212> TYPE: DNA
<213> ORGANISM: Artificial sequence
<220> FEATURE:
<223> OTHER INFORMATION: Exemplary attachment oligonucleotide
<220> FEATURE:
<221> NAME/KEY: misc_feature
<222> LOCATION: (18)..(25)
<223> OTHER INFORMATION: Int 5-Nitroindole
<220> FEATURE:
<221> NAME/KEY: misc_feature
<222> LOCATION: (54)..(54)
<223> OTHER INFORMATION: 3' Biotin

<400> SEQUENCE: 14
gacgctgccg acgacccnnn nnnnngtgta gatctcggtg gtcgccgtat catt        54

<210> SEQ ID NO 15
<211> LENGTH: 57
<212> TYPE: DNA
<213> ORGANISM: Artificial sequence
<220> FEATURE:
<223> OTHER INFORMATION: Exemplary attachment oligonucleotide
<220> FEATURE:
<221> NAME/KEY: misc_feature
<222> LOCATION: (27)..(28)
<223> OTHER INFORMATION: Int Spacer 18
<220> FEATURE:
<221> NAME/KEY: misc_feature
<222> LOCATION: (57)..(57)
<223> OTHER INFORMATION: 3' Biotin-TEG

<400> SEQUENCE: 15
gacgctgccg acgaccgagc atatccnngt gtagatctcg gtggtcgccg tatcatt        57

<210> SEQ ID NO 16
<211> LENGTH: 37
<212> TYPE: DNA
<213> ORGANISM: Artificial sequence
<220> FEATURE:
<223> OTHER INFORMATION: Exemplary i501 indexing oligonucleotide

<400> SEQUENCE: 16
aatgatacgg cgaccaccga gatctacact agatcgc        37

<210> SEQ ID NO 17
<211> LENGTH: 33
<212> TYPE: DNA

```
<213> ORGANISM: Artificial sequence
<220> FEATURE:
<223> OTHER INFORMATION: Exemplary i701 indexing oligonucleotide
<220> FEATURE:
<221> NAME/KEY: misc_feature
<222> LOCATION: (1)..(1)
<223> OTHER INFORMATION: 5' phosphate group
<220> FEATURE:
<221> NAME/KEY: misc_feature
<222> LOCATION: (33)..(33)
<223> OTHER INFORMATION: 3' Dideoxy-C

<400> SEQUENCE: 17
taaggcgaat ctcgtatgcc gtcttctgct tgn                            33

<210> SEQ ID NO 18
<211> LENGTH: 48
<212> TYPE: DNA
<213> ORGANISM: Artificial sequence
<220> FEATURE:
<223> OTHER INFORMATION: Exemplary i701 indexing oligonucleotide
<220> FEATURE:
<221> NAME/KEY: misc_feature
<222> LOCATION: (48)..(48)
<223> OTHER INFORMATION: 3' Dideoxy-C

<400> SEQUENCE: 18
caagcagaag acggcatacg agattcgcct tagtctcgtg ggctcggn            48

<210> SEQ ID NO 19
<211> LENGTH: 49
<212> TYPE: DNA
<213> ORGANISM: Artificial sequence
<220> FEATURE:
<223> OTHER INFORMATION: Exemplary i501 indexing oligonucleotide

<400> SEQUENCE: 19
aatgatacgg cgaccaccga gatctacact agatcgcgga tatgctcgg           49

<210> SEQ ID NO 20
<211> LENGTH: 66
<212> TYPE: DNA
<213> ORGANISM: Artificial sequence
<220> FEATURE:
<223> OTHER INFORMATION: Exemplary sequence used in a transposome
      complex
<220> FEATURE:
<221> NAME/KEY: misc_feature
<222> LOCATION: (1)..(1)
<223> OTHER INFORMATION: 5' biotin

<400> SEQUENCE: 20
ttuuuaatga tacggcgacc accgagatct acactcgtcg gcagcgtcag atgtgtataa  60
gagaca                                                            66

<210> SEQ ID NO 21
<211> LENGTH: 58
<212> TYPE: DNA
<213> ORGANISM: Artificial sequence
<220> FEATURE:
<223> OTHER INFORMATION: Exemplary sequence used in a transposome
      complex

<400> SEQUENCE: 21
ctgtctctta tacacatctc cgagcccacg agacatctcg tatgccgtct tctgcttg    58

<210> SEQ ID NO 22
<211> LENGTH: 12
```

```
<212> TYPE: DNA
<213> ORGANISM: Artificial sequence
<220> FEATURE:
<223> OTHER INFORMATION: Exemplary anchor sequence

<400> SEQUENCE: 22
ggatatgctc gg                                                          12

<210> SEQ ID NO 23
<211> LENGTH: 18
<212> TYPE: DNA
<213> ORGANISM: Artificial sequence
<220> FEATURE:
<223> OTHER INFORMATION: Exemplary sequence X

<400> SEQUENCE: 23
atctgactat cccctgcg                                                    18

<210> SEQ ID NO 24
<211> LENGTH: 18
<212> TYPE: DNA
<213> ORGANISM: Artificial sequence
<220> FEATURE:
<223> OTHER INFORMATION: Exemplary sequence X'

<400> SEQUENCE: 24
cgcaggggat agtcagat                                                    18
```